(12) United States Patent
Flynn et al.

(10) Patent No.: US 10,964,142 B2
(45) Date of Patent: Mar. 30, 2021

(54) SECURE STORAGE SYSTEMS AND METHODS

(71) Applicant: Binbox, Inc., Sterling, VA (US)

(72) Inventors: Daniel Flynn, Sterling, VA (US); Eric Wesley Herring, Hillsboro, VA (US)

(73) Assignee: Binbox, Inc., Sterling, VA (US)

( * ) Notice: Subject to any disclaimer, the term of this patent is extended or adjusted under 35 U.S.C. 154(b) by 0 days.

(21) Appl. No.: 16/858,445

(22) Filed: Apr. 24, 2020

(65) Prior Publication Data

US 2020/0258334 A1    Aug. 13, 2020

Related U.S. Application Data

(63) Continuation of application No. 16/446,594, filed on Jun. 19, 2019, now Pat. No. 10,672,211, which is a
(Continued)

(51) Int. Cl.
*H04L 9/30* (2006.01)
*H04L 9/32* (2006.01)
(Continued)

(52) U.S. Cl.
CPC ....... *G07C 9/00817* (2013.01); *G06Q 20/203* (2013.01); *G06Q 20/322* (2013.01);
(Continued)

(58) Field of Classification Search
CPC .............. G06Q 20/322; G06Q 20/327; G07C 2009/00388; G07C 2009/00412;
(Continued)

(56) References Cited

U.S. PATENT DOCUMENTS

2016/0094551 A1    3/2016  Sugihara et al.
2017/0235896 A1*   8/2017  DeBusk ............. G06K 7/10366
                                                                                    705/2
(Continued)

OTHER PUBLICATIONS

International Search Report and Written Opinion, PCT Application No. PCT/US20/38584, dated Aug. 14, 2020, 8 pages.

*Primary Examiner* — Dionne Pendleton
(74) *Attorney, Agent, or Firm* — Robert L Protheroe

(57) ABSTRACT

Secure custody transfers of items among entities including secure lockable compartments are disclosed, wherein users may securely transfer custody of items to and from secure lockable compartments. Records of custody transfers and the custody transfers recorded therein may be associated to a chain of custody. A chain of custody may have an originating entity, one or more intermediary entities, which may include secure lockable compartments, and an end recipient entity. Custody transfers to a secure lockable compartment may include a release authority specifying a subsequent custody transfer, wherein a specified receiving user may access the secure lockable compartment using a portable wireless device and/or using a keypad to enter a provided access token. Custody transfer records may be secured using record certificates useable to authenticate data comprised therein. Record certificates may be written to and retrieved from a ledger, which may be a secure ledger such as a blockchain ledger.

20 Claims, 29 Drawing Sheets

Related U.S. Application Data continuation-in-part of application No. 16/389,841, filed on Apr. 19, 2019, now abandoned, which is a continuation of application No. 16/117,583, filed on Aug. 30, 2018, now abandoned.

(60) Provisional application No. 62/552,423, filed on Aug. 31, 2017.

(51) Int. Cl.

| | | |
|---|---|---|
| *G07C 9/00* | (2020.01) | |
| *H04L 9/08* | (2006.01) | |
| *H04L 9/16* | (2006.01) | |
| *G06Q 20/32* | (2012.01) | |
| *G07F 7/12* | (2006.01) | |
| *G16H 20/10* | (2018.01) | |
| *H04W 4/70* | (2018.01) | |
| *H04W 4/35* | (2018.01) | |
| *G06Q 20/20* | (2012.01) | |
| *G06Q 20/40* | (2012.01) | |

(52) U.S. Cl.
CPC ......... *G06Q 20/327* (2013.01); *G06Q 20/401* (2013.01); *G07C 9/00182* (2013.01); *G07C 9/00309* (2013.01); *G07C 9/00571* (2013.01); *G07C 9/00912* (2013.01); *G07F 7/12* (2013.01); *G16H 20/10* (2018.01); *H04L 9/0819* (2013.01); *H04L 9/0861* (2013.01); *H04L 9/16* (2013.01); *H04L 9/3271* (2013.01); *H04W 4/35* (2018.02); *H04W 4/70* (2018.02); *G07C 2009/00388* (2013.01); *G07C 2009/00412* (2013.01); *G07C 2009/00825* (2013.01)

(58) Field of Classification Search
CPC ...... G07C 2009/00825; G07C 2209/08; G07C 9/00571; G07C 9/00817; G07C 9/00896; G07C 9/00912; G07C 9/00309; G07C 2009/00769; G07C 9/00087; G07C 9/00111; G07C 9/00007; G07C 9/00563; G07C 9/00182; G07C 2209/63; G07C 9/00158; G07C 2009/00095; G07C 2009/00793; G07C 2009/0092; G07C 9/00031; G07C 9/00071; G07C 9/00126; G07C 9/00166; G07C 5/008; G07C 9/00015; G07C 9/00142; G07C 9/0069; G07C 2009/00253; G07C 2009/0038; G07C 2009/00396; G07C 2009/00634; G07C 2209/64; G07C 5/085; G07C 9/00023; G07C 9/00103; G07C 9/00174; G07C 9/025; G07C 2009/0019; G07C 2009/00206; G07C 2009/00214; G07C 2009/00222; G07C 2009/00277; G07C 2009/00301; G07C 2009/00341; G07C 2009/00349; G07C 2009/00357; G07C 2009/00373; G07C 2009/00492; G07C 2009/00507; G07C 2009/00555; G07C 2009/00579; G07C 2009/00746; G07C 2009/00753; G07C 2009/00761; G07C 2009/00809; G07C 2009/00841; G07C 2009/00849; G07C 2009/00888; G07C 2009/0096; G07C 2205/02; G07C 2209/10; G07C 2209/14; G07C 2209/62; G07C 2209/65; G07F 7/12; H04L 2209/38; H04L 2209/80; H04L 2209/84; H04L 9/006; H04L 9/0819; H04L 9/0861; H04L 9/0891; H04L 9/0894; H04L 9/16; H04L 9/3228; H04L 9/3234; H04L 9/3239; H04L 9/3271; G08C 17/02; G08C 2201/30; G08C 2201/32; G08C 2201/50; G08C 2201/93; G08C 17/00; G08C 2201/40; G08C 19/00; G08C 19/34; G08C 2201/00; G08C 2201/12; G08C 2201/20; G08C 2201/34; G08C 2201/42; G08C 2201/92; G08C 23/00; G08C 23/04

See application file for complete search history.

(56) References Cited

U.S. PATENT DOCUMENTS

| | | | |
|---|---|---|---|
| 2018/0300679 A1* | 10/2018 | Mahmood | ......... H04L 29/06802 |
| 2018/0350177 A1* | 12/2018 | Dautz | ................ G07C 9/00309 |
| 2019/0180291 A1* | 6/2019 | Schmeling | ............. G16H 20/10 |
| 2019/0280860 A1 | 9/2019 | Peddada et al. | |
| 2020/0134760 A1* | 4/2020 | Messerges | .............. G06F 16/27 |

\* cited by examiner

Lock Access Table 200

| Location ID 210 | Locker ID 212 | Lock ID 214 | Input Code 216 | Der. Key 218 | Seq. No. 220 |
|---|---|---|---|---|---|
| 201: Location ID1 "Locker Bank 130" | Locker ID1 "Locker 120a" | Lock ID1 "Lock 122a/162a" | Input Code | Der. Key | Seq. No. |
| 202: Location ID1 "Locker Bank 130" | Locker ID2 "Locker 120b" | Lock ID2 "Lock 122b/162b" | Input Code | Der. Key | Seq. No. |
| 203: Location ID2 "Locker Bank 132" | Locker ID2 "Locker 120c" | Lock ID2 "Lock 122c" | Input Code | Der. Key | Seq. No. |
| 204: Location ID2 "Locker Bank 132" | Locker ID2 "Locker 120d" | Lock ID2 "Lock 122d" | Input Code | Der. Key | Seq. No. |
| ... | ... | ... | ... | ... | ... |
| 205: Location ID1 "Locker Bank 134" | Locker ID2 "Locker 120e" | Lock ID2 "Lock 122e/162e" | Input Code | Der. Key | Seq. No. |
| 206: Location IDx "Locker Bank 134" | Locker IDy "Locker 120f" | Lock IDy "Lock 122f/162f" | Input Code | Der. Key | Seq. No. |

FIG. 2A

| Access Event Table 230 | | | | | | | | |
|---|---|---|---|---|---|---|---|---|
| Event ID 234 | Event Type 236 | Access ID 238 | Event Time 240 | Location ID 242 | Locker ID 244 | Lock ID 246 | Accessor ID 248 | Event Data 250 |
| ... | ... | ... | ... | ... | ... | ... | ... | ... |
| 231 Event ID | Event Type | Access ID | Event Time | Location ID | Locker ID | Lock ID | Accessor ID | Event Data |
| ... | ... | ... | ... | ... | ... | ... | ... | ... |
| 232 Event ID | Event Type | Access ID | Event Time | Location ID | Locker ID | Lock ID | Accessor ID | Event Data |
| ... | ... | ... | ... | ... | ... | ... | ... | ... |
| 233 Event ID | Event Type | Access ID | Event Time | Location ID | Locker ID | Lock ID | Accessor ID | Event Data |
| ... | ... | ... | ... | ... | ... | ... | ... | ... |

FIG. 2B

| Lockable Compartment Access Table 260 | | | | | | | |
|---|---|---|---|---|---|---|---|
| Access ID 264 | Access Type 266 | Access Time 268 | Location ID 270 | Locker ID 272 | Lock ID 274 | Accessor ID 276 | Access Data 278 |
| ... | ... | ... | ... | ... | ... | ... | ... |
| Access ID | Access Type | Access Time | Location ID | Locker ID | Lock ID | Accessor ID | Access Data |
| ... | ... | ... | ... | ... | ... | ... | ... |
| Access ID | Access Type | Access Time | Location ID | Locker ID | Lock ID | Accessor ID | Access Data |
| ... | ... | ... | ... | ... | ... | ... | ... |
| Access ID | Access Type | Access Time | Location ID | Locker ID | Lock ID | Accessor ID | Access Data |
| ... | ... | ... | ... | ... | ... | ... | ... |

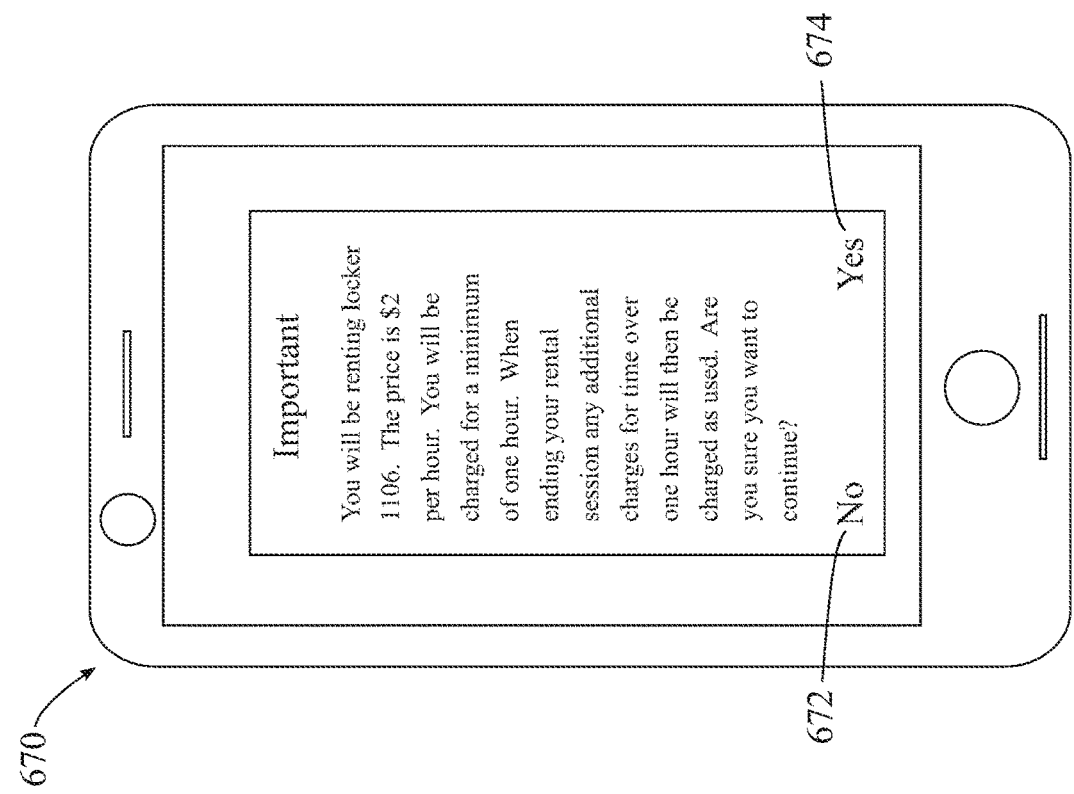
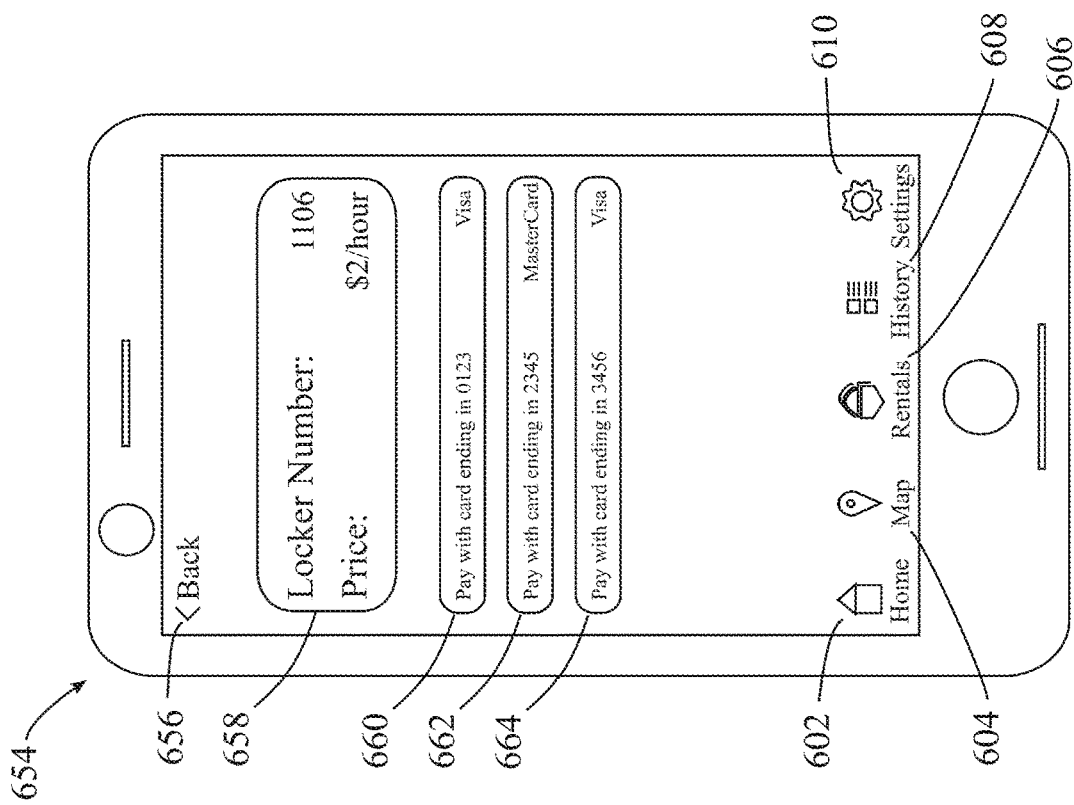
FIG. 6F
FIG. 6E

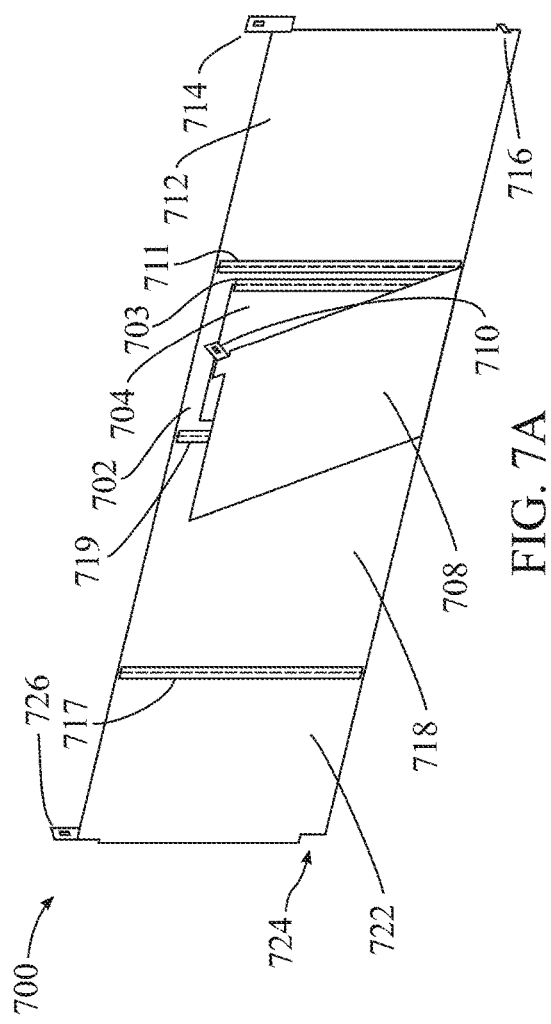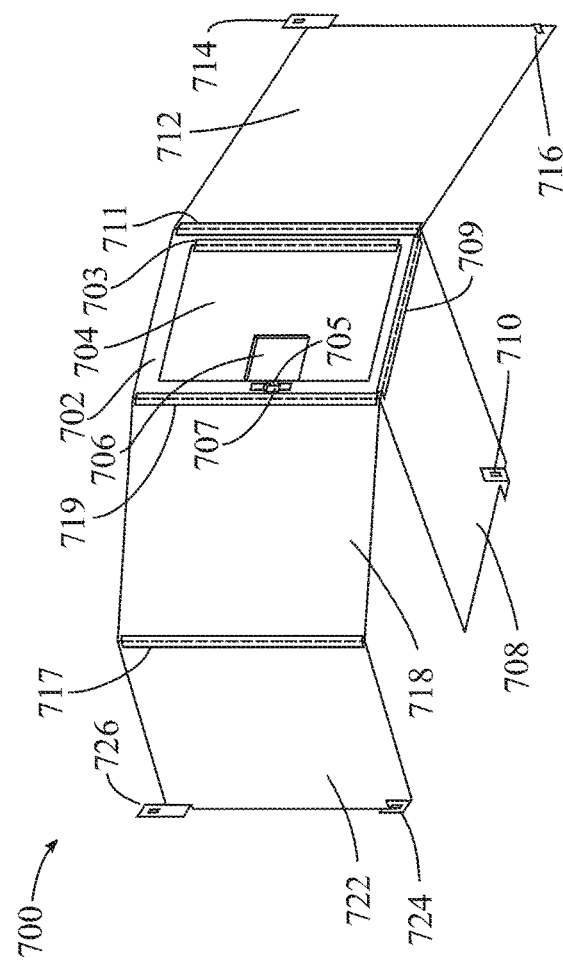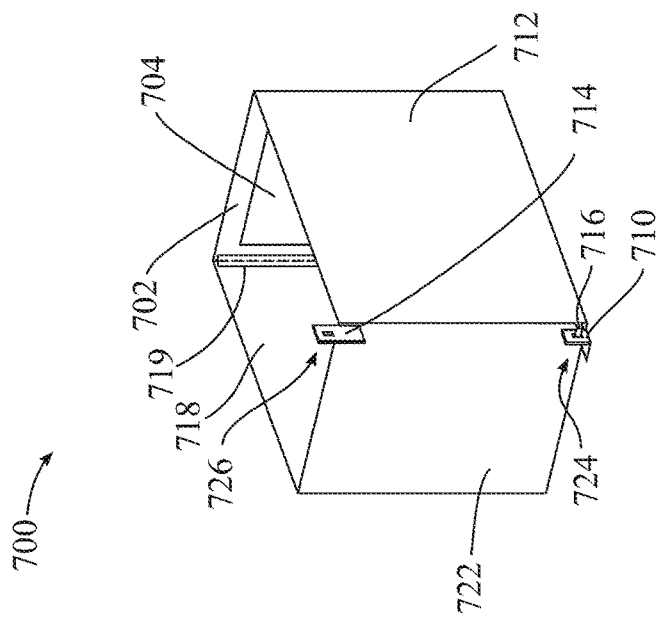

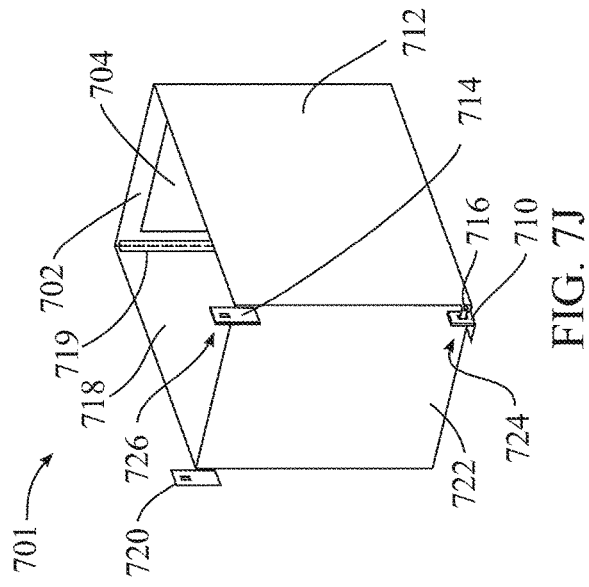
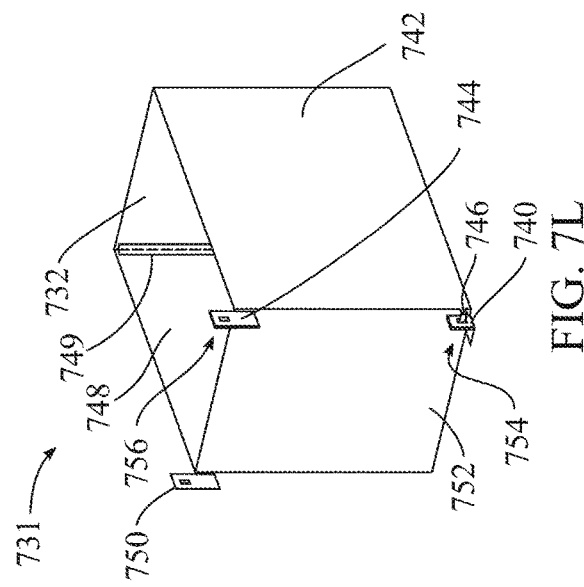
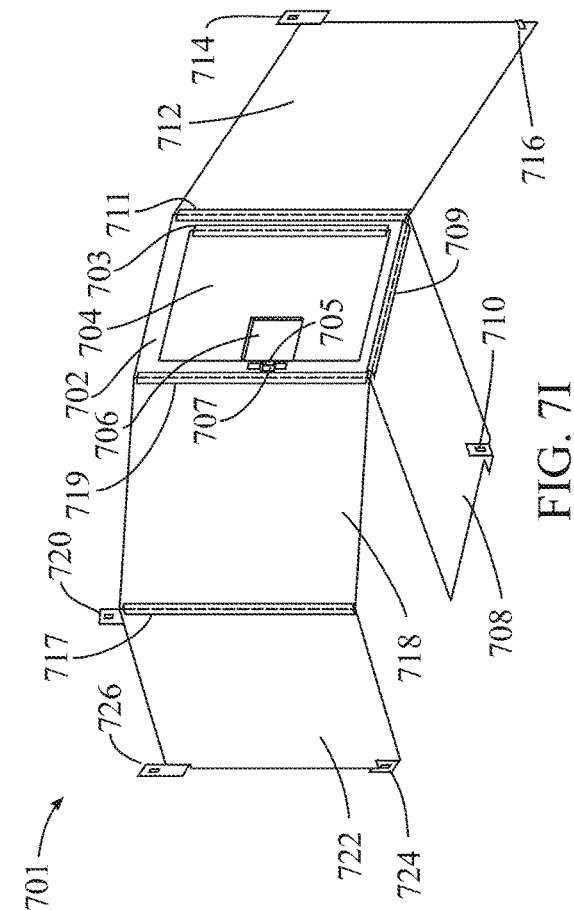
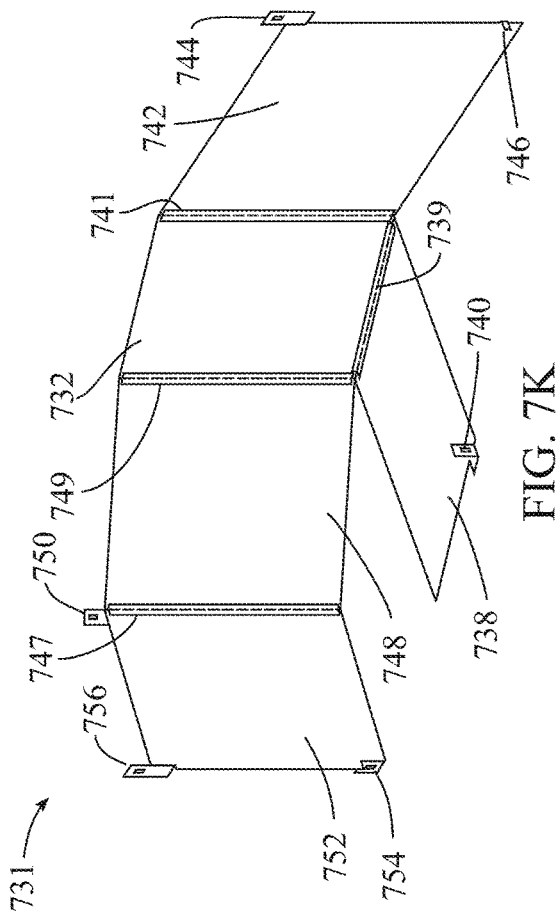
FIG. 7I
FIG. 7J
FIG. 7K
FIG. 7L

| Custody Event Table 900 | | | | | | | | |
|---|---|---|---|---|---|---|---|---|
| Event ID 904 | Event Type 906 | Transfer ID 908 | Event Time 910 | Release ID 912 | Receive ID 914 | Property ID 916 | Release Data 918 | Receive Data 920 |
| ... | ... | ... | ... | ... | ... | ... | ... | ... |
| Event ID | Event Type | Transfer ID | Event Time | Release ID | Receive ID | Property ID | Release Data | Receive Data |
| ... | ... | ... | ... | ... | ... | ... | ... | ... |
| Event ID | Event Type | Transfer ID | Event Time | Release ID | Receive ID | Property ID | Release Data | Receive Data |
| ... | ... | ... | ... | ... | ... | ... | ... | ... |
| Event ID | Event Type | Transfer ID | Event Time | Release ID | Receive ID | Property ID | Release Data | Receive Data |
| ... | ... | ... | ... | ... | ... | ... | ... | ... |

| Custody Transfer Table 930 | | | | | | | | | |
|---|---|---|---|---|---|---|---|---|---|
| Transfer ID 934 | Transfer Type 936 | Chain ID 938 | Transfer Time 940 | Release ID 942 | Receive ID 944 | Property ID 946 | Rel. Event Data 948 | Rec. Event Data 950 | Record Cert. 952 |
| ... | ... | ... | ... | ... | ... | ... | ... | ... | ... |
| Transfer ID | Event Type | Chain ID | Event Time | Release ID | Receive ID | Property ID | Rel. Event Data | Rec. Event Data | Record Cert |
| ... | ... | ... | ... | ... | ... | ... | ... | ... | ... |
| Transfer ID | Event Type | Chain ID | Event Time | Release ID | Receive ID | Property ID | Rel. Event Data | Rec. Event Data | Record Cert |
| ... | ... | ... | ... | ... | ... | ... | ... | ... | ... |
| Transfer ID | Event Type | Chain ID | Event Time | Release ID | Receive ID | Property ID | Rel. Event Data | Rec. Event Data | Record Cert |
| ... | ... | ... | ... | ... | ... | ... | ... | ... | ... |

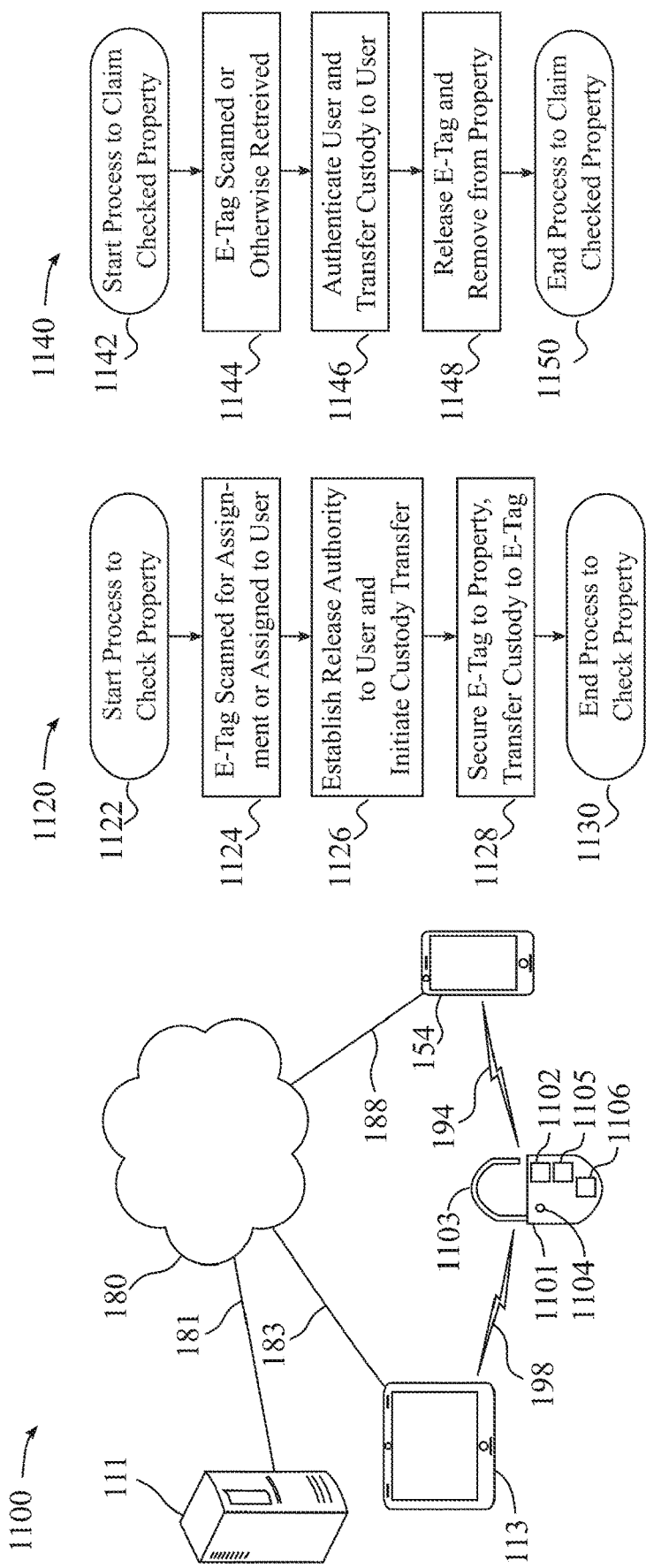

SECURE STORAGE SYSTEMS AND METHODS

CROSS-REFERENCE TO RELATED APPLICATIONS

This application is a continuation of, and claims the benefit of, copending U.S. patent application Ser. No. 16/446,594, filed Jun. 19, 2019 which is a continuation in part of, and claims the benefit of, U.S. patent application Ser. No. 16/389,841, filed Apr. 19, 2019 which is a continuation of, and claims the benefit of, U.S. patent application Ser. No. 16/117,583, filed Aug. 30, 2018, which claims the benefit of U.S. Provisional Application No. 62/552,423, filed Aug. 31, 2017, each of which is hereby incorporated by reference in its entirety herein.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

BACKGROUND

The subject matter of this disclosure generally relates to systems and methods for the securing and custody management of property in dedicated and shared service environments such as locker rental services, temporary storage of delivered goods and packages, and checked items such as luggage and coats and valeted vehicles.

There is a prevalent and increasing need for services which provide for temporary securing of property. The carrying of personal property or property of a custodial responsibility, combined with activities which make it mandatory or desirable to temporarily divest oneself of such property, or transfer custodial responsibility of such property is both commonplace and increasing. For example, the need for access to available secure lockers is increasing as safety policies place increasing restrictions on what can be brought into facilities and event venues. Prospective attendees at event venues in possession of disallowed items are routinely blocked from entry and are turned away to hopefully make suitable arrangements for secure temporary storage, and lacking timely success, may have to forgo the event all together. This leads to the significant inconveniencing of venue patrons causing significant loss of good will between venue proprietors and their patrons, thereby impacting venue popularity and revenues. Furthermore, the carrying of items which are optimally placed into temporary safekeeping is commonplace and increasing as people increasingly carry valuable items such as computer notebooks, electronic tablets, business and personal documents and effects throughout a busy day wherein they may visit facilities which increasingly restrict entry with one or more carried items, or the carrying individual simply wants to temporarily unburden themselves, such as at a facility, bar, restaurant or other such location, and not have to be concerned with maintaining vigilant watch against theft, damage or loss.

Traveling readily amplifies the need or desire for temporary safekeeping of carried items, other business related or personal items, or items with which they may have a custodial responsibility. Preferably such persons are able to locate temporary secure storage or other safekeeping services, such as secure rental lockers or some form of trustworthy checked storage services, such as hotel bag-check services, as they pursue their travel itinerary and activities. Of a similar nature to bag-check services are coat-check services. Also of similar nature are valet services, where control of a vehicle is temporarily transferred by transferring the keys for the vehicle to a valet attendant.

Another example of commonplace and increasing need for the temporary securing of property is that related to package delivery services, wherein a delivery service has custodial responsibility for property upon their taking possession thereof from a shipping entity until such time that it is acknowledged as received by a proper recipient. According to a Pitney Bowes Parcel Shipping Index Report, the growth of e-commerce across all business segments in 13 global markets resulted in the dramatic increase in parcel shipment volume of 48 percent over two years, where reported parcel volume of 44 billion parcels in 2014 grew to 65 billion in 2016. This dramatic increase in package delivery has led to a dramatic increase in theft of packages. According to an article published by USA Today, "Were your Amazon packages stolen? Porch pirates run rampant this holiday season", Dec. 13, 2018, 30 percent of Americans say they've experienced such theft themselves and the Denver Police Department, which tracks package theft, has seen incidents rise every year since 2015. Additionally, with this increasing trend in package delivery, persons traveling are commonly and increasingly in situations where they preferably can receive and access delivered items at locations away from home. For example, someone may wish to ideally have a package delivery redirected and conveniently accessible, such as in a temporary secure storage locker, while traveling en route.

BRIEF SUMMARY OF THE INVENTION

According to some possible and illustrative embodiments of the disclosed subject matter, secure storage platforms and secure temporary storage applications, are disclosed. Such secure temporary storage applications may comprise, but are not limited to: secure locker systems; secure locker systems comprising emergency access; secure locker systems comprising collapsible lockable compartments; secure storage systems comprising chain of custody services and authentication services thereof; secure redirected and dispatch delivery comprising chain of custody services and secure storage; and secure property claim check and car valet systems.

Secure Locker System Comprising a Secure Storage Platform

A secure storage platform in conjunction with a secure locker system and method may comprise a server based system comprising one or more servers, software services and data services, and may be a cloud based system. A secure locker system may further comprise a plurality of lockable compartments. Lockable compartments comprise a lockable door and a controllable electromechanical lock, which may also be referred to herein simply as a lock. Electromechanical locks may be intelligent locks comprising a lock access controller, or may be simple locks controlled by a lock controller board comprising a lock access controller. Lockable compartments may be organized in groupings in varying numbers of units and of varying styles of construction and configuration, such as varying unit size and varying style of lock. A plurality of lockable compartments organized in a grouping may be referred to as a locker bank. Generally, locker banks may be located in various geographic locations and do not require a particular geographic relationship to one another or to a server based system. In an embodiment a locker bank may additionally comprise a kiosk. A kiosk may comprise a touchscreen, a keypad and card reader.

A secure locker system may also comprise one or more portable wireless devices useable by users for interacting with the secure locker system to rent and access a lockable compartment or access an otherwise lockable compartment assigned thereto, or perform other related interactions such as search for available lockable compartments, terminate a locker rental and the like. Portable wireless devices can be smartphones, and may also be smartwatches, cell phones, tablets, laptops and other devices which provide a user interface and can be communicatively connected to the server based system, and lock access controllers of locks of lockable compartments. Portable wireless devices may comprise at least one type of wireless communications capability, such as, a cellular internet communications, herein also referred to as a wide area network (WAN) capability; a short range communications capability, such as Bluetooth communications; and a wireless local area network (WLAN) capability, such as an IEEE 802.11 based WLAN (Wi-Fi); wherein, many devices, such as many smartphone portable wireless devices, may comprise all three of a WAN, short range and WLAN communications.

A secure locker system may additionally comprise one or more operator devices, such as a computer or a tablet, which may be used by personnel engaged in managing the operations of the secure locker system to perform such functions as review the volume of locker rentals over time, review advanced rental bookings, review the current number of available lockers, review the anticipated or predicted shortages of available lockers, review actual and projected rental revenues, review and report issues, review and issue maintenance requests, and the like. Operator devices may additionally be laptop computers, smartphones and other portable electronic devices, and be used for locker installation and maintenance operations of lockable compartments, locker bank installations, customer assistance, and the like. Operator devices may comprise wireless communications capability, such as, a cellular internet (WAN) communications capability, a wireless local area network (WLAN) capability and a short range communications capability, such as Bluetooth communications, wherein many devices, such as many smartphone based operator devices, may comprise all three of a WAN, WLAN and short range communications.

A challenge code generator of a server based system of a secure locker system may enable a portable wireless device for secure access to a lockable compartment by providing the portable wireless device with a single use access authentication code for use as a challenge code. A single use access authentication challenge code is applicable to a single access transaction. A single use access authentication code is also independently generated by a verification code generator of a lock access controller for a lock to be accessed for use as a corresponding verification code. The use of access authentication codes that may only be used once ensures that a disclosure and/or malicious capture of any code limits the exposure of unauthorized access to a single access event of a specific lockable compartment. In an embodiment, a challenge code may be generated and provided by a server based system to a requesting portable wireless device when the requesting portable wireless device is sufficiently close enough to establish short range communications with a lock access controller of a lockable compartment to be accessed. This limits the useful lifetime of an access authentication code, since the user of the requesting portable wireless device is in close proximity and presumably readying to open the lockable compartment, and the code may therefore be used as soon as it is received by the portable wireless device. In an embodiment, a challenge code and independently generated verification code may be generated upon the initiation of an access request presented to a lock access controller, upon which a time window, such as a one or five second time window, for use of the verification and challenge codes may be established, wherein if the codes are not used in conjunction with an access event within the time window, the codes expire and are no longer useable.

A secure protocol may be established for independent generation of single use access authentication codes by a server based system and lock access controllers for each lock of a secure locker system. A secure protocol may use encryption, such as, the Advanced Encryption Standard (AES) published by the National Institute of Standards and Technology (NIST). Code derivation encryption keys, also referred to herein as code derivation keys or derivation keys, may be established such that they are solely known to a server based system and a lock access controller which may reside within a lock or a controller board controlling the lock. When a lock is to be made operable in secure locker system, it can be initialized with a code derivation key and an input code which reside in each of: a) the verification code generator of the lock access controller for use in generating verification codes, and b) a lock access table maintained by the challenge code generator of the server based system for use in generating challenge codes. Upon a first access of a newly initialized lock, a first generated single use access authentication code is generated by the server based system for use as a challenge code, and by the lock access controller for use as a verification code, by encrypting the input code with the code derivation key independently comprised therein. A second access code and further subsequent access codes are generated by encrypting the last generated access code as the input code with the code derivation key.

An operator device and a server based system can exchange public keys of respectively comprised public/private key pairs and can also use digital certificates issued from trusted third party certificate authorities to mutually authenticate each other in order to engage in a lock initialization process. The public keys may be used to securely exchange independently generated derivation key component values and input code component values, using an asymmetric encryption such as the Rivest-Shammir-Adleman (RSA) asymmetric encryption. The component values may then be assembled within an operator device (and loaded into a lock access controller therefrom) and a server based system to create a shared code derivation key and a shared input code needed to complete an initialization process. In an embodiment, a lock access controller may comprise asymmetric encryption and an operator device may provide the lock access controller with a server based system public key, such that a lock derivation key component and a lock input code component may be generated and encrypted within the lock access controller. In such an embodiment, an unencrypted lock derivation key component and an unencrypted lock input code component need not ever reside outside of the lock access controller. Furthermore, the assembly of component values needed for the derivation key and the input code comprised by the lock access controller may be performed therein.

An operator device may initialize a lock by first putting the lock access controller controlling the lock into a service mode by presenting to the lock access controller a valid challenge code and valid secure service mode token for the lock provided by the server based system. To create a secure service mode token, the server based system can encrypt a value that is shared between the server based system and the lock access controller other than the input code. A sequence number may be an additional shared value between a lock access controller and a server based system and may be used to maintain a synchronization of code generation cycles. Additionally, a sequence number can used as a service mode token and be encrypted using a code derivation key and thereby be used as a secure service mode token used to establish a service mode. A server based system may restrict provision of secure service mode tokens to authenticated operator devices to prevent a fraudulent use of user portable wireless devices (which may have access to challenge codes) to fraudulently establish a service mode of a lock access controller. When a lock is first initialized for use in a secure locker system, the derivation key, input code and sequence number used to put the lock access controller controlling the lock into service mode may be default values or initial values established during manufacturing of the lock access controller.

Upon successful entry into service mode, the initialization process generates a new shared secret derivation key and a new shared secret input code by the independent generation, encryption and secure mutual exchange of encrypted derivation key components and encrypted input code components by the server based system and the operator device or the lock access controller. Once components are exchanged, the received encrypted components may be decrypted and combined with the locally generated components to assemble the new shared code derivation key and the new shared input code. By using independently generated and mutually exchanged derivation key components and input code components which are passed under respective public/private key pairs, a considerable level of additional security protection is achieved beyond security which may be achieved through a sending of a complete derivation key or input code using only transport level security protocols, such as TLS, to secure the key or code. Namely, both secret private keys and the cypher text of all component parts must be respectively obtained and intercepted in order to assemble the derivation key and input code. Furthermore, an additional measure of device authentication is realized as both the server based system and the operator device must exercise a private key known only to them to decrypt a received component in order for it to be put into use.

In an embodiment, a lockable compartment may comprise a keypad, and a user having a current rental session, or otherwise having an assigned use of the lockable compartment may wish to store their portable wireless device therein. The user may submit a request to assign a user PIN (request to assign PIN) and select a PIN on their portable wireless device. An assign user pin submission by a portable wireless device with the selected PIN in combination with a successful challenge code may then, for the duration of the present rental session or assignment, cause the lock access controller for the lock of the lockable compartment to accept a correct selected PIN entered via the keypad and open the lock in response thereof. If a user suspects their selected PIN may have been compromised, they can submit another assign user PIN request and select another PIN on their portable wireless device, or submit a request to cancel and deactivate their current access PIN, should they determine they no longer want or need the capability of access via the keypad. Upon an access in conjunction with a termination of a rental session or assignment, the server based system may cancel and deactivate the access PIN.

In an embodiment, a locker bank may comprise a kiosk which may comprise a touchscreen user interface, an electronic payment keypad, which may accept secure entry of a debit card PIN number, and a chip and magnetic stripe card reader. The kiosk may be used by users to rent and access lockable compartments. The kiosk may be used when a user does not have a portable wireless device or their portable wireless device is otherwise not available, for example, the battery is fully depleted. A kiosk can communicate with a server based system and receive a challenge code for access to a lockable compartment and can interact with lock access controllers in a similar fashion as a portable wireless device. A user having a user account with a secure locker system can use a kiosk to log into their account to facilitate the rental process, or can otherwise use the system as a guest user. A user having a current rental session with a lockable compartment can access it using a portable wireless device or kiosk by authenticating themselves to a server based system by having signed into their user account of a secure locker system application, and selecting an open locker selection. Alternatively, a user having a user PIN, previously established through an assign user PIN command, may enter the PIN into the kiosk or a keypad of their rented or assigned lockable compartment, should it be so equipped.

Access events may be logged and recorded in a server based system of a secure locker system. Access events may comprise interactions with a server based system, portable wireless devices, operator devices and lock access controllers of intelligent locks or lock access controllers of lock controller boards controlling simple locks. Lockable compartment access records can be processed from one or more access events and comprise a complete account of events for an access of a lockable compartment, or failed attempt thereof.

Secure Locker System Rental and Access Application

A secure locker system may comprise a rental and access application for download onto portable wireless devices and thereby permit users to interact with the secure locker system to rent and access a lockable compartment or access an otherwise assigned lockable compartment, and perform other related interactions such as search for available lockable compartments, review current rentals, terminate a locker rental, and the like. Lockable compartments may comprise a barcode, such as a quick response barcode, or QR Code, such that users may use their portable wireless devices to quickly access information from a server based system related to the rental of a lockable compartment, download a rental application therefrom if not already loaded, and establish an account therewith if not already established. If a user already has the application downloaded, the application may indicate an availability status for the scanned lockable compartment, or a nearby lockable compartment available for rental. Once logged into their account, the user can be presented with a home view, where the user can choose from a plurality of actions, such as, a select/scan a locker action which may present a rental screen, map view action which may present screens to locate a locker, current rentals action which may present a screen of their current rentals, transaction history action which may present a review of their transaction history, account settings action which may present screens to review and update account settings and a logout action which may exit the application.

Similar to a secure locker system rental and access application usable by users to interact with a secure locker system, a secure locker system operations application can be provided and be usable by operators of a secure locker system to interact therewith. A secure locker operations application can be downloaded onto an operator device and be associated with an operator account comprised by server based system. An operator can be authenticated by logging into their account similar to a user logging into an account associated with a secure locker rental and access application. A secure locker operations application can be used to initialize locks and process maintenance and service requests, among other operations related actions.

Secure Locker System Comprising Emergency Access

An operator of a secure locker system may operate lockable compartments located at a plurality of locations and venues, and may be associated with a plurality of location operators and venue proprietors. A secure locker system operator may choose to additionally provide a localized redundancy of functions and services remotely provided by a server based system. In this manner, should the remotely provided functions and services of the server based system become unavailable to operate lockable compartments of a location or venue, a local server based emergency access appliance or system may be enabled as failover services such that patrons of affected lockable compartments have continued use and access thereof. In an embodiment, a secure locker system may additionally comprise one or more appliances or server based emergency access systems, each of which may comprise one or more servers, software services and data services. Each appliance or server based emergency access system, also referred to as an emergency access system, may be located at or in proximity of a location or venue comprising a secure locker operation, and may be associated therewith and provide uninterrupted locker access operations in the event that the server based system is not functional, is not accessible or is otherwise unavailable to support access of lockable compartments associated therewith.

Emergency challenge codes and emergency verification codes can be used in an emergency lock access process, and can be generated using emergency access input codes and emergency access derivation keys, wherein an emergency challenge code generator of an emergency access system generates an emergency challenge code and a verification code generator of a lock access controller generates an emergency verification code. When locks supported by both a server based system and an emergency access system are initialized for use in a secure locker system, both sets of keys and input codes (one set for use with a server based system and one set for use with an emergency access system) can be established in a combined initialization process. An operator device initializing locks in a combined initialization process exchanges public keys of respective public/private key pairs with both a server based system and an emergency access system such that the component parts for each set of derivation keys and input codes can be securely exchanged. An emergency sequence number is an additional shared value comprised by a lock access controller and an emergency access system, and may be used to maintain a synchronization of emergency code generation cycles therebetween.

In normal operations, when a server based system is available, active rental session records, also called active rental contracts for lockable compartments also serviced by an emergency access system are communicated by the server based system to the appropriate emergency access system. As such, should a server based system become unavailable, emergency based systems can continue to provide access per the currently active rental contracts within their system. When a portable wireless device establishes a rental contract for a lockable compartment, a server based system can check to see if the contracted compartment is associated with an emergency access system and, if it is, send a record of the contract thereto. Additionally, the server based system can send failover URLs for API services of the associated emergency access system to the portable wireless device and a secure locker app running thereon upon entering into the rental contract. Should the API services of the server based system then become unavailable, the portable wireless device and secure locker system rental and access app running thereon, may then utilize the failover URLs for API services of the associated emergency access system for emergency access transactions until such time that the server based system becomes available.

Each emergency access system can maintain emergency access event records and emergency lockable compartment access records. When the server based system returns to an available status, records from an emergency access system can be forwarded thereto. Any deferred processing, such as submission of payment transactions, that was deferred until the server based system became available can then be processed. A server based system can audit an emergency access system by processing records from the emergency access system, and can also request records comprising emergency sequence numbers for each lock within the lock emergency access system to validate consistency between reported emergency access records and lock emergency sequence numbers and thereby validate the completeness of reported records and activity. Emergency access systems may be implemented such that they require an administrator of the secure locker system to enable their use. In this way and in addition to audit procedures, an operator of a secure locker system can ensure that emergency access is only used when it is appropriate.

While a primary benefit of emergency access systems is the continued servicing of existing rental contracts despite the unavailability of a server based system, in an embodiment, emergency access systems may additionally provide services to enable the initiation of new rental contracts despite the unavailability of a server based system. When a server based system returns to an available status, rental contracts initiated within the emergency access system can be forwarded for recording by the server based system and any further handling or required processing thereof, such as ongoing handling of active rental contracts, closure of rental contracts and submission of payment transactions that were deferred until the server based system became available.

In an embodiment, an emergency access device, similar to an operator device can be provided. An emergency access device may have limited functionality in comparison to an operator device. For example, an emergency access device may not be capable of initializing a lock. A primary use of an emergency access device may be to access a lockable compartment when prior attempts using a user's portable wireless device have failed. An operator of an emergency access device may be required to receive and enter a permission code from a secure locker system operator to enable an emergency access command to access a lockable compartment using the emergency access system. The provision of a permission code for such emergency access can be restricted and require procedures to ensure only a legitimate user is provided such emergency access.

Secure Locker System with Collapsible Lockable Compartments and Secure Storage Platform Demand for secure temporary storage can be closely related to events and can vary depending on factors such as weather, the day of the week, time of day, event location, event popularity, and many other factors. For example, a sporting event on a weekday, starting near the end of the workday, and near a busy metropolitan area will likely be attended by many people wanting to store business and other workday related items. Other events are temporary in nature and permanent or semi-permanent secure storage lockers may not be practical. Given a fluctuation in demand and a temporary nature of many events, secure storage lockers that may be easily and compactly transported to a location when needed, and easily set up and taken down to be once again transported can be desirable.

In an embodiment, secure locker systems can be configured for use with, and comprise a portable, collapsible locker system comprising a collapsible and foldable lockable compartment and a collapsible and foldable base on which one or more collapsible lockable compartments may be placed in a stacked manner thereby forming a vertical locker stack assembly. Vertical stack assemblies may be situated with other vertical stacks to produce a locker bank. The collapsible lockable compartments and collapsible bases may be easily and compactly transported to a location when needed, and easily set up and taken down to be once again transported in order to address temporary and fluctuating demands associated with temporary secure storage. Furthermore, temporary secure storage arrangements can be flexibly configured to comprise individual lockers, stack assemblies and locker banks.

Collapsible lockers and bases may comprise fastening tabs and fastening pins and when assembled in adjacent rows and columns may form joining points wherein fastening tabs of three lockers (or lockers and bases) of adjacent rows and columns may be joined together with a common fastening pin, and in doing so result in two adjacent rows and two adjacent columns being secured together. Each locker of an upper row of lockers may be joined with a top panel which may be secured thereto by passing a locking bar through fastening tabs of joining points wherein a locking bar may comprise an end formed to prevent passage of the bar fully through an end joining point, and hole which may pass through a joining point of another end. Once the hole of the locking bar has passed through the other end joining point, a lock hasp may be passed therethrough and a lock secured thereto, such that the locking bar may be locked in place, thereby securing the locker bank. The locking bar may additionally be passed through brackets mounted to a supporting wall in order to secure the locker bank to a supporting wall.

Chain of Custody with Intermediary Secure Storage Transfer Entities

In a chain of custody, each entity acting in the chain from origination to final receipt, including each intermediary, transfers control of property under custody as appropriate with their position in the chain. Property transfers between chain origination and chain termination, where an intended recipient receives custody of property, may be captured and securely recorded in order to securely document and a chain of custody, wherein each participating entity is identified and authenticated, and their participation accurately captured and securely recorded.

Embodiments of secure locker systems may comprise a chain of custody service. A chain of custody service may be implemented to provide a varied scope of coverage. An embodiment may comprise a chain of custody service for transfers comprising secure temporary storage as a participating entity. When a secure lockable compartment as disclosed herein is used as an intermediary custody transfer entity, it can be identified and authenticated, and participate in a transfer that can be accurately captured and securely recorded. Furthermore, when a secure lockable compartment is used as an intermediary custody transfer entity, it may be particularly beneficial to accurately capture and securely record the transfer, since without recorded documentation of a transfer, disputes arising from a property loss may not be fully investigated. As such, an operator of a secure locker system may wish to offer a secure storage platform comprising a secure chain of custody service. In an embodiment, a secure locker system may comprise a secure chain of custody service for transfers where a secure lockable compartment is used as an intermediary custody transfer entity. In an embodiment, a secure locker system may comprise a secure chain of custody service for some or all transfers in a chain of custody from originating entity to end-recipient. In an embodiment, an originating entity or other entities in a chain of custody may specify a release authority, wherein a release authority is a specification which may specify requirements and actions necessary to authorize a custodian to release property of custody in a custody transfer transaction, and transfer release authority obligations to a receiving entity. As such, where secure storage is a participating entity in a custody transfer transaction, a release authority may specify obligations of a storage platform and lockable compartment thereof, when receiving custody, and requirements and actions for a storage platform to execute in releasing custody from a lockable compartment to a receiving entity. Release authority specifications may comprise, but are not limited to, mechanisms for authentication of a receiving entity, such as specifying a secure locker access application and account by which to authenticate a receiving party; mechanisms for providing an access token to a receiving entity, such as specifying an email address or phone number to which to send an access token; requiring one or more release mechanisms; and requiring multifactor authentication.

A secure locker system with secure storage platform as disclosed herein may provide secure lockable compartments that may be identified by a lock ID (and location ID and locker ID) and require a cryptographically secure single use access authentication code for access. As such, the provision of a single use access authentication code to an authenticated entity, and the use by that authenticated entity of that single use access authentication code to access a lockable compartment in order to execute a custody transfer of property, can be accurately captured.

A secure storage platform may comprise a chain of custody service providing a custody transfer reporting service. In an embodiment, a chain of custody service of a secure storage platform may distribute certified custody transfer records, and further comprise a custody authentication ledger service, whereby an authenticity and integrity of a certified transfer record may be verified using a certificate retrieved from the authentication ledger. A ledger entry comprising an identifier of the certified transfer record, also referred to as a transfer ID, and a certificate thereof, may be created and written to a custody transfer authentication ledger. The certified transfer record may be distributed to interested parties, such as parties of the subject transfer or a previous or planned entity such as an originator or planned recipient. A secure chain of custody authentication service can then be queried by holders of certified transfer records to verify the authenticity and integrity thereof.

In an embodiment, an authentication ledger can be a blockchain ledger and may be maintained by multiple entities, such as entities having regular participation in chain of custody transfers, for example, package delivery services, leading online retailers and a secure locker system operator. Multiple participating entities can operate blockchain nodes may enforce a consensus agreement therefrom as a requirement for adding a block of ledger entries to the blockchain. A blockchain so maintained can be immutable and certificates thereon in the form of ledger entries can be relied on for validating certified chain of custody records accordingly. Furthermore, a blockchain so maintained retains a consensus capability and comprises redundancy and continued availability when greater than 50% of the nodes are operable and available.

A custody transfer record may be certified by generating and associating a record certificate to the record. A record certificate can be a cryptographic hash of record fields comprised by the record (other than the certificate itself), such as an SHA-3 compliant hash, as published by the National Institute of Standards and Technology (NIST) in Federal Information Processing Standards Publication 202 (FIPS PUB 202), SHA-3 Standard: Permutation-Based Hash and Extendable-Output Functions, August 2015. A cryptographic hash creates a digital fingerprint of the record fields for use as a certificate for inclusion in a record certification field. Any alteration of the record fields results in an unpredictable change in a calculated certificate, and the potential to modify a record and preserve a certificate value is highly improbable. As such, a record may be authenticated using a certificate obtained from the authentication ledger for a subsequent calculation of a hash of the custody transfer record, wherein should a matching hash result, the record is determined to be authentic and the integrity of the information therein is verified.

In conjunction with a custody transfer to a lockable compartment, such as by a package delivery courier, an access request may be made using a portable wireless device to open the lockable compartment, wherein a verification code generator of a lock access controller generates a verification code and a challenge code generator of a server based system generates a challenge code and sends it to the portable wireless device. The portable wireless device in turn sends an open lock command and the challenge code to the lock access controller, and if the codes match (and an access timer is still active, as will be described later), the lock is opened and access to the lockable compartment is provided. Upon successful access, the portable wireless device may relay a release authority to a server based system, wherein the release authority may specify the generation of a random value for use as an access token by an intended end recipient, and an email address to which a notification comprising the token is to be sent. In such a case, the server based system then encrypts the random access token using a derivation key for the lock of the lockable compartment and sends it in an open-on-token command to the lock. In a subsequent custody transfer, the end-recipient may access the lockable compartment with the proper entry of the access token in a keypad comprised by the lockable compartment.

In an embodiment, a lockable compartment may comprise a door status sensor, such that an opening and closing of a lockable compartment door can be observed by a lock access controller. Additional access events associated with a change of door status in a custody transfer and their time stamps can be reported to a server based system. In an embodiment, a lockable compartment may comprise a camera system comprising an illumination source, such that the contents of a lockable compartment may be recorded prior to an opening of a lock thereof and after a closing of the door, and resulting images and their time stamps can be reported to a server based system. A courier transferring custody of a package comprising a readable code comprising a tracking number can be instructed to orient the package in a lockable compartment comprising a camera such that the readable code indicating a package tracking number is visible to the camera system will be visible in an image captured after the door is closed. In an embodiment, visual assistance showing a current view of a camera system can be displayed on a portable wireless device of a courier to assist in a satisfactory placement of a package. A chain of custody service of a secure storage platform may create and distribute a certified transfer record comprising a detailed account of an associated custody transfer comprising images documenting a transferred property. A ledger entry comprising a transfer ID and a certificate for the certified transfer record can be created and written to a custody authentication ledger maintained by a chain of custody authentication service of the secure storage platform.

Post-Delivery Redirected Delivery, En Route Delivery and Other Flexible Delivery and Dispatch Services In various embodiments, a secure locker system comprising chain of custody services can provide various secure delivery and dispatch services comprising post-delivery redirected delivery, en route and impromptu delivery and dispatch services and other flexible delivery and dispatch services. For example, an intended recipient may be notified that a package has been delivered to a lockable compartment at their condominium residence while they are away from home. Yet they would benefit from receiving the package prior to their planned return home. In an embodiment, they can authorize and schedule a transfer of custody to a delivery service and have the package securely collected from the lockable compartment and delivered to their present location, planned future location or securely delivered to a lockable compartment in a convenient proximity thereto. As such, a user schedules a post-delivery redirected delivery, wherein the user engages a service and updates or otherwise establishes a release authority with a secure storage platform which specifies the engaged service as a receiving entity for a transfer of custody from the secure lockable compartment comprising the package, and further specifies the user as the end-recipient, thereby permitting the engaged service to complete the post-delivery redirected delivery.

In an embodiment, an intended recipient may be traveling and may have a package delivery synchronized with their travel itinerary such that delivery is conveniently made to a secure lockable compartment accessible en route. As such, a user engages a delivery service, and if the package has yet to ship from an originator, the user creates a new release authority which specifies the engaged service as a receiving entity for a transfer of custody from the originator, the user as the end-recipient of an en route delivery, and an en route delivery location. If the package has already shipped, a current release authority is updated to permit the current courier to change the delivery location to an en route location with the user as the end-recipient. Regardless of which case is used, namely, a new or updated release authority, the release authority permits the engaged service to make an en route delivery.

In an embodiment, a person may dispatch a package (in a planned dispatch) for delivery while traveling by accessing a lockable compartment, transferring custody of the package thereto and scheduling a transfer of custody to a delivery service. In an embodiment, a person may have temporarily secured property in a lockable compartment, such as in a lockable compartment at a sporting event or at a concert venue, and later have their items delivered to them (in an impromptu dispatch) rather than return to the lockable compartment themselves. For an impromptu dispatch delivery, the user engages a service for the dispatch delivery and creates or updates a release authority permitting the lockable compartment to release custody to a specified dispatch courier for delivery to a recipient specified by and which typically is the user. For a planned dispatch delivery, custody is transferred from the user as an originator to a lockable compartment and a release authority is created permitting the lockable compartment to release custody to a specified dispatch courier for delivery to a recipient specified by and which may be the user. Regardless of which case is used, namely, a newly created or updated release authority, the release authority permits the engaged service to collect the property from the lockable compartment and make the dispatch delivery.

Secure Claim Check and Valet Services

In an embodiment, a secure storage platform can secure property in a claim check based service that may be supervised by a proximate attending operation, such as hotel bag-check services. Of a similar nature to bag-check services are coat-check services. Also of similar nature are valet services, where control of a vehicle is temporarily transferred by transferring the keys for the vehicle to a valet attendant. In a claim check application and in a vehicle valet service comprising a secure storage platform and chain of custody service, a transfer of custody of checked property and keys (and indirectly valeted vehicles), and a return transfer thereof, can be securely captured and recorded. In an embodiment, theft of a checked or valeted item such as a checked bag of luggage or a set of car keys (and associated vehicle) can be detected and may be tracked for a potential recovery thereof.

A secure storage platform comprising a claim check service may comprise a plurality of electronic lockable tags, also referred to as e-tags. Generally, a claim check service may comprise a quantity of e-tags commensurate for an upper potential quantity of concurrently checked items. E-tags may comprise a lock access controller comprising a verification code generator, code derivation key and last access code for generating a verification code for comparison to a received challenge code, whereupon a matching verification code and challenge code, the lock access controller opens a lock thereon. Dissimilar to a lockable compartment application, e-tags may be secured to property when assigned custody thereof, rather than securing access to property as in the case of lockable compartment. A user of a portable wireless device comprising a secure storage application or an operator of an operator device may scan a readable code of an e-tag when checking property with the claim check service. For example, a user checking a bag may be presented with an e-tag and scan a code thereon which then assigns the e-tag for use by the user to check property thereof. Alternatively, an operator can register the user within the system using an operator device and scan the code to assign the e-tag to the user. In an alternative embodiment, an alternative method for assignment can be used, such as a claim check operator can reference a user account, such as a conference registration or a hotel registration and link the assignment thereto. Alternatively, a server based system may make a selection and assignment, and flash an indicator, such as an LED indicator comprised by the e-tag to alert an operator of the assignment. After an e-tag is assigned, a release authority specifying a release to the user as an end-recipient is created and a custody transfer is initiated. A device that was used in the assignment of the e-tag, such as an operator device or user portable wireless device can connect to a server based system and a lock access controller of the e-tag to respectively obtain and present a challenge code for comparison to an independently generated verification code and open the e-tag lock hasp. The e-tag is secured to the property being checked by closing a lock hasp thereof attaching it to a feature of the property such that it is secured thereto. For example, the hasp may be closed such that the e-tag is secured to a handle, or feature thereof, of a luggage bag. Or in the case of a valet service, the hasp may be closed such that the e-tag is secured to a key fob remote or key to a vehicle. Once an e-tag is secured to property, custody may be transferred to the e-tag, wherein a releasing entity is the user and the receiving entity is the e-tag.

To claim checked property, an e-tag may be scanned by a user of a portable wireless device claiming their property checked with the claim check service using a secure storage app and account recognized by a server based system and running on their portable wireless device. Alternatively the user may select a function of the app to show currently checked items to retrieve the e-tag based claim check. If an operator device or server based system was used to assign the e-tag, it may alternatively be used to scan or otherwise retrieve the e-tag after the identity of the user is verified by an operator of the checked storage service. Once an e-tag is determined to be the e-tag with custody of the property of interest, server based system, via portable wireless device or the operator device may indicate the e-tag by actuating an indicator. The user is authenticated, either through use of their device and secure storage app and account running thereon, or through identity information entered or acknowledged by the operator on an operator device. Upon authentication, custody may transferred back to the user per a release authority, wherein the releasing entity is the e-tag and the receiving entity is the user. After custody has been transferred to the user, the e-tag lock may be opened using a challenge code generated by a challenge code generator of a server based system and communicated via a user or operator device to a lock access controller of the e-tag and the e-tag is removed from the checked property.

In an embodiment, an e-tag may further comprise a tracking device comprising a location or trackable feature, such as a global positioning system (GPS) capability, and long range communications capability, such as a low-power wide-area network (LPWAN), like ultra-narrowband (UNB). The tracking device may periodically report its current position to a receiver which in turn reports the location of the e-tag to the server based system. As such, if property in custody of, and to which an e-tag is attached, is stolen, it may be tracked and potentially recovered. Furthermore, a permitted location or proximate location for an e-tag may be established, such that if an e-tag reports a violating location, an alert can be issued by a server based system indicating a potential theft of the property in custody of the e-tag.

In an embodiment, a lower cost implementation comprising simple non-electronic printed tags (non-e-tags) having readable codes can be used, wherein the readable codes are read by portable wireless devices to assign non-e-tags and transfer custody thereto and therefrom.

The possible and illustrative embodiments disclosed herein should not be construed as an exhaustive list. Rather the various embodiments presented serve to illustrate only some of the various ways to practice the invention and many additional combinations of features and configurations are possible within the scope of the invention disclosed herein.

BRIEF DESCRIPTION OF THE SEVERAL VIEWS OF THE DRAWINGS

The accompanying drawings, which are included to provide a further understanding of the disclosed subject matter, are incorporated in and constitute a part of this specification. The drawings also depict possible and illustrative embodiments of the disclosed subject matter and together with the detailed description serve to explain the principles of the disclosed subject matter.

FIG. 2A is an example illustration depicting a lock access table.

FIG. 2B is an example illustration depicting an access event table.

FIG. 2C is an example illustration depicting a lockable compartment access table.

FIG. 6E is an example illustration depicting a rent screen of a secure locker rental application.

FIG. 6F is an example illustration depicting a rental confirmation screen of a secure locker rental application.

FIG. 7A is an example illustration depicting an unfolded collapsible and foldable lockable compartment.

FIG. 7B is an example illustration depicting a partially folded collapsible and foldable lockable compartment.

FIG. 7C is an example illustration depicting a folded collapsible and foldable lockable compartment.

FIG. 7I is an example illustration depicting a partially folded collapsible and foldable lockable compartment comprising an additional fastening tab.

FIG. 7J is an example illustration depicting a folded collapsible and foldable lockable compartment comprising an additional fastening tab.

FIG. 7K is an example illustration depicting a partially folded collapsible and foldable base comprising an additional fastening tab.

FIG. 7L is an example illustration depicting a folded collapsible and foldable base comprising an additional fastening tab.

FIG. 9A is an example illustration depicting a custody event table.

FIG. 9B is an example illustration depicting a custody transfer table.

FIG. 11A is an example illustration of a secure storage system comprising a claim check service.

FIG. 11B is an example illustration of a process to check property using the system of FIG. 11A.

FIG. 11C is an example illustration of a process to claim checked property using the system of FIG. 11A.

DETAILED DESCRIPTION OF THE INVENTION

Figure 1A:
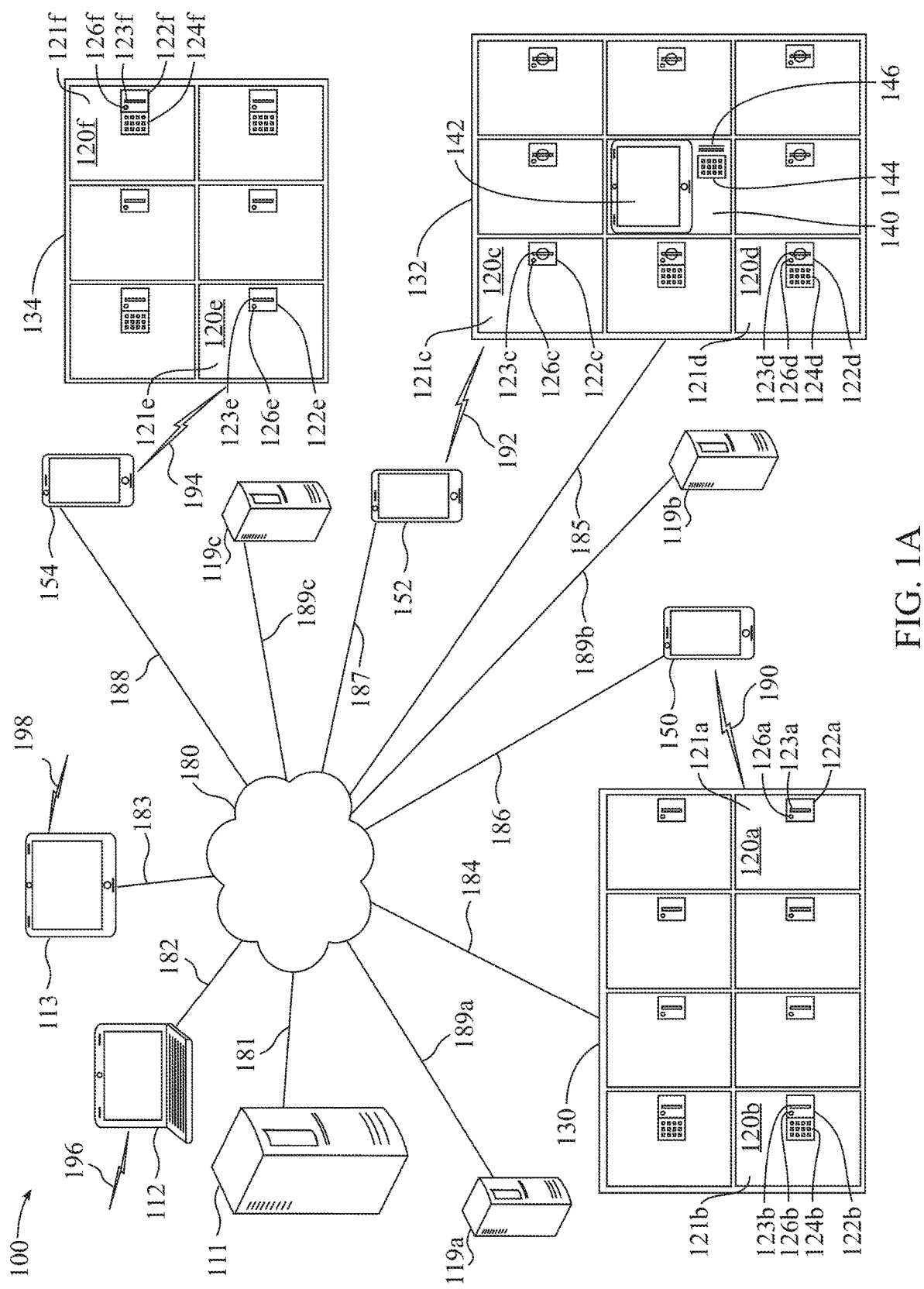
FIG. 1A is an example illustration depicting a system diagram of an example embodiment of a secure locker system.

Detailed example embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive.

The following detailed example embodiments refer to the accompanying drawings. The same reference number may appear in multiple drawings and when appearing in multiple drawings will identify the same or similar elements. For brevity, a reference number and its referenced element will be disclosed in accompanying text herein and in relation to a first appearance in the drawings, but may not be explicitly referred to in accompanying text again when appearing in subsequent drawings.

This disclosure provides a detailed description of secure storage platforms and their application in secure temporary property storage applications. Such secure temporary property storage applications may comprise, but are not limited to: secure locker systems; secure locker systems comprising emergency access; secure locker systems comprising collapsible lockable compartments; secure storage systems comprising chain of custody management, recording and authentication; redirected delivery including post-delivery redirected delivery, en route delivery and dispatch delivery services comprising chain of custody services; and secure property claim check and car valet systems. A secure storage platform will initially be disclosed in conjunction with an example illustration of a secure locker system and method.

Secure Locker System Comprising a Secure Storage Platform

FIG. 1A is an example illustration depicting a system diagram of an example embodiment of a secure locker system 100. Secure locker system 100 comprises a server based system 111 comprising one or more servers, software services and data services, and may be a cloud based system. Server based system 111 also comprises a communications link 181 to a communications network 180 and is thereby accessible by a plurality of devices and systems. In an embodiment, secure locker system 100 may additionally comprise one or more server based emergency access systems 119a, 119b and 119c, each of which may comprise one or more servers, software services and data services; may be a cloud based system or may be located at or in proximity of a venue comprising a secure locker operation; and may provide uninterrupted locker access operations in the event that server based system 111 is not functional, not accessible or otherwise unavailable to support needed services. Server based emergency access systems 119a, 119b and 119c further comprise communications links 189a, 189b and 189c, respectively, to communications network 180 and are thereby accessible by a plurality of devices and systems.

Secure locker system 100 further comprises a plurality of lockable compartments, such as lockable compartments 120a, 120b, 120c, 120d, 120e and 120f (120a-120f), which may also be referred to herein as secure storage lockers, secure lockers, storage lockers, lockers or units. Lockable compartments may be organized in groupings in varying numbers of units and of varying styles of construction and configuration, such as varying unit size and varying style of lock. A plurality of lockable compartments organized in a grouping may be referred to herein as a bank of lockable compartments, secure locker bank or locker bank. The example illustration of FIG. 1A depicts three locker banks 130, 132 and 134 comprising eight, eight and six lockable compartments, respectively. Generally, locker banks may be located in various geographic locations and do not require a particular geographic relationship to one another or to server based system 111.

In the example illustration of FIG. 1A, secure locker bank 130 comprises eight lockable compartments including lockable compartments 120a and 120b. Lockable compartment 120a comprises a door 121a and a controllable electromechanical lock 122a which may be mounted to and generally hidden by door 121a, and is represented in the example illustration of FIG. 1A with an outline referenced by reference number 122a. A controllable electromechanical lock may be referred to herein simply as lock. Lock 122a may comprise a status indicator 126a, such as an LED for a visual status indicator and may also comprise an audio indicator, such as a tone generator. Door 121a further comprises a handle 123a. Similarly lockable compartment 120b comprises a door 121b comprising a handle 123b and a lock 122b which may be mounted to and generally hidden by door 121b and may comprise a status indicator 126b. Door 121b further comprises a keypad 124b which may be an assembled part of lock 122b or is otherwise operably connected to lock 122b. Locker bank 130 further comprises a communications link 184 to communications network 180 and thereby may communicate with server based system 111.

In the example illustration of FIG. 1A, secure locker bank 132 comprises eight lockable compartments including lockable compartments 120c and 120d. Similar to lockable compartment 120a, lockable compartment 120c comprises a door 121c comprising a handle 123c and a lock 122c which may be mounted to and generally hidden by door 121c and may comprise a status indicator 126c. In the example given, the handle 123c is an assembled part of or otherwise operably connected to lock 122c and is rotatable such that it is operable to retract a bolt (not shown) securing the closure of door 121c when so enabled for opening. Similar to lockable compartment 120c, lockable compartment 120d comprises a door 121d comprising a handle 123d and a lock 122d which may be mounted to and generally hidden by door 121d and may comprise a status indicator 126d. Handle 123d is an assembled part of or otherwise operably connected to lock 122d and is rotatable such that it is operable to retract a bolt (not shown) securing the closure of door 121d when so enabled for opening. Door 121d further comprises a keypad 124d which may be an assembled part of lock 122d or is otherwise operably connected to lock 122d. Locker bank 132 further comprises kiosk 140 and a communications link 185 to communications network 180 and is thereby accessible to server based system 111 which is also connected to network 180. Kiosk 140 comprises a touchscreen 142, a keypad 144 and a card reader 146.

In the example illustration of FIG. 1A, secure locker bank 134 comprises six lockable compartments including lockable compartments 120e and 120f. Lockable compartment 120e is similar to lockable compartment 120a and comprises a door 121e comprising a handle 123e and a lock 122e which may be mounted to and generally hidden by door 121e and may comprise a status indicator 126e. Lockable compartment 120f is similar to lockable compartment 120b and comprises a door 121f comprising a handle 123f and a lock 122f which may be mounted to and generally hidden by door 121f and may comprise a status indicator 126f Door 121f further comprises a keypad 124f which may be an assembled part of lock 122f or is otherwise operably connected to lock 122f. Locker bank 134 does not comprise a communications link to communications network 180 as do locker banks 130 and 132, which have communications links 184 and 185, respectively.

Secure locker system 100 may also comprise one or more portable wireless devices, as shown in the example illustration of FIG. 1A and depicted by portable wireless devices 150, 152 and 154. Portable wireless devices 150, 152 and 154 are useable by users for interacting with the secure locker system 100 to rent and access a lockable compartment or access an otherwise assigned lockable compartment, or perform other related interactions such as search for available lockable compartments, terminate a locker rental and the like. Portable wireless devices 150, 152 and 154 can be smartphones, and may also be smartwatches, cell phones, tablets, laptops and other devices which provide a user interface and can be communicatively connected to server based system 111, and locks, such as locks 122a-122f Portable wireless devices 150, 152 and 154 may comprise at least one type of wireless communications capability such as a cellular internet communications, herein also referred to as a wide area network (WAN) capability, a short range communications capability, such as Bluetooth communications, and a wireless local area network (WLAN) capability such as an IEEE 802.11 based WLAN (Wi-Fi), and many devices, such as many smartphone portable wireless devices, may comprise all three of a WAN, short range and WLAN communications. In the example illustration of FIG. 1A, portable wireless devices 150, 152 and 154 are each depicted comprising two communications links. Links 190, 192 and 194 of devices 150, 152 and 154, respectively, are represented as lightning bolt symbols and are short range links. Links 186, 187 and 188 of devices 150, 152 and 154, respectively, are represented as solid lines and may be WAN links, WLAN links or both.

Secure locker system 100 may additionally comprise one or more operator devices, such as a computer 112 or a tablet 113, which comprise a communications link 182 or 183, respectively. Operator devices 112 and 113 are used by personnel engaged in managing the operations of secure locker system 100, and be used to perform such functions as review the volume of locker rentals over time, review advanced rental bookings, review the current number of available lockers, review the anticipated or predicted shortages of available lockers, review actual and projected rental revenues, review and report issues, review and issue maintenance requests, and the like. Operator devices 112 and 113 may additionally be laptop computers, smartphones and other electronic devices, and be used for locker installation and maintenance operations of lockable compartments and locker bank installations. Operator devices 112 and 113 may additionally comprise wireless communications capability such as a cellular internet (WAN) communications capability and a wireless local area network (WLAN) capability such as an IEEE 802.11 based WLAN (Wi-Fi), which are illustrated in FIG. 1A by communications links 182, for device 112, and 183, for device 113. Additionally, operator devices 112 and 113 may comprise a short range communications capability, such as Bluetooth communications, as depicted by links, 196 and 198, respectively.

Figure 1B:
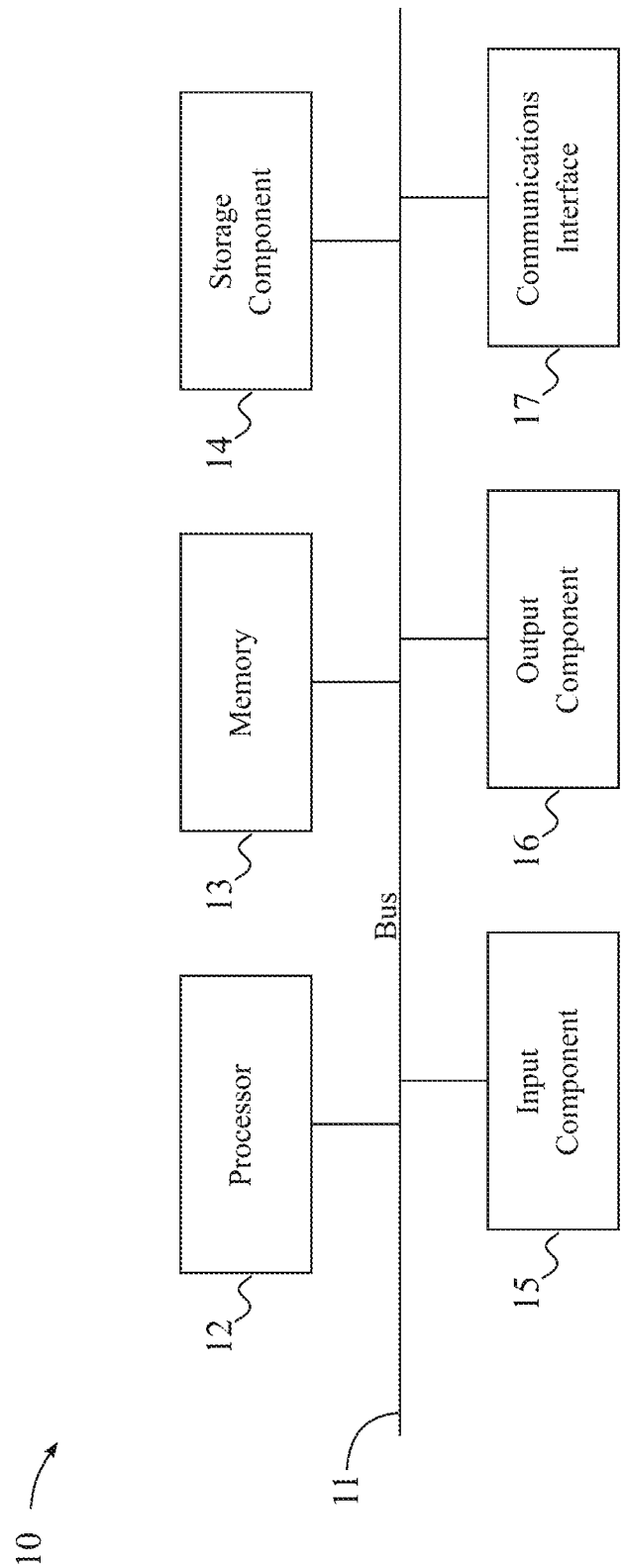
FIG. 1B is an example illustration depicting a diagram of example components of a device 10.

FIG. 1B is an example illustration depicting a diagram of example components of a device 10. Device 10 may correspond to server based system 111, operator devices 112 and 113, kiosk 140, portable wireless devices 150, 152 and 154, and emergency access systems 119a, 119b and 119c. Device 10 may also correspond to lock access controllers which may be comprised by intelligent electromechanical locks or controller boards controlling simple electromechanical locks, not explicitly depicted in FIG. 1A. As depicted in FIG. 1B, device 10 may comprise a bus 11, a processor 12, a memory 13, a storage component 14, an input component 15, an output component 16, and a communication interface 17. In some embodiments, server based system 111, operator devices 112 and 113, kiosk 140, portable wireless devices 150, 152 and 154, emergency access systems 119a, 119b and 119c and/or lock access controllers may include one or more devices 10 and/or one or more components of device 10.

Bus 11 includes a component that permits communication among the components of device 10. Processor 12 may be implemented in hardware, firmware, or a combination of hardware and firmware. Processor 12 includes a processor (e.g., a central processing unit (CPU), a graphics processing unit (GPU), and/or an accelerated processing unit (APU)), a microprocessor, a microcontroller, and/or any processing component (e.g., a field-programmable gate array (FPGA) and/or an application-specific integrated circuit (ASIC)) that interprets and/or executes instructions. In some implementations, processor 12 includes one or more processors capable of being programmed to perform a function. Memory 13 includes a random access memory (RAM), a read only memory (ROM), and/or another type of dynamic or static storage device (e.g., a flash memory, a magnetic memory, and/or an optical memory) that stores information and/or instructions for use by processor 12.

Storage component 14 stores information and/or software related to the operation and use of device 10. For example, storage component 14 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 15 includes a component that permits device 10 to receive information, such as via user input (e.g., a touch screen display, a keyboard, a keypad, a mouse, a button, a switch, and/or a microphone). Additionally, or alternatively, input component 15 may include a sensor for sensing information (e.g., a global positioning system (GPS) component, an accelerometer, a gyroscope, and/or an actuator). Output component 16 includes a component that provides output information from device 10 (e.g., a display, a speaker, and/or one or more light-emitting diodes (LEDs)).

Communication interface 17 includes a transceiver-like component (e.g., a transceiver and/or a separate receiver and transmitter) that enables device 10 to communicate with other devices, such as via a wired connection, a wireless connection, or a combination of wired and wireless connections. Communication interface 17 may permit device 10 to receive information from another device and/or provide information to another device. For example, communication interface 17 may include an Ethernet interface, an optical interface, a coaxial interface, an infrared interface, a radio frequency (RF) interface, a universal serial bus (USB) interface, a Wi-Fi interface, a cellular network interface, or the like.

Device 10 may perform one or more processes described herein. Device 10 may perform these processes in response to processor 12 executing software instructions stored by a non-transitory computer-readable medium, such as memory 13 and/or storage component 14. A computer-readable medium is defined herein as a non-transitory memory device. A memory device includes memory space within a single physical storage device or memory space spread across multiple physical storage devices. In some implementations, a memory device may be cloud-based, partially cloud-based, or not cloud-based.

Software instructions may be read into memory 13 and/or storage component 14 from another computer-readable medium or from another device via communication interface 17. When executed, software instructions stored in memory 13 and/or storage component 14 may cause processor 12 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 1B are provided as an example. In practice, device 10 may include additional components, fewer components, different components, or differently arranged components than those shown in FIG. 1B. Additionally, or alternatively, a set of components (e.g., one or more components) of device 10 may perform one or more functions described as being performed by another set of components of device 10.

Returning to FIG. 1A, server based system 111 may enable a portable wireless device for secure access to a lockable compartment by providing the portable wireless device with a single use access authentication code for use as a challenge code. A single use access authentication challenge code is unique to a single access transaction. A single use access authentication code is also independently generated by a lock access controller controlling the lock of the lockable compartment to be accessed for use as a corresponding verification code. The use of access authentication codes that may only be used once ensures that a disclosure and malicious capture of any code limits the exposure of unauthorized access to a single access event of a specific lockable compartment. In an embodiment, a challenge code may only be generated and provided by server based system 111 to a requesting portable wireless device when the requesting portable wireless device is in close proximity to the lockable compartment to be accessed. As such, at the time the code is generated, the user of the requesting portable wireless device is presumably readying to open the lockable compartment and the challenge code has a substantially limited useful lifetime which may commonly be less than a second. In an embodiment, a challenge code and independently generated verification code may only be generated upon the initiation of an access request presented lock access controller, upon which, a time window for use of the verification and challenge codes may be established, wherein if the codes are not used in conjunction with an access event within the time window, the codes expire and are no longer useable.

A secure protocol may be established for independent generation of single use access authentication codes by server based system 111 for each lock. A secure protocol may use encryption such as the Advanced Encryption Standard (AES) published by the National Institute of Standards and Technology (NIST). Code derivation encryption keys, also referred to herein as code derivation keys or derivation keys, may be established such that they are solely known to the server based system 111 and a lock access controller which may reside within a lock or a controller board controlling one or more locks. When a lock is to be made operable in secure locker system 100, it can be initialized with a unique code derivation key and an input code which reside in each of: a) the lock access controller controlling the lock for use in generating verification codes by a verification code generator comprised by the lock access controller, wherein the lock access controller comprises a processor programmed to generate verification codes, and b) a lock access table maintained by server based system 111 for use in generating challenge codes by a challenge code generator comprised by server based system 111, wherein server based system 111 comprises a processor programmed to generate challenge codes. Upon a first access of a newly initialized lock, a first generated single use access authentication code is generated by both server based system 111, for use as a challenge code, and the lock access controller controlling the access locked, for use as a verification code, by independently encrypting the input code with the code derivation key independently comprised therein. A second access code and further subsequent access codes are generated by encrypting the last generated access code with the code derivation key. As such, a next single use access authentication code may be represented by the following equation:

$$\text{Code}(n)=E[\text{Code}(n-1),\text{CDK}]$$

Where:
Code (n) is the next single use access authentication code following the last generated code,
Code (n−1) is the last generated single use access authentication code,
E is a suitable encryption method such as AES and comprises as inputs the last generated access authentication code, Code (n−1), as the input code and a code derivation key, CDK, and
CDK is the code derivation key which is used to encrypt the last generated single use access authentication code, Code (n−1) as the input code, to create the next code, Code (n).

Figure 3A:
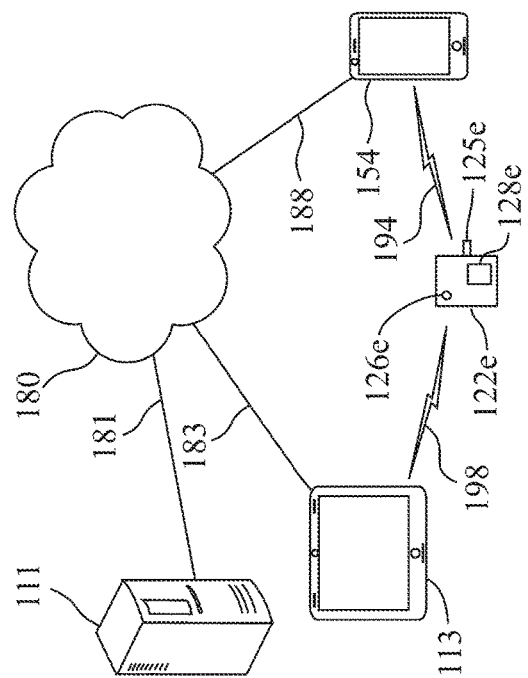
FIG. 3A is an example illustration depicting a portion of the system diagram of a secure locker system of FIG. 1A.
Figure 4A:
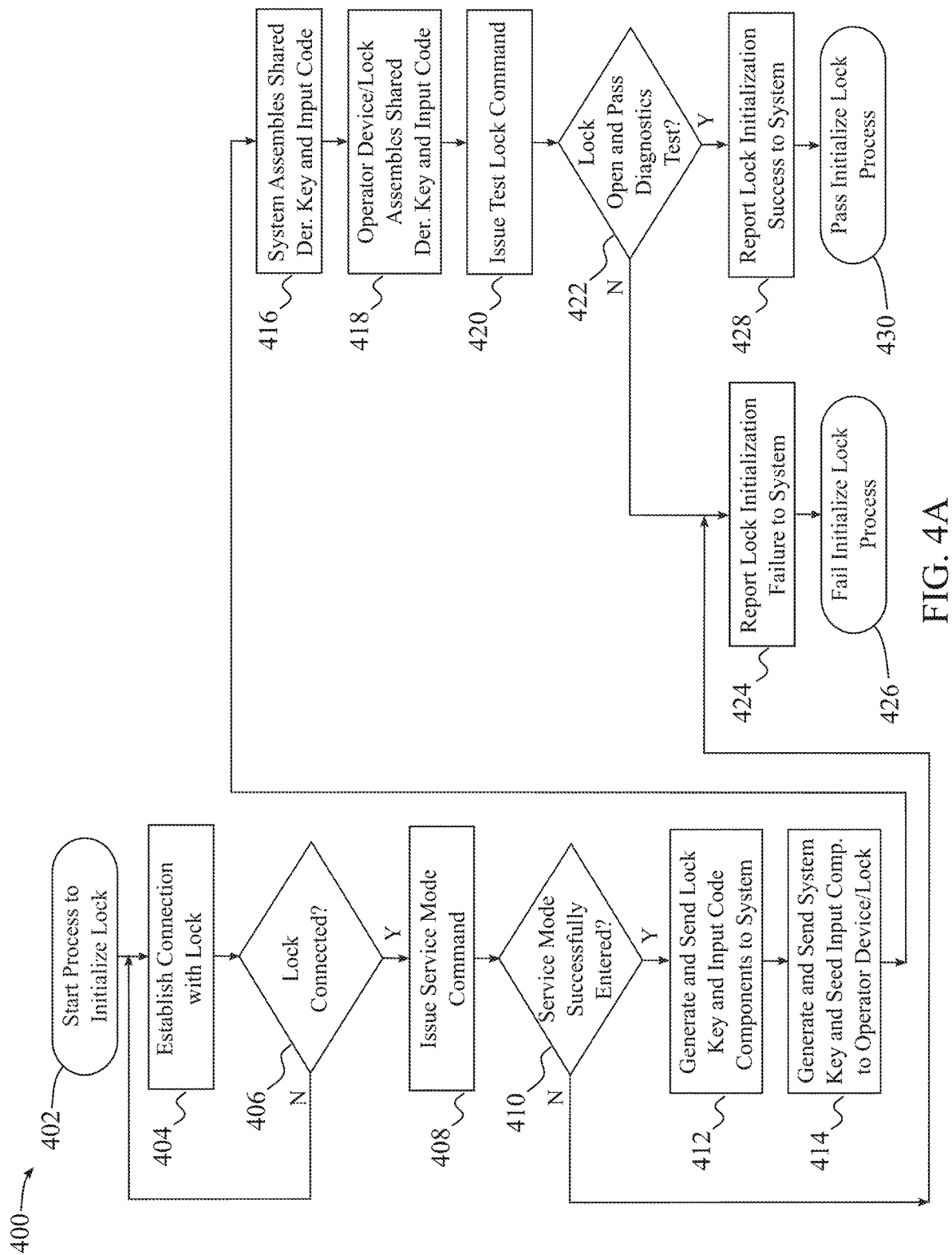
FIG. 4A is an example illustration depicting a flowchart representation of a lock initialization process.
Figure 4B:
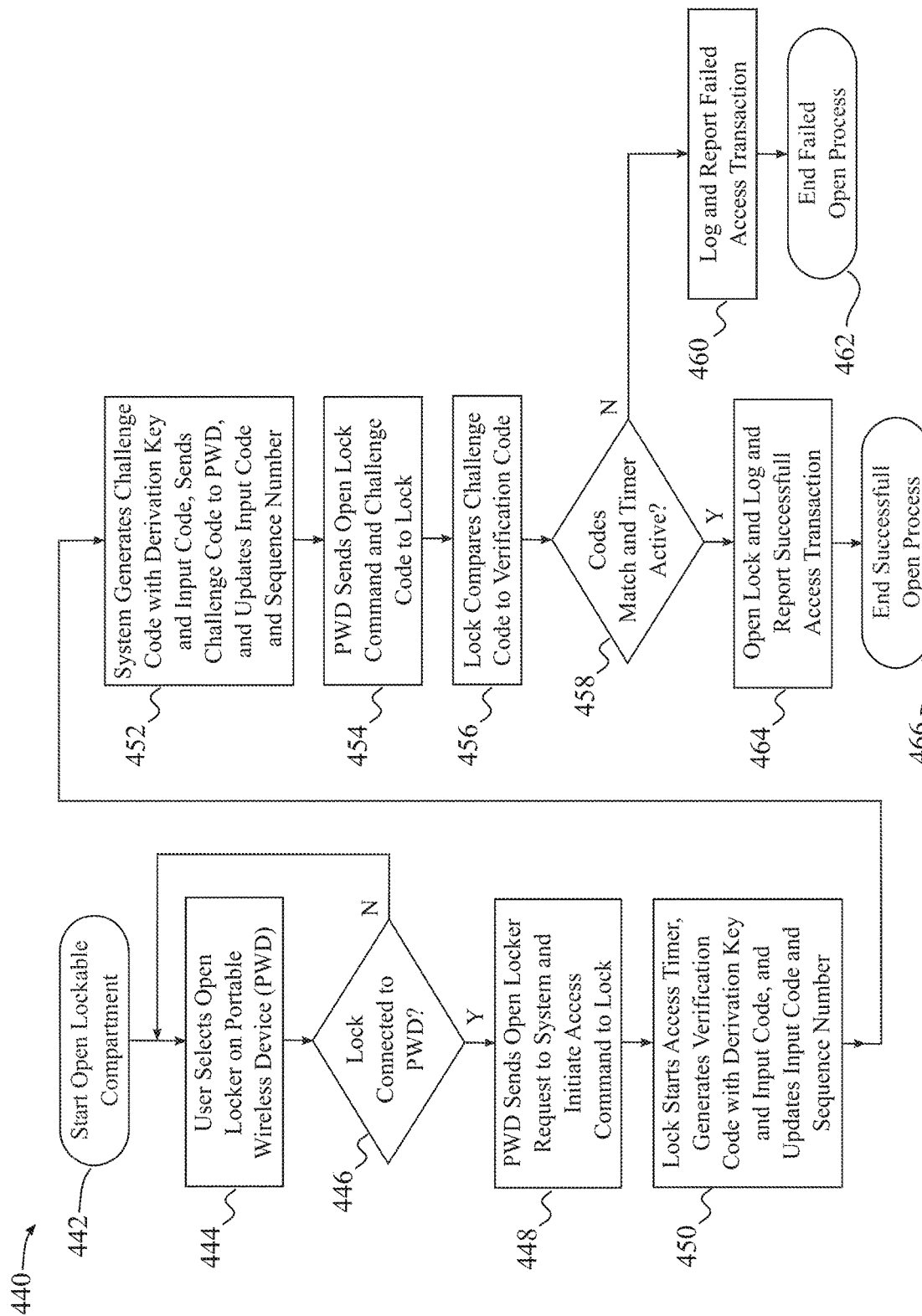
FIG. 4B is an example illustration depicting a flowchart representation of a process to open a lock of a lockable compartment for opening and access thereof.

The process for initializing a lock, such as locks 122a-122f, for use in secure locker system 100 and the process for enabling a portable wireless device, such as devices 150, 152 and 154, for accessing a lockable compartment, such as compartments 120a-120f and opening a lock 122a-122f thereof, will be described in more detail in conjunction with FIG. 4A and FIG. 4B, respectively, and further in conjunction with and following an overview of FIG. 2A and FIG. 3A. FIG. 2A is an example illustration depicting a lock access table 200 which may be comprised by server based system 111. Lock access table 200 comprises a location ID column 210, a locker ID column 212, a lock ID column 214, an input code column 216, a derivation key column 218 and a sequence number column 220. In the example illustration, lock access table 200 comprises a plurality of records 201 through 206, wherein records 201 and 202 are associated with lockers 120a and 120b, and locks 122a and 122b, of locker bank 130; records 203 and 204 are associated with lockers 120c and 120d, and locks 122c and 122d, of locker bank 132; and records 205 and 206 are associated with lockers 120e and 120f, and locks 122e and 122f, of locker bank 134. FIG. 3A is an example illustration depicting a portion of secure locker system 100 of FIG. 1A, comprising lock 122e of locker bank 134, portable wireless device 154, operator device 113, server based system 111 and network 180. FIG. 4A is an example illustration depicting a flowchart representation of a lock initialization process 400. FIG. 4B is an example illustration depicting a flowchart representation of a process 440 to open a lock of a lockable compartment for opening and access thereof.

Referring to process 400 of FIG. 4A in conjunction with FIG. 2A and FIG. 3A, an operator device 113 is connected with server based system 111 over network 180 and communications links 183 and 181. An operator of operator device 113 initiates process 400 to initialize lock 122e which begins in step 402. Operator device 113 and server based system 111 exchange or have already exchanged public keys of respectively comprised public/private key pairs and can also use digital certificates issued from trusted third party certificate authorities to mutually authenticate each other in order to engage in lock initialization process 400. The public keys may be used to securely exchange independently generated derivation key component values and input code component values, using an asymmetric encryption such as the Rivest-Shammir-Adleman (RSA) asymmetric encryption. The component values are then individually assembled within operator device 113 and server based system 111 to create a shared code derivation key and shared input code needed for initialization process 400. In an embodiment, lock access controller 128e (FIG. 3A) of lock 122e comprises asymmetric encryption and operator device 113 provides lock access controller 128e with the server based system 111 public key, such that derivation key and input code components values may be generated and encrypted within lock access controller 128e. In such an embodiment, an unencrypted lock derivation key component and unencrypted input code component needs not reside outside of lock access controller 128e, thereby eliminating the ability to intercept these values in an unencrypted (clear text) form outside of lock access controller 128e.

The relationship between exchanged code derivation key component values, public/private key pairs and the assembled shared code derivation key is shown in Table 1 below. For brevity, the operator device 113 or lock access controller 128e generated components can be referred to as lock code derivation key component, or lock key component, and lock input code component, and the server based system 111 generated components can be referred to as system code derivation key component, or system key component, and system input code component.

TABLE 1

| | Secure Exchange of Code Derivation Key Components for Shared Key Generation | |
|---|---|---|
| Operation | Operator Device or Lock Access Controller | Server Based System |
| Randomly Generate Key Component | LoDKComp | SyDKComp |
| Encrypt Key Component | E [LoDKComp, SyPuK] | E [SyDKComp, OpPuK] |
| Decrypt Received Key Component | D [$\overline{\text{SyDKComp}}$, OpPrK] | D [$\overline{\text{LoDKComp}}$, SyPrK] |
| Generate/Assemble Key | A [LoDKComp, SyDKComp] | A [LoDKComp, SyDKComp] |

Where:
LoDKComp is the lock key component,
$\overline{\text{LoDKComp}}$ is the encrypted lock key component,
SyDKComp is the system key component,
$\overline{\text{SyDKComp}}$ is the encrypted system key component,
OpPuK is the operator device public key,
OpPrK is the operator device private key,
SyPuK is the server based system public key, and
SyPrK is the server based system private key.

The relationship between exchanged input code component values, public/private key pairs and the assembled shared input code is shown in Table 2 below.

TABLE 2

| Secure Exchange of Input Code Components for Shared Input Code Generation | | |
|---|---|---|
| Operation | Operator Device or Lock Access Controller | Server Based System |
| Randomly Generate Input Code Comp. | LoICComp | SyICComp |
| Encrypt Input Code Component | E [LoICComp, SyPuK] | E [SyICComp, OpPuK] |

TABLE 2-continued

Secure Exchange of Input Code Components for Shared Input Code Generation

| Operation | Operator Device or Lock Access Controller | Server Based System |
|---|---|---|
| Decrypt Received Input Code Comp. | D [$\overline{\text{SyICComp}}$, OpPrK] | D [$\overline{\text{LoICComp}}$, SyPrK] |
| Assemble Input Code | A [LoICComp, SyICComp] | A [LoICComp, SyICComp] |

Where:
LoICComp is the lock input code component,
$\overline{\text{LoICComp}}$ is the encrypted lock input code component,
SyICComp is the system input code component,
$\overline{\text{SyICComp}}$ is the encrypted system input code component,
OpPuK is the operator device public key,
OpPrK is the operator device private key,
SyPuK is the server based system public key, and
SyPrK is the server based system private key.

In step 404 operator device 113 attempts to establish a secure connection 198 (FIG. 3A) with lock 122e using a secure communication protocol, for example, a Bluetooth security level 4, security mode 2 secure connection, as described in NIST Special Publication 800-121, Revision 2, published May 2017. In step 406, once secure connection 198 is established, the process moves to step 408, wherein operator device 113 issues a service mode command to lock 122e. This command can result in multiple process steps not depicted in FIG. 4A, such as, indicating, via communications links 183 and 181 and network 180, a service mode request to server based system 111 to put lock 122e into a service mode, and receiving in response a challenge code and an encrypted sequence number as a secure service mode token, wherein the encrypted sequence number is encrypted using the code derivation key. Referring to the example illustration of lock access table 200 of FIG. 2A, to prepare this response comprising a challenge code and encrypted sequence number, server based system 111 retrieves the input code, derivation key and sequence number for lock 122e from record 205. For locks not previously initialized and put into use, these values may be based on keys, codes and sequence numbers created during a lock access controller production process, and may be unique or default values. Generally, in addition to its use as a service mode token used to establish a service mode in lock, a sequence number can be used to maintain synchronization between server based system 111 and a lock access controller, and can also approximate or equal the number of actual access cycles of a lock if the sequence number is initially set to zero during manufacturing. Maintaining a record of lock access cycles can be useful for service, maintenance and reliability procedures and analysis of locks over their service lifetime. Server based system 111 then encrypts the input code, which may simply be a default input code created during manufacturing, using the derivation key to generate a challenge code needed for the pending service mode command. Server based system 111 encrypts the sequence number using the derivation key to generate an encrypted sequence number which is also needed as a secure token for the pending service mode command. As will be seen more clearly later, restricting provision of an encrypted sequence number for use by an authenticated operator device to invoke a lock service mode, prevents a rogue device spoofing as a user device from invoking a lock service mode armed solely with a challenge code. Server based system 111 then responds to operator device 113 with the required challenge code and encrypted sequence number. Operator device 113 then issues to lock 122e via short range connection 198 the service command comprising the challenge code and encrypted sequence number. Lock access controller 128e of lock 122e maintains data corresponding to record 205 comprising an input code, derivation key and sequence number, and independent of server based system 111 generates a verification code and encrypted sequence number (or alternatively decrypts the received encrypted sequence number). In step 410, if the verification code matches the challenge code and the received encrypted sequence number matches the lock generated encrypted sequence number (or alternatively the decrypted received sequence number matches the lock sequence number), the lock successfully enters service mode and the lock opens, wherein a lock bolt 125e retracts and an indicator 126e may indicate a successful entry into service mode (e.g., flashing a green color and/or sounding a brief tone). If in step 410, the verification code and challenge code do not match, or the received encrypted sequence number and lock generated encrypted sequence number do not match (or alternatively the decrypted received sequence number does not match the lock sequence number), then the service mode command fails, indicator 126e may indicate a failed entry into service mode (e.g., flashing a red color and/or sounding a long tone), and in step 424, the process reports the failure to server based system 111 and ends in a failed initialize lock process in step 426.

Upon successful entry into service mode in step 410, the initialization process generates a new shared secret derivation key and a new shared secret input code by the independent generation, encryption and secure mutual exchange of encrypted key components and encrypted input code components by server based system 111 and the operator device 113 or lock access controller 128e as will now be described. In step 412, operator device 113 or lock access controller 218e generates the encrypted lock key component, $\overline{\text{LoDKComp}}$, per Table 1 above, and the encrypted lock input code component, $\overline{\text{LoICComp}}$, per Table 2 above, and sends them to server based system 111. For explanatory purposes, an embodiment where lock access controller 128e generates the components will be described. Operator device 113 sends the server based system public key, SyPuK, to lock access controller 128e. Lock access controller 128e using a pseudo random number generator generates a lock key component, LoDKComp, and a lock input code component, LoICComp. Then using SyPuK, lock access controller 128e encrypts the components thereby generating $\overline{\text{LoDKComp}}$ and $\overline{\text{LoICComp}}$ which it sends to operator device 113 for secure communication to server based system 111. Server based system 111 may then decrypt these components using SyPrK, the server based system 111 private key, and reserve them for final assembly of the new shared code derivation key and new shared input code for lock 122e.

In step 414, server based system 111 generates the encrypted system key component, $\overline{\text{SyDKComp}}$, per Table 1 above, and the encrypted lock input code component, $\overline{\text{SyICComp}}$, per Table 2 above, and sends them to operator device 113 or lock access controller 218e. Server based system 111 using a pseudo random number generator generates a system key component, SyDKComp, and a system input code component, SyICComp. Then using the operator device public key, OpPuK, server based system 111 encrypts the components thereby generating $\overline{\text{SyDKComp}}$ and $\overline{\text{SyICComp}}$ which it sends to operator device 113. Server based system 111 may now in step 416 assemble the new shared code derivation key per Table 1 above from the component parts, A [LoDKComp, SyDKComp], and the new shared input code per Table 2 above from the component parts, A [LoICComp, SyICComp], and load them into the derivation key and input code of record 205 of lock access table 200. Operator device 113 receives and then decrypts $\overline{\text{SyDKComp}}$ and $\overline{\text{SyICComp}}$ using OpPrK and sends the resulting SyDKComp and SyICComp to lock access controller 128e. In step 418, lock access controller 122e may now assemble and store therein the new shared code derivation key from the component parts, A [LoDKComp, SyDKComp], and the new shared input code from the component parts, A [LoICComp, SyICComp], for use in future service and access requests.

In step 420 operator device 113 issues a test lock command to verify the newly generated derivation key and input code are operable and that the lock opens properly by executing an access locker command, which will be described later herein in conjunction with FIG. 4B, and may also run other lock diagnostics, such as check a battery status or verify a memory checksum. If the lock does not open properly or certain diagnostic tests fail then the initialization process fails and process 400 proceeds to step 424. In step 424 the process reports the failure to server based system 111 and in step 426 ends in a failed initialize lock process. Note that some diagnostic test failures, may be resolved, for example, a battery may be replaced, after which the diagnostic test and initialization process may then pass. If in step 422 the lock opens and the diagnostics test pass, then process 400 proceeds to step 428 wherein the successful initialization of lock 122e is reported to server based system 111 and initialize lock process 400 ends in step 430. Note that the operator device 113 may also prompt the user to execute a check list of other lockable compartment 120e (FIG. 1A) tests and assessments, such as an assessment of whether the locker door 121e (FIG. 1A) moves freely, locker interior is clean and free of debris, etc., and if appropriate based on the results of the results of the tests and assessments, allow or disallow lockable compartment 120e to be put into service.

By using independently generated and mutually exchanged derivation key components and input code components which are passed under respective public/private key pairs, a considerable level of additional security protection is achieved beyond security which may be achieved through a sending of a complete derivation key or input code using only transport level security protocols, such as TLS, to secure the key or code. Namely, both secret private keys and the cypher text of all component parts must be respectively obtained and intercepted in order to assemble the derivation key and input code. Furthermore, an additional point of device authentication is realized as both server based system 111 and operator device 113 must exercise a private key known only to them to decrypt a received component in order for it to ultimately be put into use.

Figure 3B:
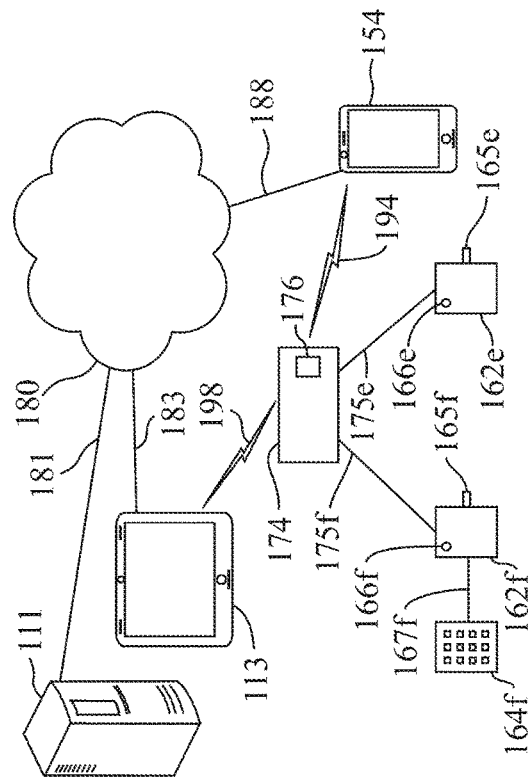
FIG. 3B is an example illustration depicting a portion to a portion of the system diagram of a secure locker system of FIG. 1A

Referring now to FIG. 4B, FIG. 4B is an example illustration depicting a flowchart representation of a process 440 to open a lock of a lockable compartment for opening and access thereof. FIG. 4B will be discussed in conjunction with FIG. 2A and FIG. 3B. FIG. 3B is an example illustration depicting a similar portion of secure locker system 100 of FIG. 1A as shown in FIG. 3A, but comprising a lock controller board 174 controlling locks 162e and 162f. Lock controller board 174 comprises lock access controller 176 and lock interfaces 175e and 175f for controlling lock units 162e and 162f, respectively. A lock controller board such as controller board 174 may be connected to and control a plurality of locks units comprised by a locker bank, wherein wiring harnesses connect electrical power and signals to actuate lock bolts, such as wiring harnesses 175e and 175f, lock bolts 165e and 165f, and control indicators 166e and 166f of locks 162e and 162f. As such, lock controller board driven locks 162e and 162f may be referred to as controller board driven locks, simple locks or dumb locks, and locks 122a-122f comprising lock access controllers may be referred to as intelligent locks or smart locks. Process 440 of FIG. 4B is applicable to opening both a lockable compartment comprising an intelligent lock and a lockable compartment comprising a controller board driven lock.

Open lockable compartment process 440 begins in step 442. As will be disclosed in more detail later herein, process 440 may be initiated by a user of a portable wireless device 154 in conjunction with a secure locker software app downloaded onto portable wireless device 154, wherein the user selects an open locker selection in step 444. In step 446, the portable wireless device 154 checks to see if it is logically connected to lock 162e, which, in the example illustration of FIG. 3B, is driven by controller board 174, and as such, the physical connection, albeit a wireless connection, is made to controller board 174, via short range link 194. Once connected, in step 448, portable wireless device 154, sends an open lock request to server based system 111 via communication links 188 and 181 and network 180, and sends an initiate access command to lock access controller 176. The initiate access command prompts lock access controller 176 in step 450 to start a lock access timer, such as a one second or five second timer, which may be used to limit the usable lifetimes of generated single use access authentication codes, namely, the usable lifetimes of a challenge code and a verification code of the current lock access attempt. Further in step 450, lock access controller 176 retrieves the derivation key and input code for lock 162e and generates the verification code, per the single use access authentication code equation disclosed earlier and restated below for convenience:

$$\text{Code}(n) = E[\text{Code}(n-1), \text{CDK}]$$

Where:

Code (n) is the next single use access authentication code following the last generated code, Code (n−1) is the last generated single use access authentication code, E is a suitable encryption method, such as AES, and comprises as inputs the last generated access authentication code, Code (n−1) as the input code, and a code derivation key, CDK, and CDK is the code derivation key which is used to encrypt the last generated single use access authentication code, Code (n-1) as the input code, to create the next code, Code (n).

Additionally in step 450, lock access controller 176 updates the input code with the newly generated verification code for lock 162e and increments the sequence number for lock 162e. In step 452, server based system 111 retrieves the derivation key and input code from record 205 (which corresponds to lock 162e) of table 200 and generates the challenge code, per the above access code equation, and sends the challenge code to portable wireless device 154. Additionally in step 452, server based system 111 updates the input code with the newly generated challenge code and increments the sequence for record 205 of table 200. In step 454, portable wireless device 154 sends via short range link 194 an open lock command and the challenge code to controller board 174 comprising lock access controller 176 for lock 162e. In step 456, lock access controller 176 compares the received challenge code to the generated verification code. In step 458, if the challenge code and verification code are not equal or the access timer started in step 450 has expired, the process proceeds to step 460, wherein lock access controller 176 logs and reports to server based system 111 via portable wireless device 154 that the lock access transaction failed, and process 440 ends in step 462.

In an embodiment, in step 452, a sequence number of record 205 of table 200 may be included with the challenge code from server based system 111, and a similarly maintained sequence number of lock access controller 176 for lock 162e may be used to determine an out of sequence condition between the generation of challenge codes by server based system 111 and the respective generation of verification codes by lock access controller 176 for lock 162e. If in step 456, lock access controller 176 comprises a sequence number reporting a number of fewer code generation cycles it can "cycle" verification codes until it evens up the sequence numbers to resolve the discrepancy and potentially achieve a matching of the challenge code and verification code. If in step 456 lock access controller 176 comprises a sequence number for lock 162e reporting a number of greater code generations it can request server based system 111, via portable wireless device 154, "cycle" challenge codes until it evens up the sequence numbers to resolve the discrepancy and potentially provide a successful challenge code. It is noted that a similar cycle and even up process with regard to sequence numbers may be used in step 410 of the example lock initialization process 400 of FIG. 4A, wherein if the verification code does not match the challenge code, the received encrypted sequence number is decrypted to assess a discrepancy between a sequence number of record 205 of table 200 of server based system 111 and a sequence number for lock access controller 126e of FIG. 3A in the discussed example. Lock access controller 126e can either cycle, or request via portable wireless device 154 that server based system 111 cycle to even up the sequence numbers accordingly and potentially resolve the issue. Of additional note, a process wherein lock access controller 176 or lock access controller 126e cycles backwards by decrypting the last access code and reduces the sequence number in order to even up sequence numbers with server based system 111 should not be contemplated, as this would make the secure locker system 100 vulnerable to replay attacks wherein a previous used open lock command could be resubmitted and the lock access controller being attacked would simply cycle backwards until the sequence numbers and accordingly verification and challenge codes match.

In step 458, if the challenge code matches the verification code, and the access timer started in step 450 is active and has not expired, then process 440 proceeds to step 464, wherein lock controller board 174 and lock access controller 176, via wiring harness 175e, actuates lock bolt 165e to open the lockable compartment, and may indicate such actuation and opening via indicator 166e. Furthermore in step 464, lock access controller 176 logs and reports to server based system 111 via portable wireless device 154 the successful lock access transaction. Process 440 then proceeds to step 466 where process 440 ends.

A user may wish to store their portable wireless device in a lockable compartment for which they have a rental session, or for which they have an assigned use thereof. In an embodiment of FIG. 3B where a lock 162f comprises or is otherwise connected to a keypad 164f connected to lock 162f via connection 167f, a user may submit a request to assign a user PIN (request to assign PIN) and select a PIN on portable wireless device 154. The request to assign PIN results in a similar process flow as process 440, namely, an initiate user PIN command sent by the portable wireless device to the lock access controller and the generation and of a challenge code by server based systems 111 which is then sent to the user portable wireless device. The assign user pin submission by portable wireless device 154 with the selected PIN in combination with a successful challenge code to lock access controller 176 for lock 162f, will cause lock access controller 176 for the duration of the present rental session or assignment to accept, via keypad wiring harness 167f, a correctly entered user PIN, when entered through keypad 164f, and via wiring harness 175f, actuate lock bolt 165f to open lock 162f and actuate indicator 166f to indicate a successful opening, as if a matching of a verification code and challenge code had occurred in conjunction with an open lock request. If a user suspects their selected PIN may have been compromised, they can submit another assign user PIN request and select another PIN on their portable wireless device, or submit a request to cancel and deactivate their current access PIN, should they determine they no longer want or need the capability of access via keypad 164f. Upon an access in conjunction with a termination of a rental session or assignment, server based system 111 submits via portable wireless device 154 a request to cancel and deactivate the access PIN.

Referring to locker bank 132 of FIG. 1A, locker bank 132 comprises a kiosk 140 comprising a touchscreen user interface 142, an electronic payment keypad 144, which may accept secure entry of a debit card PIN number, and a chip and magnetic stripe card reader 146. Kiosk 140 may be used by users to rent and access lockable compartments in an alternative way to using portable wireless devices as previously described. Kiosk 140 may be used when a user does not have a portable wireless device or their portable wireless device is otherwise not available, for example, the battery is fully depleted. In the example illustration of FIG. 1A, kiosk 140 can interact with locks 122c and 122d in a similar fashion as a portable wireless device described earlier herein. Kiosk 140 can communicate with server based system 111 via communications links 185 and 181 over network 180 to send an open locker request of process 440 of FIG. 4B, and in response receive a challenge code for access thereto. Kiosk 140 can be configured with a lock controller board to control simple locks, can be configured to communicate directly with intelligent locks via a communications link, such as a short range link, or both. A user having a user account with secure locker system 100 can use kiosk 140 to log into their account to facilitate the rental process, or can otherwise use the system as a guest user. In the example illustration of locker bank 132, a user having a current rental session with lockable compartment 120d can access it using portable wireless device 152 or kiosk 140 by authenticating themselves to server based system by having signed into their user account of a secure locker system application, as will be discussed later herein, and selecting an open locker selection. Alternatively, a user may have previously selected an assign user PIN selection as described earlier, and provided the PIN has not been deactivated by a subsequent request to cancel it, the user may accordingly access lockable compartment 120d using a keypad 124d of lockable compartment 120d, wherein lock access controller controlling lock 122d will open lock 122d upon entry of a correct user PIN as if a challenge code and verification code have been matched in an open lock command.

Figure 3C:
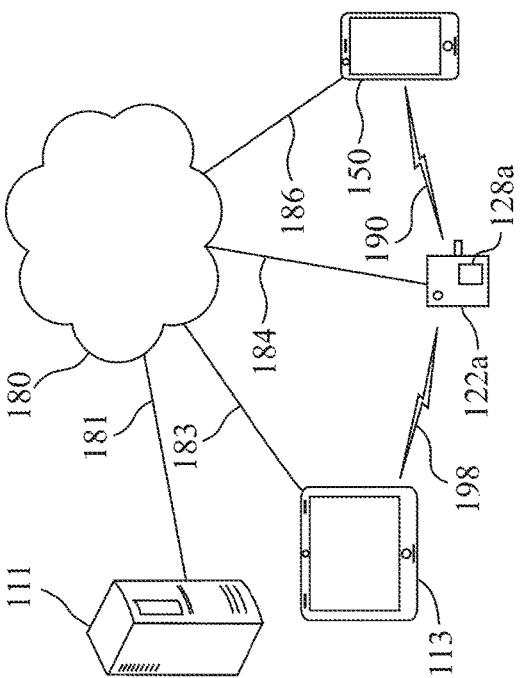
FIG. 3C is an example illustration depicting a portion of the system diagram of a secure locker system of FIG. 1A.

Referring now to FIG. 3C, FIG. 3C is an example illustration depicting a portion of secure locker system of FIG. 1A, comprising lock 122a (of locker bank 130 of FIG. 1A), portable wireless device 150, operator device 113, server based system 111 and network 180. One notable difference between FIG. 3A and FIG. 3C is a communications link 184 connecting lock 122a to network 180 in FIG. 3C, whereas no such communications link connects lock 122e to network 180 in FIG. 3A. Communications link 184 provides lock 122a with an ability to communicate directly with server based system 111, and corroborate an action, and details thereof, being received from user portable wireless device 150 via short range connection 190 or operator device 113 via short range connection 198. Furthermore, reporting of access transactions may be made directly from lock 122a to server based system 111 over link 184, network 180 and link 181, rather than via portable wireless device 150, over short range communications 190, via device 150, link 186, network, 180 and link 181. Similarly, reporting of service transactions may be made directly from lock 122a to server based system 111 over link 184, network 180 and link 181, rather than via operator device 113, over short range communications 198, via device 113, link 183, network, 180 and link 181. While depicted as a link directly to lock 122a, communications link 184 may be implemented as a single communications link, such as a wired or wireless LAN link to a locker bank (locker bank 130 of FIG. 1A) which in turn may provide a wireless link, such as a short range Bluetooth link between a plurality of locks comprising lock 122a, and link 184, thereby providing lock 122a communications to server based system 111 over network 180.

Figure 3D:
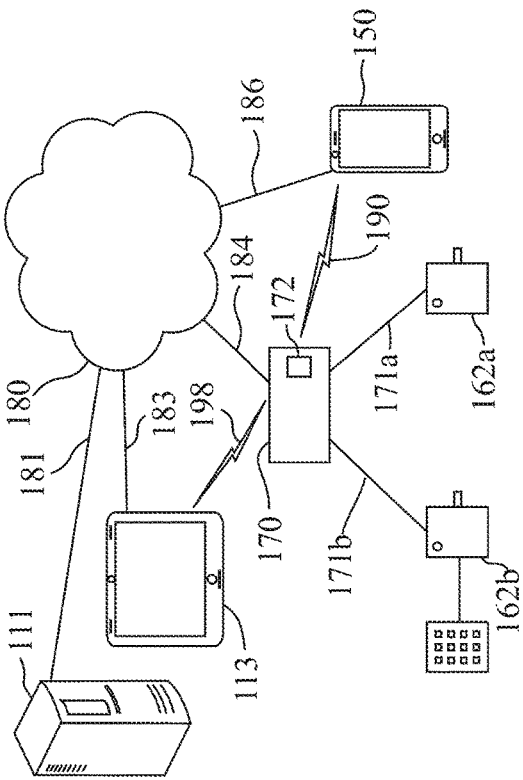
FIG. 3D is an example illustration depicting a portion to a portion of the system diagram of a secure locker system of FIG. 1A

Referring now to FIG. 3D which depicts an embodiment of a portion similar to secure locker system 100 of FIG. 1A, FIG. 3D comprises a lock controller board 170, portable wireless device 150, operator device 113, server based system 111 and network 180. One notable difference between FIG. 3B and FIG. 3D is a communications link 184 connecting lock controller board 170 to network 180 in FIG. 3D, whereas no such communications link connects lock controller board 174 to network 180 in FIG. 3B. Lock controller board 170 comprises lock access controller 172 and lock interfaces 171a and 171b for controlling lock units 162a and 162b, respectively. Communications link 184 provides lock controller board 170 with an ability to communicate directly with server based system 111, and corroborate an action, and details thereof, being received from user portable wireless device 150 via short range connection 190 or operator device 113 via short range connection 198. Furthermore, reporting of access transactions may be made directly from lock controller board 170 to server based system 111 over link 184, network 180 and link 181, rather than via portable wireless device 150, over short range communications 190, via device 150, link 186, network, 180 and link 181. Similarly, reporting of service transactions may be made directly from lock controller board 170 to server based system 111 over link 184, network 180 and link 181, rather than via operator device 113, over short range communications 198, via device 113, link 183, network, 180 and link 181. Link 184 may connect directly to controller board 170, or as discussed in the embodiment of FIG. 3C, link 184 may implemented as a single communications link, such as a wired or wireless LAN link to a locker bank (locker bank 130 of FIG. 1A) which in turn may provide a wireless link, such as a short range Bluetooth link between a plurality controller boards comprising controller board 170, and link 184, thereby providing controller board 170 communications to server based system 111 over network 180. Alternatively, in an embodiment comprising both simple and intelligent locks, link 184 may implemented as a single communications link which in turn may provide a wireless link between one or more controller boards and one or more intelligent locks.

FIG. 3A and FIG. 3C depict intelligent locks 122e and 122a comprising lock access controller 128e and 128a, respectively. FIG. 3B and FIG. 3D depict simple locks 162e and 162f, and 162a and 162b, driven by lock controller boards 174 and 170 comprising lock access controller 176 and 172, respectively. Costs may be lower in configurations of locker banks where controller boards may support the use of lower cost simple locks. However, depending on restrictions and constraints in installation and configuration, some lockable compartments may be free standing or grouped in small numbers such that the wiring of a plurality or even a few simple locks to a controller board is not possible. In such cases, pairing a few simple locks to a controller board may actually cost more than using more expensive intelligent locks which do not require and whose use does not incur the expense of a controller board. Hybrid configurations comprising both intelligent locks, for the case of too few locks to offset the cost of a controller board, and controller board driven locks, for the case where a sufficient quantity of locks can be driven from one controller board and offset its cost, may be configured as needed to minimize costs.

Service events and access events as described in conjunction with FIG. 4A and FIG. 4B may be logged and recorded in server based system 111. FIG. 2B is an example illustration depicting an access event table 230 comprised by server based system 111, wherein access events may be recorded. Access events may comprise interactions with server based system 111, or locks, controller boards and lock access controllers thereof, wherein such interaction is associated with locks comprised by secure locker system 100 of FIG. 1A. Access event table 230 comprises an event ID column 234, event type column 236, access ID column 238, event time column 240, location ID column 242, locker ID column 244, lock ID column 246, accessor ID column 248 and event data column 250. Event ID column 234 comprises a unique identifier which is assigned to an access event and may be used to refer to a specific access event. Event type column 236 comprises classifications for access events such as, but not limited to, a request to invoke service mode, a request to access a compartment, a failed service mode attempt, a successful service mode attempt, a successful compartment access attempt, a failed compartment access attempt, a request to assign PIN, a successful request to assign PIN, a failed request to assign PIN, a cancel assigned PIN request, a PIN keypad entry, and the like. Access ID column 238 comprises identifiers assigned by server based system 111 to uniquely identify a successful or failed access attempt, namely, a lock opening or a failed attempt to open a lock. Event time column 240 comprises a data and time stamp for the event and may be specified by the entity reporting the event. Location ID column 242, locker ID column 244 and lock ID column 266 correspond to location ID column 210, locker ID column 212 and lock ID column 214 of lock access table 200. Accessor ID column 248 comprises a unique participant ID identifying the accessing entity, such as an operator initializing a lock or a user accessing property in a rented lockable compartment. Event data column 250 may comprise additional reported data such as data regarding a failed diagnostics test, a sequence number error, an access timer expiry that may be useful in diagnosing a root cause or support maintenance and service actions, or additional reported data that may be useful in documenting secure locker systems operations for future auditing and system improvement initiatives. In the example illustration of FIG. 2B access event table 230 is depicted comprising access event records 231, 232 and 233.

FIG. 2C is an example illustration depicting a lockable compartment access table 260 comprised by server based system 111. Lockable compartment access table 260 comprises lockable compartment access records created from lockable compartment access event records from table 230 and share some similar columns therewith, namely, access ID column 264, location ID column 270, locker ID column 272, lock ID column 274 and accessor ID column 276 correspond to access ID column 238 location ID column 242, locker ID column 244, lock ID column 246 and accessor ID column 248 of access event table 230. An access ID within access ID column 264 is assigned by server based system 111 to one or more access event records in table 230, and is a unique identifier for a successful or failed access attempt to a lockable compartment. Access type column 266 comprises a classification of lockable compartment access, such as but not limited to successful or failed access attempts of, an initial access associated with a new rental session, a terminating access associated with an ending of a rental session, an intervening access, an initialization access, a maintenance access, a cleaning access, and the like. Access data column 278 comprises event data from column 250 for one or more respective access event records comprising the access ID of a given lockable compartment access record, and may further comprise event type 236 and event time 240 column data. In this manner, a lockable compartment access record, or record of a failed attempt thereof, may comprise a complete account of submitted data for an access of a lockable compartment, or failed attempt thereof. The example illustration of lockable compartment access table 260 is depicted comprising three lockable compartment access records 261, 262 and 263.

Secure Locker System Rental and Access Application

Figure 5:
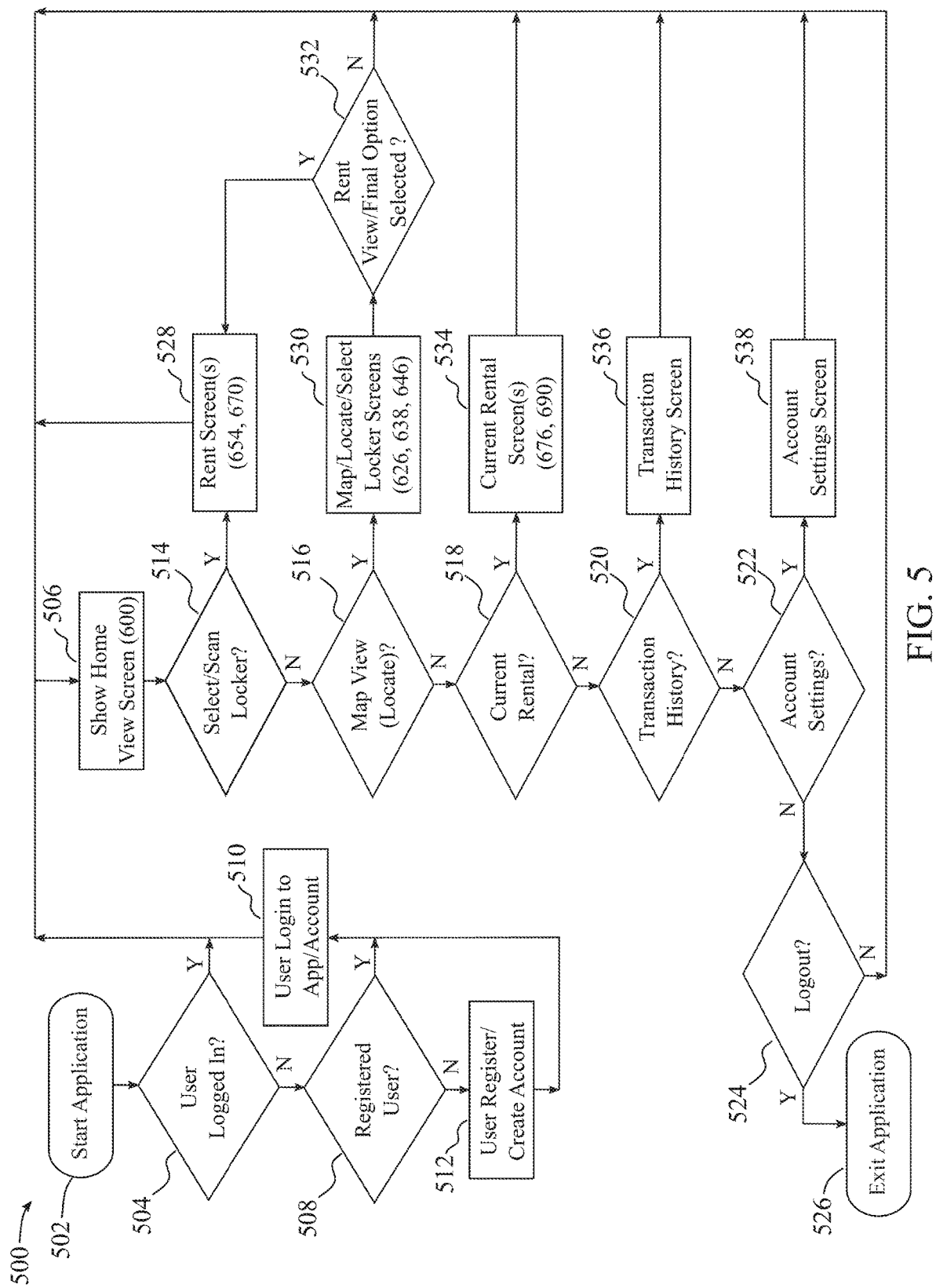
FIG. 5 is an example illustration depicting a flow diagram representation of a secure locker rental application.

Secure locker system 100 of FIG. 1A may comprise a rental application for download onto portable wireless devices and thereby permit users to interact with secure locker system 100 to rent and access a lockable compartment or access an otherwise assigned lockable compartment, or perform other related interactions such as search for available lockable compartments, terminate a locker rental and the like. Lockable compartments may comprise a barcode, such as a quick response barcode, or QR Code, such that users may use their portable wireless devices to quickly access information from server based system 111 related to the rental of a lockable compartment, download a rental application therefrom if desired and not already loaded, and establish an account therewith if desired and not already established. If the user already has the application downloaded, the application may indicate an availability status for the scanned lockable compartment, or a nearby lockable compartment available for rental. FIG. 5 is an example illustration depicting a flow diagram representation of a secure locker rental application 500. Application 500 is initiated or accessed in step 502 and first checks in step 504 to see if the user is logged into the system. If not the, a check is made in step 508 to see if the user has created a registered account. If the user does have a registered account, the user then may login in step 510. In not the user can create an account in step 512 and then login in step 510. Once logged into their account, the user is presented with the home view in step 506, where the user can choose from a plurality of actions, such as, select/scan a locker (step 514) to be presented with a rental screen (step 528), map view (step 514) to be presented with map/locate/select locker screens (step 530), current rentals (step 518) to be presented with a screen of their current rentals (step 534), transaction history (520) to review their transaction history (step 536), account settings (step 522) to review and update account settings (step 538) and logout (step 524) to exit the application (step 526).

Figures 6A, 6B:
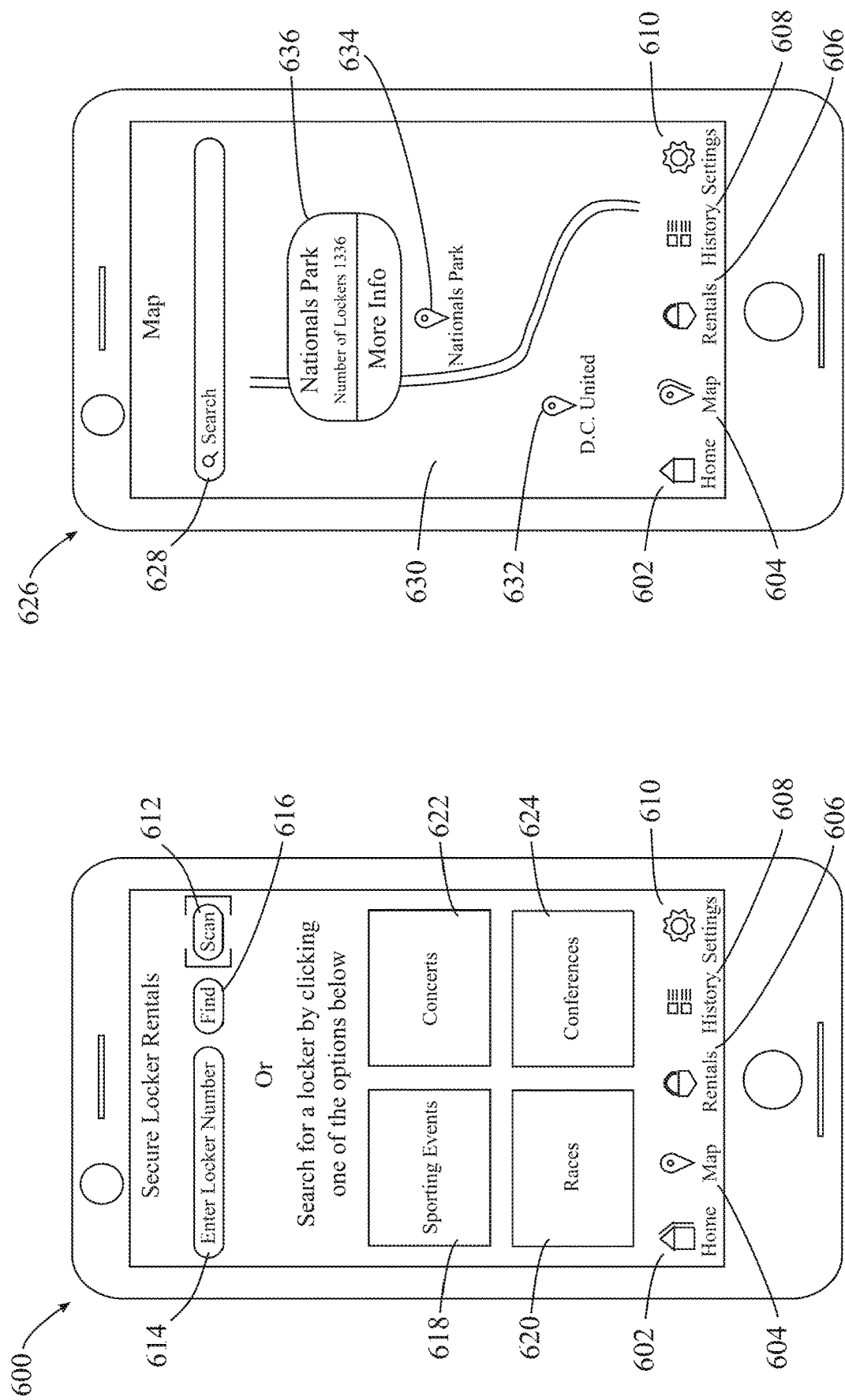
FIG. 6A is an example illustration depicting a home view screen of a secure locker rental application.
FIG. 6B is an example illustration depicting a map/locate screen of a secure locker rental application.

FIG. 6A through FIG. 6H depict illustrative user interface displays of screens which may be comprised by, and discussed in conjunction with, application 500 of FIG. 5 above. FIG. 6A depicts an illustrative home view screen 600 of step 506 and includes an enter locker number field 614, wherein a user can, for example, read and enter a locker number affixed to a lockable compartment and then select the find button 616. Screen 600 further comprises a scan locker button 612, wherein a user can, for example, scan a code affixed to a lockable compartment. In either case, the use of find button 616 or scan button 612, selects a locker (step 514) and presents a rent screen (step 528) for the user. A rental screen will be discussed later herein in conjunction with FIG. 6E. Home screen 600 also comprises a row of generally persistent navigational icons for major activities and functions within application 500. These icons are present on many of the various screens within application 500, thereby providing a generally persistent and common method for navigation to activities and functions associated therewith. In the example illustration of home screen 600, the icons comprise, a home icon 602 (step 506), a map icon 604 (steps 516, 530), a rentals icon 606 (steps 518, 534), a history icon 608 (steps 520, 536) and a settings icon 610 (steps 522, 538). Note that home icon 602 is highlighted, depicted as a double-image on its right side, to indicate that the present screen is home screen 600. As depicted in the example illustration of home screen 600, a user may also be presented with selections providing an option to review and search for lockers by event venue category, such as sporting events 618, races 620, concerts 622 and conferences 624.

Figure 6D:
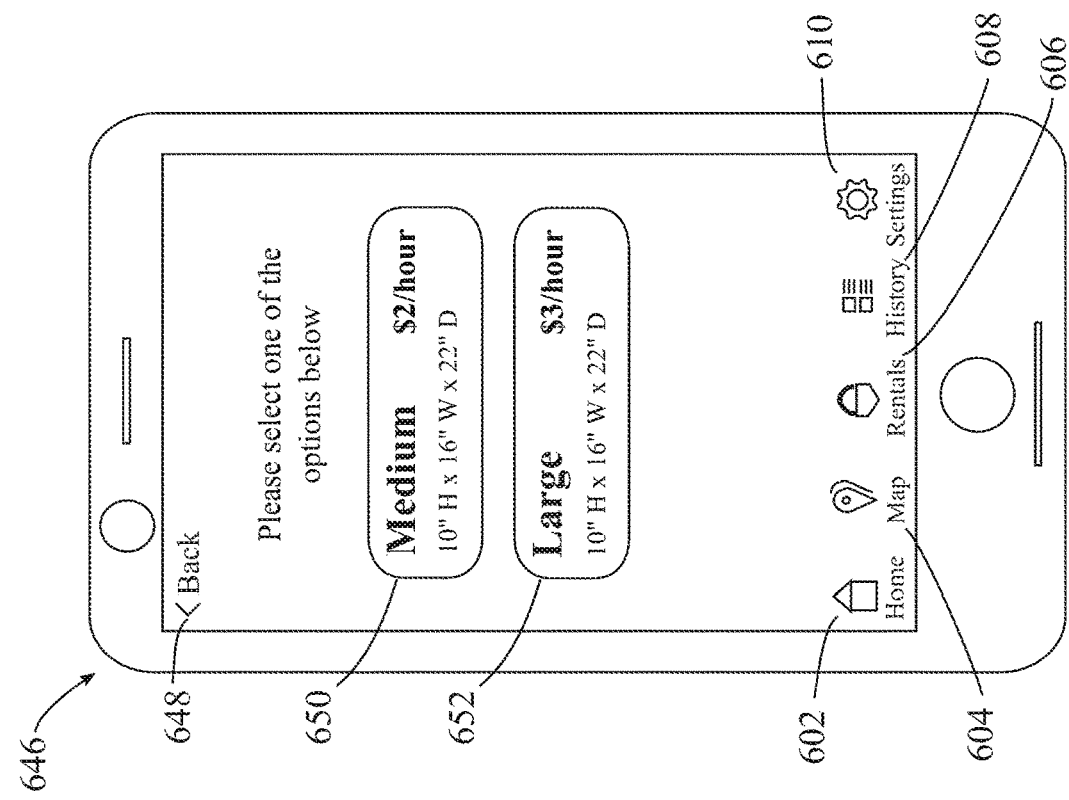
FIG. 6D is an example illustration depicting a selection screen of a secure locker rental application.
Figure 6C:
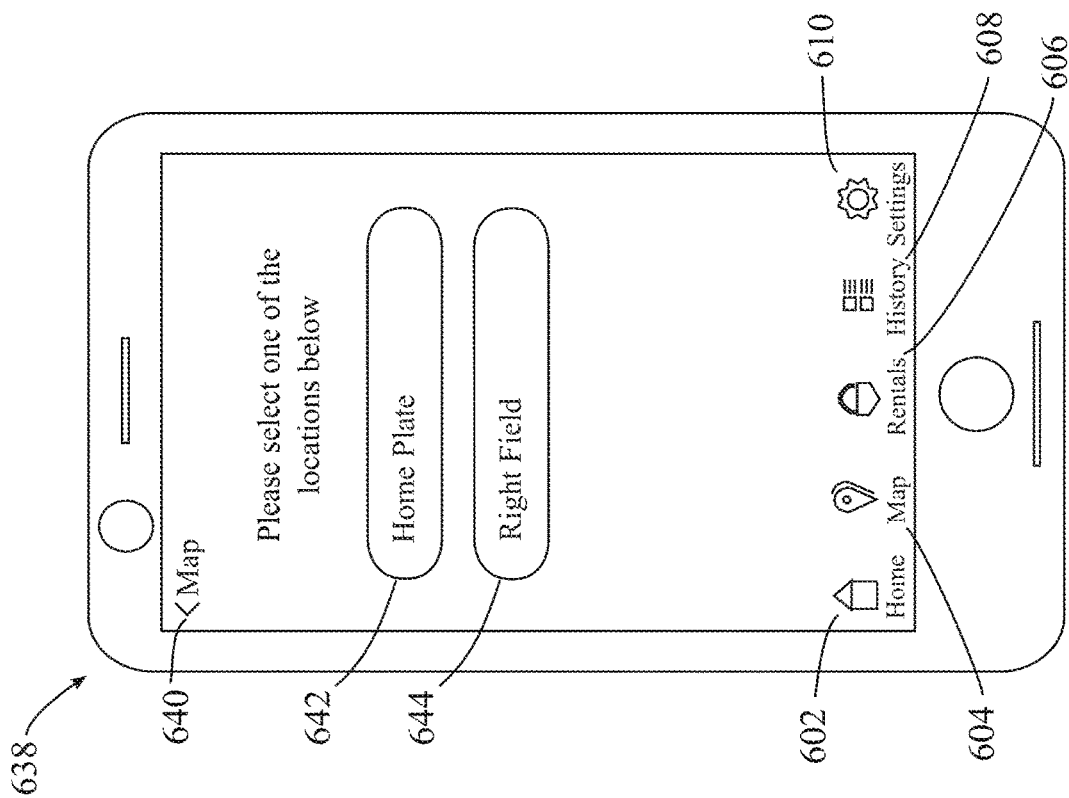
FIG. 6C is an example illustration depicting a selection screen of a secure locker rental application.

FIG. 6B depicts an illustrative map/locate screen 626 of step 530 resulting from a map selection in step 516, such as a user selecting map icon 604 on home screen 600 of FIG. 6A. Note that map icon 604 is highlighted, depicted as a double-image on its right side, to indicate that the present screen is map/locate screen 626. Also note that map icon 604 is represented by a commonly used map location pin or map marker icon. Map screen 626 can display a map 630, wherein map 630 may be manipulated in an interactive fashion by pinching fingers together on map 630 to zoom out and spreading fingers apart on map 630 to zoom in. Map 630 may be further manipulated by dragging a finger in a direction to pull the map center in a direction of the finger movement. Search entry field 628 may allow the entry of a map or geographic location, zip code, venue name, and the like, and cause a centering of the map to the corresponding coordinates of the entry if a map location is determined for the entry entered in search field 628. When map icon 604 is selected and map screen 626 is initially displayed in response, it can be centered based on current coordinates of a user's portable wireless device as ascertained by global positioning system (GPS) features which may be comprised by the portable wireless device. This may be particularly useful in a use case where a user has decided to research a location of a lockable compartment in which to unburden themselves of presently carried property and items, and would like to determine the nearest available lockable compartments. Search entry field 628 may be particularly useful in a use case where a user wants to research availability of lockable compartments near a planned future location. Lockable compartments in the example illustration of map screen 626 can be identified on map 630 as location pins 632 and 634. A selection of location pin 634 can cause a display of an information bubble 636 describing the location or venue and providing a selectable area to retrieve more info or additional information, as depicted in screen 626. FIG. 6C depicts an illustrative selection screen 638 which may be also be presented in step 530 when more info is requested in information bubble 636 of FIG. 6B. In the example illustration of screen 638, two locations of lockable compartments 642 and 644 are available at a venue corresponding to location pin 634 and are displayed to permit a user selection thereof. Aside from making a selection of locations 642 and 644, a user can select from the generally persistent navigational icons return home 602, map 604, current rentals 606, history 608 and settings 610. An alternative navigational option is to return to map screen 626 by selecting a back "<" to map selection 640. FIG. 6D depicts another illustrative selection screen 646 which may also be presented in step 530 in response to a selection of a location 642 and 644 on screen 638 of FIG. 6C. The example illustration of selection screen 646 depicts two possible size selections 650 and 652 for a medium and large lockable compartment, respectively. As depicted, selections 650 and 652 can provide dimensions and associated rental rates to assist in the user's selection thereof. Aside from making a selection of sizes 650 and 652, a user can select from the generally persistent navigational icons 602-610 or to return the previous selection screen 638 by selecting a back selection 648.

FIG. 6E depicts an illustrative rent screen 654 (step 528). The example illustration of rent screen 654 may have been arrived at after steps 530 and 532 when a final selection option has be made, wherein in the example illustration of FIG. 6D, a selection of a medium locker size 650 of selection screen 646 is indicated by the associated rental rate of $2/hour. Rent screen 654 (step 528) comprises an information window 658 indicating, by a locker number, a locker selected for rental and an hourly rate for a rental session. Additionally displayed are payment option selections 660, 662 and 664. A user may select a payment option 660, 662 and 664 in order to move forward with the rental, or alternatively return to the previous selection screen, size selection screen 646, by selecting a back selection 656 or select one of the generally persistent navigational icons 602-610. FIG. 6F depicts an illustrative rental confirmation screen 670 which may be displayed in response to a payment selection 660, 662 and 664 entered on rent screen 654. A user may either rent the indicated locker by selecting a yes selection 674, or decline the rental by selecting a no selection 672. Following either selection, the process may proceed from step 528 back to a home screen 600 view in step 506. Alternatively, in an embodiment, where the selection was a yes selection 674, the process may proceed directly to step 534 and display a current rentals screen 676 of FIG. 6G, which is discussed in more detail below.

Figure 6H:
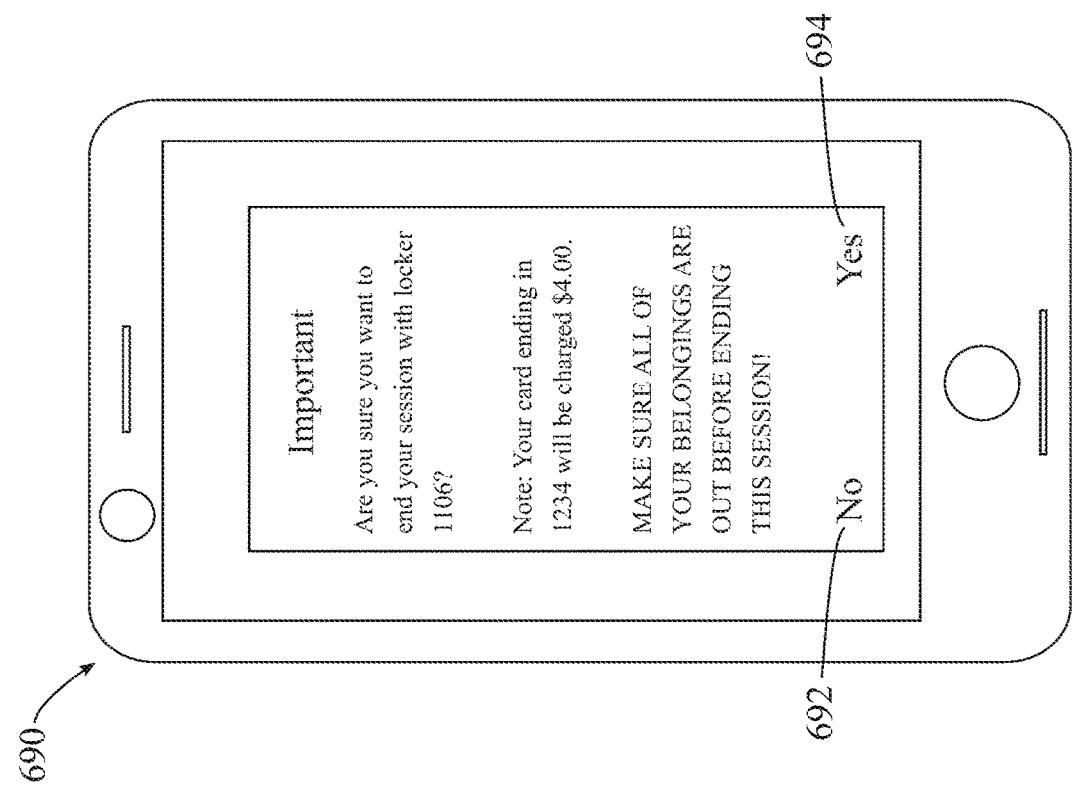
FIG. 6H is an example illustration depicting a confirmation screen of an end rental session function of a secure locker rental application.
Figure 6G:
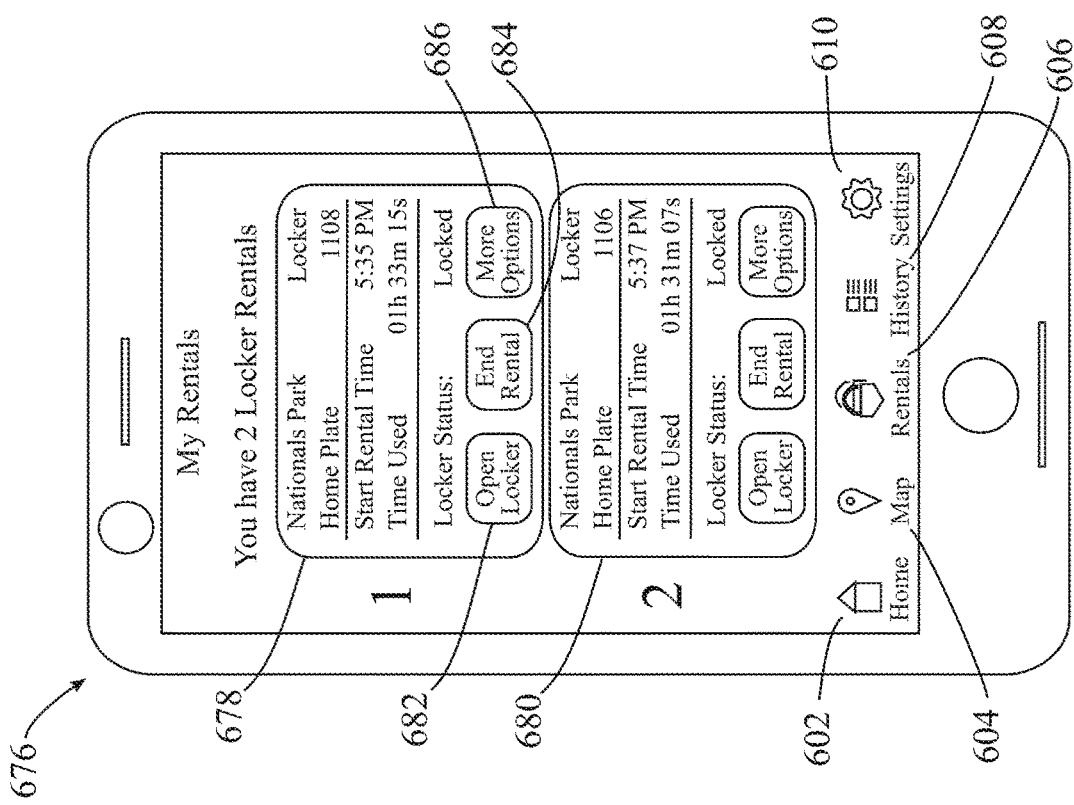
FIG. 6G is an example illustration depicting a current rentals screen of a secure locker rental application.

FIG. 6G depicts an illustrative current rentals screen 676 of step 534 resulting from a current rentals selection in step 518, such as a user selecting rentals icon 606 on home screen 600 of FIG. 6A, or as in an embodiment noted above, a yes selection 694 on rental confirmation screen 670. Note that current rentals icon 606 is highlighted, depicted as a double-image on its right side, to indicate that the present screen is current rentals screen 676. Current rentals screen 676 may provide a scrollable list of current locker rentals for a user. In the example illustration of screen 676, two current rentals, rental (1) 678 and rental (2) 680, are depicted. Information may be displayed regarding rental (1) 678, such as, the venue and location and location in the venue, locker number, rental start time, time used and locker status (e.g. locked or unlocked). Selection options to open locker 682, end rental 684 and more options 686 are provided. If open locker 682 is selected, open lockable compartment process 440 of FIG. 4B is initiated. Following an access of the lockable compartment, application 500 returns to home screen 600 in step 506. If end rental 684 is selected, a confirmation screen may be displayed, as will be discussed later herein. Selection of more options 686 can include access to help services and can include an assign user PIN selection as described earlier. Similar information and selection options are displayed for rental (2) 680. Current rental screen 676 further comprises the generally persistent navigational icons 602-610.

FIG. 6H depicts an illustrative confirmation screen 690 of an end rental session function which is displayed following a user selecting an end rental selection, such as end rental 684 of screen 676. A user may either continue with a termination of the rental by selecting a yes selection 694, or decline a termination of the rental by selecting a no selection 692. Following a no selection 692, the process may proceed back current rentals screen 676. Following a yes selection 694, an open lockable compartment process 440 of FIG. 4B is initiated. Following an access of the lockable compartment, application 500 returns to home screen 600 in step 506.

Similar to the secure locker system rental and access application 500 usable by users to interact with secure locker system 100 of FIG. 1A, a secure locker system operations application can be provided and usable by operators of secure locker system 100 to interact therewith. A secure locker operations application can be downloaded onto an operator device and be associated with an operator account comprised by server based system 100. An operator can be authenticated logging into their account similar to a user logging into an account associated with a secure locker rental and access application. A secure locker operations application can be used to initialize locks using process 400 of FIG. 4A, review maintenance and service requests among other operations related actions.

Secure Locker System Comprising Emergency Access

An operator of a secure locker system may operate a lockable compartments located at a plurality of locations and venues, and may be associated with a plurality of location operators and venue proprietors. A secure locker system operator may choose to additionally provide a localized redundancy of the functions and services remotely provided by a server based system. In this manner, should the remotely provided functions and services become unavailable to operate lockable compartments of a location or venue, a local server based emergency access system may be enabled as failover services such that patrons of affected lockable compartments have continued use and access thereof.

Referring again to FIG. 1A, in an embodiment, secure locker system 100 may additionally comprise one or more appliances or server based emergency access systems 119a, 119b and 119c, each of which may comprise one or more servers, software services and data services. Each appliance or server based emergency access system, also referred to more briefly as an emergency access system, may be, but is not necessarily, located at or in proximity of a location or venue comprising a secure locker operation, and may be associated therewith and provide uninterrupted locker access operations in the event that server based system 111 is not functional, is not accessible or is otherwise unavailable to support access of lockable compartments associated therewith. Emergency access systems 119a, 119b and 119c of FIG. 1A further comprise communications links 189a, 189b and 189c, respectively, to communications network 180 and are thereby accessible by a plurality of devices and systems.

Of notable difference from challenge codes and verification codes used in lock access and lockable compartment access process 440 of FIG. 4B previously disclosed herein, emergency challenge codes and emergency verification codes are used in an emergency lock access process, and are generated using emergency access input codes and emergency access derivation keys. An emergency access system comprises a lock emergency access table similar to lock access table 200 of FIG. 2A comprised by server based system 111, and FIG. 2A is suitable as a reference for a discussion of a lock emergency access table. Referring to FIG. 2A, lock emergency access tables comprised by emergency access systems 119a, 119b and 119c, comprise a location ID column similar to 210, a locker ID column similar to 212, a lock ID column similar to 214, an emergency access input code column similar to input code column 216, an emergency access derivation key column similar to derivation key column 218 and an emergency access sequence number column similar to sequence number column 220. Each lock associated with a lockable compartment supported by an emergency access system comprises an associated lock emergency access record in a lock emergency access table. Each lock emergency access record comprises an emergency access input code, an emergency access derivation key and an emergency access sequence number. A lock access controller of a lock or lock controller board supported by an emergency access system comprises for each associated lock an emergency access input code, emergency access derivation key and emergency access sequence number. A process to open a lock of a lockable compartment for emergency access thereof, is similar to process 440 of FIG. 4B to open a lock of a lockable compartment for access thereof, and FIG. 4B is suitable for reference in a discussion of an emergency access process.

For explanatory purposes of an emergency access process, referring to FIG. 1A, let the following scenario apply: server based system 111 is not available; portable wireless device 150 is in communication with emergency access system 119a which is collocated with locker bank 130, wherein communication is via communications link 186, network 180 and communications link 189a; and a user of portable wireless device 150 is accessing lockable compartment 120a of locker bank 130. An emergency open lockable compartment process 440 of FIG. 4B begins in step 442 and in step 444 a user of a portable wireless device 150 selects an open locker selection in order to access lockable compartment 120a. In step 446, portable wireless device 150 checks to see if it is connected to lock 122a, via a wireless short range connection 190. Once connected, in step 448, portable wireless device 150, sends an emergency open lock request to emergency access system 119a via communication links 186 and 189a and network 180, and sends an initiate emergency access command to lock 122a. The initiate emergency access command prompts lock access controller of lock 122a in step 450 to start a lock access timer which may be used to limit the usable lifetimes of generated single use emergency access authentication codes, namely, the useable lifetime of an emergency challenge code and the useable lifetime of an emergency verification code of the current lock emergency access attempt. Further in step 450, lock access controller of lock 122a retrieves an emergency derivation key and emergency input code for lock 122a and an emergency verification code generator of the lock access controller generates an emergency verification code, per the single use access authentication code equation disclosed earlier herein and restated here for an emergency access operation:

Emergency Code($n$)=$E$[Emergency Code($n$−1), ECDK]

Where:
Emergency Code (1) is the next single use emergency access authentication code following the last generated emergency code,
Emergency Code ($n$−1) is the last generated single use emergency access authentication code,
E is a suitable encryption method such as AES and comprises as inputs the last generated emergency access authentication code, Emergency Code ($n$−1) as the emergency input code, and an emergency code derivation key, ECDK, and
ECDK is the emergency code derivation key which is used to encrypt the last generated single use emergency access authentication code, Emergency Code ($n$−1) as the emergency input code, to create the next emergency code, Emergency Code ($n$).

Once an emergency verification code is generated it is used to update the emergency input code and an emergency sequence number of lock access controller 122a is incremented. In step 452, emergency access system 119a retrieves from a lock emergency access table an emergency derivation key and emergency input code for lock 122a and an emergency challenge code generator of emergency access system 119a generates an emergency challenge code, per the above emergency access code equation. Once the emergency challenge code is generated it is sent to portable wireless device 150 and is also used to update the emergency input code for lock 122a of the emergency access table of emergency access system 119a. The emergency sequence number for lock 122a of the emergency access table of emergency access system 119a is incremented. In step 454, portable wireless device 150 sends via short range communications 190 an emergency open lock command and the emergency challenge code to lock 122a. In step 456, lock access controller of lock 122a compares the received emergency challenge code to the generated emergency verification code. In step 458, if they are not equal or the access timer started in step 450 has expired, the process proceeds to step 460, wherein lock 122*a* logs and reports to emergency access system 119*a* via portable wireless device 150 the failed lock emergency access transaction and process 440 ends in step 462.

In an embodiment, in step 452, an emergency sequence number of the lock emergency access table of emergency access system 119*a* may be included with the emergency challenge code from emergency access system 119*a*, and a similarly maintained emergency sequence number of the lock access controller of lock 122*a* may be used to determine an out of sequence condition between the generation of emergency challenge codes by emergency access system 119*a* and the respective generation of emergency verification codes by the lock access controller of lock 122*a*. If in step 456, the lock access controller of lock 122*a* comprises a sequence number reporting a number of fewer code generation cycles it can "cycle" emergency verification codes until it evens up the sequence numbers to resolve the discrepancy and potentially achieve a matching of the emergency challenge code and the emergency verification code. If in step 456 lock access controller of lock 122*a* comprises an emergency sequence number reporting a number of greater emergency code generations it can request emergency access system 119*a*, via portable wireless device 150, to "cycle" emergency challenge codes until it evens up the emergency sequence numbers to resolve the discrepancy and potentially provide a successful emergency challenge code.

In step 458, if the emergency challenge code matches the emergency verification code, and the access timer started in step 450 is active and has not expired, then process 440 proceeds to step 464, wherein the lock access controller of lock 122*a* can actuate a lock bolt to open the lockable compartment, and indicate such actuation and opening via indicator 126*a*. Further in step 464, lock access controller of lock 122*a* logs and reports to emergency access system 119*a* via portable wireless device 150 the successful lock access transaction. Process 440 then proceeds to step 466 where process 440 ends.

A user may wish to store their portable wireless device in a lockable compartment for which they have a rental session, or for which they have an assigned use thereof. In an embodiment where a lock comprises or is otherwise connected to a keypad such as keypad 124*b* connected to lock 122*b* (FIG. 1A), a user may submit a request to assign a user PIN (request to assign PIN) and select a PIN on portable wireless device 150. When server based system 111 is unavailable and emergency access system 119*a* is actively servicing locker access requests, the request results in the generation and submission of an emergency challenge code as described above in conjunction with FIG. 4B. The assign user PIN submission by portable wireless device 150 with the selected PIN in combination with a successful emergency challenge code to lock 122*b*, will cause lock access controller of lock 122*b* for the duration of the present rental session or assignment to accept a correctly entered user PIN via keypad 124*b*, actuate a lock bolt to open lock 122*b* and actuate a visual indicator 126*b* to indicate a successful opening, as if a matching of an emergency verification code and emergency challenge code had occurred in conjunction with an emergency access request. If a user suspects their selected PIN may have been compromised, they can submit another assign user PIN request and select another PIN on their portable wireless device, or submit a request to cancel and deactivate their current access PIN, should they determine they no longer want or need the capability of access via keypad 124*b*. Upon an access in conjunction with a termination of a rental session or assignment, emergency access system 119*a* submits via portable wireless device 154 a request to cancel and deactivate the access PIN.

In normal operations, when server based system 111 is available, active rental session records, also called active rental contracts for lockable compartments also serviced by an emergency access systems 119*a*, 119*b* and 119*c* are communicated by server based system 111 to the appropriate emergency access system 119*a*, 119*b* and 119*c*. As such, should server based system 111 become unavailable, emergency based systems 119*a*, 119*b* and 119*c* can continue to provide access per the currently active rental contracts within their system. When a portable wireless device establishes a rental contract for a lockable compartment, server based system 111, checks to see if the contracted compartment is associated with an emergency access system and, if it is, sends a record of the contract thereto. Additionally, server based system 111 can send the failover URLs for the API services of the associated emergency access system to the portable wireless device and secure locker app running thereon upon entering into a rental contract. Should the API services of server based system 111 then become unavailable, the portable wireless device and secure locker system rental and access app running thereon, may then utilize the failover URLs for emergency access transactions.

In order to maintain a record of activity resulting from services provided by emergency access systems 119*a*, 119*b* and 119*c*, each system can maintain an emergency access event table and emergency lockable compartment access table similar to access event table 230 and lockable compartment access table 260 maintained by server based system 111. When server based system 111 is available, records from the emergency access system event and access tables can be forwarded for recording in corresponding server based system 111 access event table 230 and lockable compartment access table 260, and can be given corresponding event type 236 and access type 266 classifications to denote services were provided by emergency access systems. Any deferred processing, such as submission of payment transactions, that was deferred until server based system 111 became available, can be processed after table 230 and table 260 are updated to reflect all activity processed and deferred by emergency access systems. Server based system can audit emergency access systems 119*a*, 119*b* and 119*c* by processing records from the emergency access system reported and recorded in tables 230 and 260, and can also request records comprising emergency sequence numbers for each lock within the lock emergency access table to validate consistency between reported emergency access records and the lock emergency sequence numbers and validate the completeness of reported records and activity. Furthermore, sequence numbers and emergency sequence numbers may both be appended by lock access controller to access event reports issued by locks via portable wireless devices, such as in step 464 of process 440 of FIG. 4B, to maintain an accurate and corroborated report of all system activity. Emergency access systems 119*a*, 199*b* and 199*c* may be implemented such that they require an administrator of secure locker system 100 to enable their use. In this way, an operator of secure locker system 100 can ensure that emergency access is only used when it is appropriate.

While a primary benefit of emergency access systems 119*a*, 119*b* and 119*c* is the continued servicing of existing rental contracts despite the unavailability of server based system 111, in an embodiment, emergency access systems 119a, 119b and 119c may additionally provide services to enable the initiation of new rental contracts despite the unavailability of server based system 111. When server based system 111 is available, rental contracts initiated within the emergency access system can be forwarded for recording by server based system 111 and any required processing, such as closure of rental contracts and submission of payment transactions that were deferred until server based system 111 became available.

In an embodiment, an emergency access device, similar to operator device 113 can be provided. An emergency access device may have limited functionality comparable to an operator device 113. For example, an emergency access device may not be capable of initializing a lock. A primary use of an emergency access device may be to access a lockable compartment when prior attempts using a user's portable wireless device have failed. An emergency access device may be retained by a local operator to assist such a user to access their rented lockable compartment. The emergency access device can attempt access using the user credentials for the secure locker system as entered by the user, and potentially other procedures to validate the user authenticity such as an authentication code sent to an email account of the user. Once the user is authenticated by server based system 111, a lock access command is initiated and a challenge code is generated using a derivation key and an input code for the associated lock. If this access attempt fails, and provided the user was authenticated by server based system 111, the server based system can then request directly to an associated emergency access system, emergency access to the lockable compartment. If this attempt is successful, the lockable compartment can be retired from current service after this access and scheduled for repair procedures, such as a lock (re)initialization procedure. If the server based system 111 is unavailable, the operator of the emergency access device may be required to receive and enter a permission code from the secure locker system operator to enable an emergency access command to access the lockable compartment using the emergency access system. The provision of the permission code for such emergency access should be restricted and require procedures that ensure only a legitimate user receives such emergency access.

Similar to the initialization of locks for use with server based system 111, locks are initialized for use with emergency access systems 119a, 119b and 119c. This process is similar to lock initialization process 400 of FIG. 4A, and may be combined into a single process flow wherein a lock may be initialized for use in both server based system 111 and an emergency access system in the same process using operator device 112 and 113. As such, the code derivation key and input code of Table 1 and Table 2, respectively, are generated in component parts and shared between the initialized lock and server based system 111, and an emergency derivation key and emergency input code are generated in component parts and shared between the initialized lock and emergency access system. The relationship between exchanged emergency derivation key component values, public/private key pairs and the assembled shared emergency derivation key is shown in Table 3 below. For explanatory purposes, this parallel process will be discussed considering operator device 113, lock 122a and emergency access system 119a. The operator device 113 or lock 122a lock access controller generated components can be referred to as a lock emergency derivation key component, or lock emergency key component, and lock emergency input code component and the emergency access system generated components can be referred to as an emergency system code derivation key component, or emergency system key component, and an emergency system input code component.

TABLE 3

Secure Exchange of Emergency Key Components for Shared Key Generation

| Operation | Operator Device or Lock Access Controller | Emergency Access System |
| --- | --- | --- |
| Randomly Generate Emergency Key Component | LoEmKComp | EAEmKComp |
| Encrypt Emergency Key Component | E [LoEmKComp, EAPuK] | E [EAEmKComp, OpPuK] |
| Decrypt Received Emergency Key Component | D [$\overline{\text{EAEmKComp}}$, OpPrK] | D [$\overline{\text{LoEmKComp}}$, EAPrK] |
| Generate/Assemble Emergency Key | A [LoEmKComp, EAEmKComp] | A [LoEmKComp, EAEmKComp] |

Where:

LoEmKComp is the lock emergency key component, $\overline{\text{LoEmKComp}}$ is the encrypted lock emergency key component, EAEmKComp is the emergency system key component, $\overline{\text{EAEmKComp}}$ is the encrypted emergency system key component, OpPuK is the operator device public key, OpPrK is the operator device private key, EAPuK is the emergency access system public key, and EAPrK is the emergency access system private key.

The relationship between exchanged emergency input code component values, public/private key pairs and the assembled shared emergency input code is shown in Table 4 below.

TABLE 4

Secure Exchange of Emergency Input Code Components
for Shared Emergency Input Code Generation

| Operation | Operator Device or Lock Access Controller | Emergency Access System |
|---|---|---|
| Randomly Generate Emergency Input Code Component | LoEmICComp | EAEmICComp |
| Encrypt Emergency Input Code Component | E [LoEmICComp, SyPuK] | E [EAEmICComp, OpPuK] |
| Decrypt Received Emergency Input Code Component | D [$\overline{\text{EAEmICComp}}$, LoPrK] | D [$\overline{\text{LoEmICComp}}$, SyPrK] |
| Assemble Emergency Input Code | A [LoEmICComp, EAEmICComp] | A [LoEmICComp, EAEmICComp] |

Where:

LoEmICComp is the lock emergency input code component, $\overline{\text{LoEmICComp}}$ is the encrypted lock emergency input code component, EAEmICComp is the emergency system seed component, $\overline{\text{EAEmICComp}}$ is the encrypted emergency system seed component, OpPuK is the operator device public key, OpPrK is the operator device private key, EAPuK is the emergency access system public key, and EAPrK is the emergency access system private key.

Operator device 113 exchanges public keys of respective public/private key pairs with server based system 111 and emergency access system 119a either prior to or upon initiation of the parallel lock initiation process. Referring to FIG. 4A as a similar process and useful reference to explain the parallel system lock initialization, the process begins in step 402. In step 404 operator device 113 attempts to establish a secure connection 198 with lock 122a using a secure Bluetooth communication protocol, for example a Bluetooth security level 4, security mode 2 secure connection, as described in NIST Special Publication 800-121, Revision 2, published May 2017. In step 406, once secure short range connection 198 is established, the process moves to step 408, wherein operator device 113 issues a service mode command to lock 122a. This command can result in multiple process steps not depicted in FIG. 4A, such as, indicating, via communications links 183 and 181 and network 180, a service mode request to server based system 111 requesting to put lock 122a into a service mode, and receiving in response a challenge code and an encrypted sequence number as a secure service mode token, wherein the encrypted sequence number is encrypted using the code derivation key. Referring to the example illustration of lock access table 200 of FIG. 2A, to prepare this response comprising a challenge code and encrypted sequence number, server based system 111 retrieves from record 201 an input code, derivation key and sequence number. For locks not previously initialized and put into use, these values may be based on keys, codes and sequence numbers created during a lock access controller production process, and may be unique or default values. Server based system 111 then encrypts the input code, which may simply be a default input code entered during manufacturing, using the derivation key to generate a challenge code needed for the pending service mode command. Server based system 111 encrypts the sequence number using the derivation key to generate an encrypted sequence number which is also needed as a secure service mode token for the pending service mode command. Server based system 111 then responds to operator device 113 with the required challenge code and encrypted sequence number. Operator device 113 then issues to lock 122a via short range connection 198 the service command comprising the challenge code and encrypted sequence number. Lock access controller of lock 122a, maintains data corresponding to record 201 comprising an input code, derivation key and sequence number, and independent of server based system 111 generates a verification code and encrypted sequence number (or alternatively decrypts the received encrypted sequence number). In step 410, if the verification code matches the challenge code and the received encrypted sequence number matches the lock generated encrypted sequence number (or alternatively the decrypted received sequence number matches the lock sequence number), the lock successfully enters service mode and the lock opens, wherein a lock bolt retracts and an indicator 126a may indicate a successful entry into service mode (e.g., flashing a green color and/or sounding a brief tone). If in step 410, the verification code and challenge code do not match, or the received encrypted sequence number and lock generated encrypted sequence number do not match (or alternatively the decrypted received sequence number does not match the lock sequence number), then the service mode command fails, indicator 126a may indicate a failed entry into service mode (e.g., flashing a red color and/or sounding a long tone), and in step 424, the process reports the failure to server based system 111 and ends in a failed initialize lock process in step 426. In an embodiment, in step 410, if the verification code and challenge code do not match, the received encrypted sequence number may be decrypted and used to determine an out of sequence condition between the server based system 111 generation of challenge codes and the respective generation of verification codes by lock access controller of lock 122a. If lock access controller of lock 122a comprises a sequence number reporting a number of fewer code generation cycles it can "cycle" verification codes until it evens up the sequence numbers to resolve the discrepancy and potentially achieve a matching of the challenge code and verification code. If lock access controller of lock 122a comprises a sequence number reporting a number of greater code generations it can request server based system 111, via operator device 113, "cycle" challenge codes until it evens up the sequence numbers to resolve the discrepancy and potentially provide a successful challenge code.

Upon successful entry into service mode in step 410, the combined server based system 111 and emergency access system 119a initialization process generates a new shared secret derivation key and a new shared secret input code by the independent generation, encryption and secure mutual exchange of encrypted key components and encrypted input code components by server based system 111 and operator device 113 or lock access controller of lock 122a as previously described, and further generates a new shared secret emergency key and a new shared secret emergency input code by the independent generation, encryption and secure mutual exchange of encrypted emergency key components and encrypted emergency input code components by emergency access system 119a and operator device 113 or lock access controller of lock 122a as will now be described. In step 412 of the combined embodiment of process 400, operator device 113 or lock access controller of lock 122a generates the encrypted lock key component, $\overline{\text{LoDKComp}}$, per Table 1 above, and the encrypted lock input code component, $\overline{\text{LoICComp}}$, per Table 2 above, and sends them to the server based system 111. For explanatory purposes, an embodiment where lock access controller of lock 122a generates the components will be described. Operator device 113 sends the server based system public key, SyPuK, to lock access controller of lock 122a. Lock access controller of lock 122a using a pseudo random number generator generates a lock key component, LoDKComp, and a lock input code component, LoICComp. Then using SyPuK, lock access controller of lock 122a encrypts the components thereby generating $\overline{\text{LoDKComp}}$ and $\overline{\text{LoICComp}}$ which it sends to operator device 113 for secure communication to server based system 111. Server based system 111 may then decrypt these components using SyPrK, the server based system 111 private key and reserve them for final assembly of the new shared code derivation key and new shared input code for lock 122a. Next, operator device 113 sends the emergency access system 119a public key, EAPuK, to lock access controller of lock 122a. Lock access controller of lock 122a using a pseudo random number generator generates a lock emergency key component, LoEmKComp, and a lock emergency input code component, LoEmICComp. Then using the EAPuK, lock access controller of lock 122a encrypts the components thereby generating $\overline{\text{LoEmKComp}}$ and $\overline{\text{LoEmICComp}}$ which it sends to operator device 113 for secure communication to emergency access system 119a. Emergency access system 119a may then decrypt these components using EAPrK, the emergency access system 119a private key and reserve them for final assembly of the new shared emergency key and new shared emergency input code for lock 122a.

In step 414 of the combined embodiment of process 400, server based system 111 using a pseudo random number generator generates a system key component, SyDKComp, and a system input code component, SyICComp. Then using the OpPuK, server based system 111 encrypts the components thereby generating $\overline{\text{SyDKComp}}$ and $\overline{\text{SyICComp}}$ which it sends to operator device 113. Server based system 111 may now in step 416 assemble the new shared code derivation key from the component parts, A [LoDKComp, SyDKComp], and the new shared input code from the component parts, A [LoICComp, SyICComp], and load them into the derivation key and input code of record 205 of lock access table 200. Operator device 113 receives and then decrypts $\overline{\text{SyDKComp}}$ and $\overline{\text{SyICComp}}$ using OpPrK and sends the resulting SyDKComp and SyICComp to lock access controller of lock 122a. In step 418, lock access controller of lock 122a may now assemble and store therein the new shared code derivation key per Table 1 above from the component parts, A [LoDKComp, SyDKComp], and the new shared input code per Table 2 above from the component parts, A [LoICComp, SyICComp] for use in future service and access requests. Next, in the combined embodiment of process 400, emergency access system 119a using a pseudo random number generator generates an emergency key component, EAEmKComp, and an emergency input code component, EAEmICComp. Then using the operator device public key, OpPuK, emergency access system 119a encrypts the components thereby generating $\overline{\text{EAEmKComp}}$ and $\overline{\text{EAEmICComp}}$ which it sends to operator device 113. Emergency access system 119a may now in step 416 assemble the new shared emergency key per Table 3 above from the component parts, A [LoEmKComp, EAEmKComp], and the new shared emergency input code per Table 4 above from the component parts, A [LoEmICComp, EAEmICComp], and load them into lock emergency access table emergency key and emergency input code, respectively, for the record associated with lock 122a. Operator device 113 receives and then decrypts $\overline{\text{EAEmKComp}}$ and $\overline{\text{EAEmICComp}}$ using OpPrK and sends the resulting EAEmKComp and EAEmICComp to lock access controller of lock 122a. In step 418, lock access controller of lock 122a may now assemble and store therein the new shared emergency key from the component parts, A [LoEmKComp, EAEmKComp], and the new shared emergency input code from the component parts, A [LoEmICComp, EAEmICComp] for use in future emergency access requests.

In step 420 of the combined embodiment of process 400, operator device 113 issues a test lock command to verify the newly generated derivation key, input code, emergency key and emergency input code are operable and that the lock opens properly by first executing an access locker command, and then executing an emergency access locker command, and may also run other lock diagnostics, such as check a battery status or verify a memory checksum. If the lock does not open properly or certain diagnostic tests fail, then the initialization process fails. In step 424, the process reports the failure to server based system 111 and emergency access system 119a, and in step 426 ends in a failed initialize lock process. Note that some diagnostic test failures, may be resolved, for example, the battery may be replaced, after which the diagnostic test and initialization process may then pass. If in step 422 the lock opens and the diagnostics test pass, then the successful initialization of lock 122a is reported to server based system 111 and emergency access system 119a, and the combined embodiment of initialize lock process 400 ends in step 430. Note that the operator device 113 may also prompt the user to execute a check list of other lockable compartment 120a (FIG. 1A) tests and assessments, such as an assessment of whether the locker door 121a (FIG. 1A) moves freely, locker interior is clean and free of debris, etc., and if appropriate allow or disallow lockable compartment 120a to be put into service.

Secure Locker System with Collapsible Lockable Compartments and Secure Storage Platform Demand for secure temporary storage can be closely related to events and can vary depending on factors such as weather, the day of the week, time of day, event location, event popularity, and many other factors. For example, a sporting event on a weekday, starting near the end of the workday, and near a busy metropolitan area will likely be attended by many people wanting to store business and other workday items. Other events are temporary in nature and permanent or semi-permanent secure storage lockers may not be practical. Given the fluctuation in demand and temporary nature of many events, secure storage lockers that may be easily and compactly transported to a location when needed, and easily set up and taken down to be once again transported are desirable. Predictive analytics can be used to track such factors as those mentioned above and forecast needs for supplemental lockable compartments to be dispatched from regionally placed inventories. This helps to insure that customers can become accustomed to having available storage and promotes frequent purchasing of secure storage services.

Figure 7F:
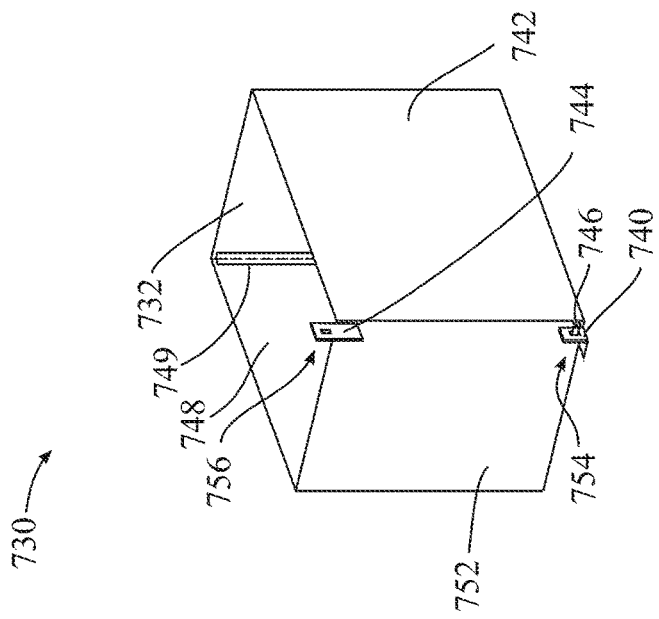
FIG. 7F is an example illustration depicting a folded collapsible and foldable base.
Figure 7D:
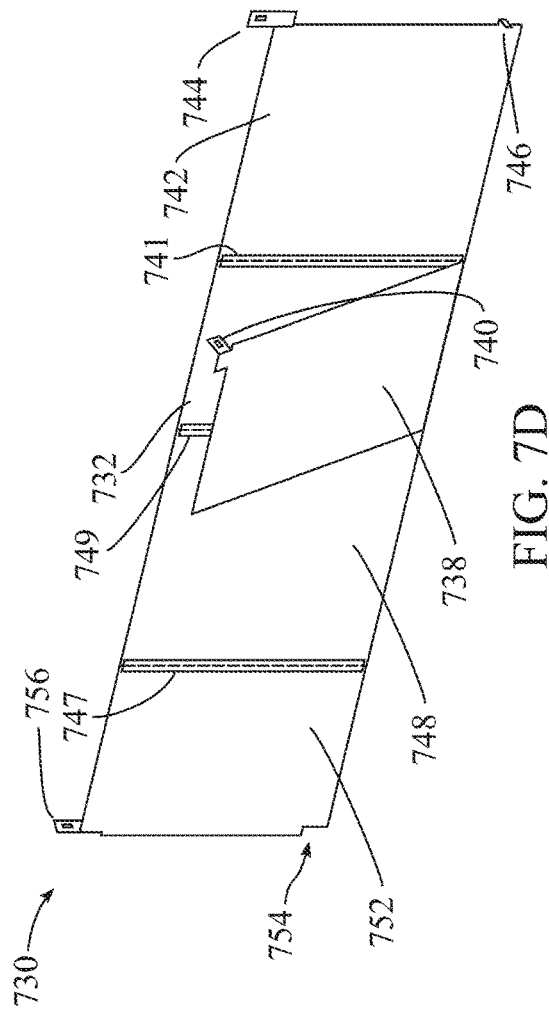
FIG. 7D is an example illustration depicting an unfolded collapsible and foldable base.
Figure 7E:
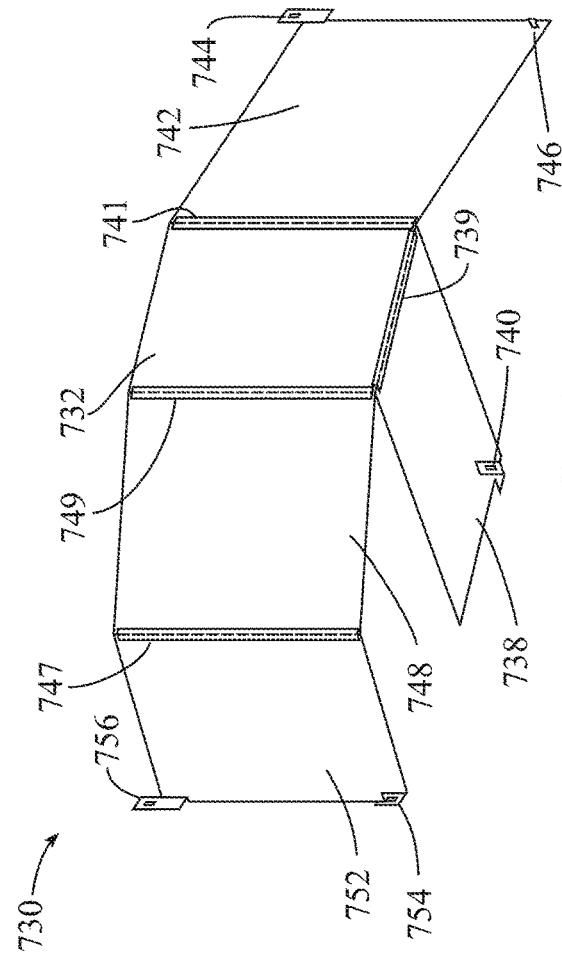
FIG. 7E is an example illustration depicting a partially folded collapsible and foldable base.
Figure 7H:
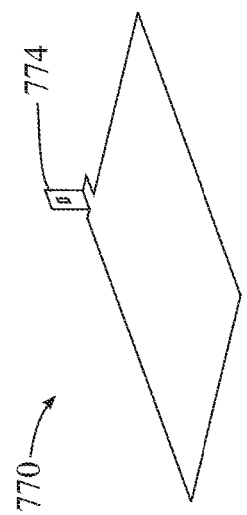
FIG. 7H is an example illustration depicting a top panel for the stack assembly of FIG. 7G.
Figure 7G:
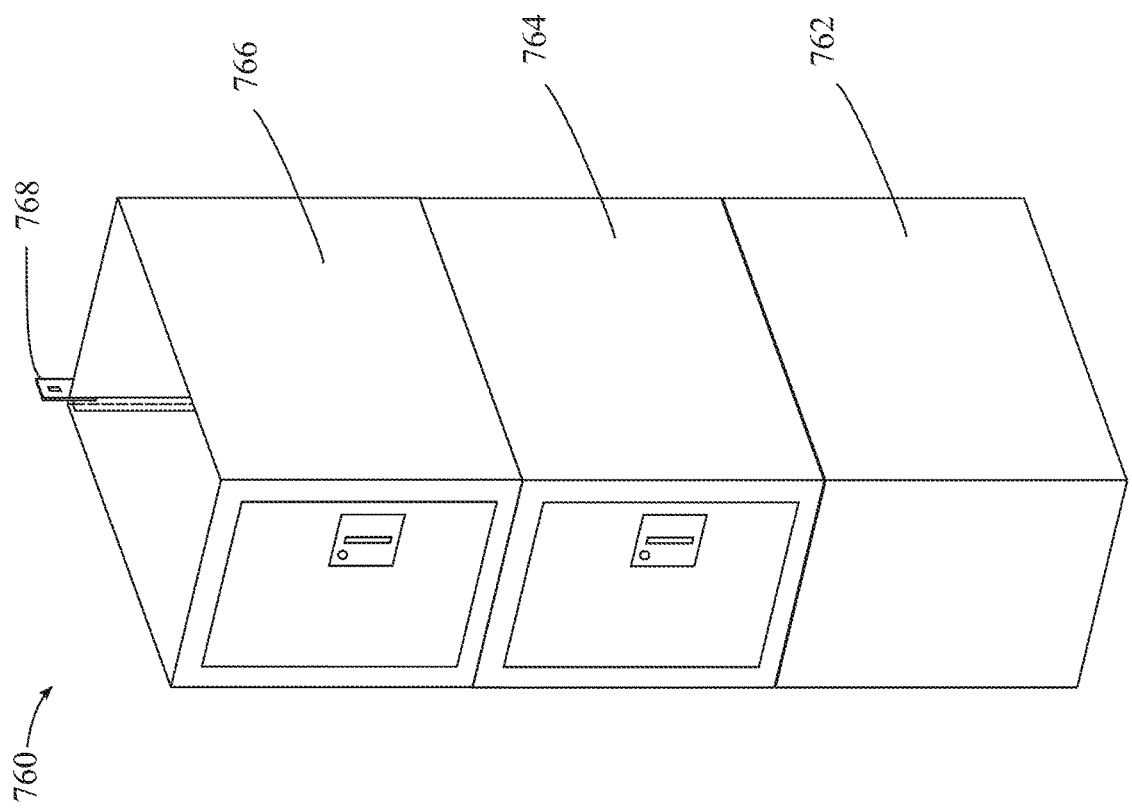
FIG. 7G is an example illustration depicting a locker stack assembly.

Secure locker systems can be configured for use with a portable, collapsible locker system. FIG. 7A, FIG. 7B and FIG. 7C are example illustrations depicting a collapsible and foldable lockable compartment 700. FIG. 7D, FIG. 7E and FIG. 7F are example illustrations depicting a collapsible and foldable base 730 on which one or more collapsible lockable compartments 700 may be placed in a stacked manner thereby forming a vertical locker stack assembly. FIG. 7G is an example illustration depicting a locker stack assembly 760 comprising a base 762, a first locker 764 and a second locker 766 which may receive a top component 770 of which an example illustration is depicted in FIG. 7H. Vertical stack assembly 760 may be situated with other vertical stacks to produce a locker bank. The collapsible lockable compartment 700 of FIGS. 7A, 7B and 7E, collapsible base 730 of FIGS. 7D, 7E and 7F, and top component 770 of FIG. 7H may be easily and compactly transported to a location when needed, and easily set up and taken down to be once again transported in order to address temporary and dramatically fluctuating demands associated with temporary secure storage. Furthermore, temporary secure storage arrangements can be flexibly configured to comprise individual lockers 700, stack assemblies 760 and locker banks.

Referring to FIG. 7A and FIG. 7B in more detail, collapsible locker 700 comprises a front panel which is a frame 702 comprising a door 704, attached thereto by a hinge 703. Left side panel 712 and right side panel 718 (when assembled and viewing front panel 702) are attached to front panel 702 with hinges 711 and 719, respectively. Back panel 722 is attached to right side panel 718 with hinge 717. Bottom panel 708 is attached to front panel 702 with hinge 709 (visible and referenced in FIG. 7B). Collapsible locker 700 further comprises a rear panel lower fastening tab 724, a bottom panel fastening tab 710, a rear panel upper fastening tab 726, a left side panel upper fastening tab 714 and a left side panel lower fastening pin 716. When assembled as in FIG. C, pin 716 passes through bottom panel fastening tab 710 and rear panel tab 724, thereby securing bottom panel tab 710 between side panel pin 716 and rear panel tab 724. As will be shown in more detail later, when two collapsible lockers are assembled in a stacked orientation, upper tabs 726 and 714 of a first locker may be secured between pin 716 and tab 710 of a second locker situated above the first locker. Collapsible locker 700 further comprises an electromechanical lock 706 attached to door 704 and comprising a locking element, locking bolt 705, and a lock bolt latch 707, attached to front panel frame 702. Lock bolt attaches and releases door 704 from front panel frame 702, wherein lock bolt 705 may travel past an edge of lock bolt latch 707 and front panel frame 702 to lock door 704 in a closed position, and be retracted to unlock door 704.

Referring to FIG. 7D, FIG. 7E and FIG. 7F, collapsible base unit 730 is similar in construction to that of collapsible locker 700 with a primary difference being a front panel 732 that does not comprise a door and lock assembly. Left side panel 742 and right side panel 748 (when assembled and viewing front panel 732) are attached to front panel 732 with hinges 741 and 749, respectively. Back panel 752 is attached to right side panel 748 with hinge 747. Bottom panel 738 is attached to front panel 732 with hinge 739 (visible and referenced in FIG. 7E). Collapsible locker 730 further comprises a rear panel lower fastening tab 754, a bottom panel fastening tab 740, a rear panel upper fastening tab 756, a left side panel upper fastening tab 744 and a left side panel lower fastening pin 746. When assembled as in FIG. F, pin 746 passes through bottom panel fastening tab 740 and rear panel tab 754, thereby securing bottom panel tab 740 between side panel pin 746 and rear panel tab 754. As will be shown in more detail later, when a collapsible base 730 and collapsible locker 700 are assembled in a stacked orientation with the latter in the upper position, upper tabs 756 and 744 of base 730 may be secured between pin 716 and tab 710 of locker 700 situated on and above base 730. Referring to FIG. 7G, upper fastening tabs 768 of upper collapsible locker 766 of vertical stack assembly 760 (corresponding to fastening tabs 726 and 714 of locker 700) may be aligned with a left fastening tab 774 of top panel 770 when locker 766 receives top panel 770, and the tabs may be secured together with a lock hasp or locking bar as will be described later herein.

Figure 7N:
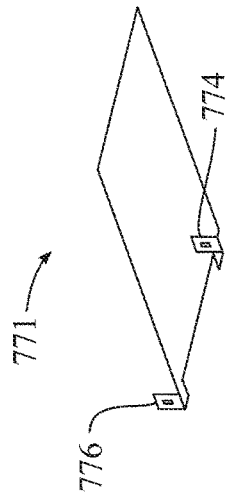
FIG. 7N is an example illustration depicting a top panel comprising an additional fastening tab.
Figure 7O:
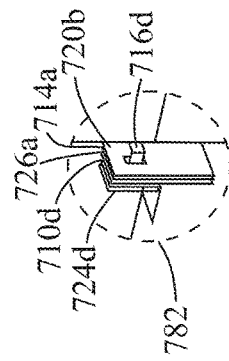
FIG. 7O is an example illustration depicting a joining point of three lockers.
Figure 7P:
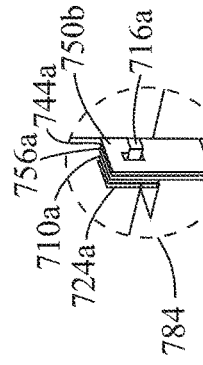
FIG. 7P is an example illustration depicting a joining point of two bases and one locker.

FIG. 7I and FIG. 7J are example illustrations depicting a collapsible locker 701. Locker 701 is similar to locker 700 and further comprises a right side panel upper fastening tab 720. FIG. 7K and FIG. 7L are example illustrations depicting a collapsible base 731. Base 731 is similar to base 730 and further comprises a right side panel upper fastening tab 750. Right side upper panel fastening tabs 720 and 750 may be used to interconnect adjacently situated vertical stack assemblies as in FIG. 7M. FIG. 7M is an example illustration depicting a partially assembled locker bank 780 comprising a plurality of collapsible lockers 701, collapsible bases 731 and top panels 771 of which an example illustration is depicted in FIG. 7N. Top panel 771 additionally comprises a right fastening tab 776 in addition to a left fastening tab 774 also comprised by top panel 770. Three joining points 782, 784 and 786 where fastening tabs may be secured together are shown in more detail in FIG. 7O, FIG. 7P and FIG. 7Q, respectively. FIG. 7O illustrates a joining point 782 for three collapsible lockers 701 wherein fastening tabs of three lockers of adjacent rows and columns are joined together with a common fastening pin, and in doing so results in two adjacent rows and two adjacent columns being secured together. Joining point 782 joins together fastening tabs from collapsible lockers 701a, 701b, and 701d. Referring to FIG. 7O, joining point 782 comprises rear panel lower fastening tab 724d of locker 701d, bottom panel fastening tab 710d of locker 701d, rear panel upper fastening tab 726a of locker 701a, left side panel upper fastening tab 714a of locker 701a and right side panel upper fastening tab 720b of locker 701b. Tabs 724d, 710d, 726a, 714a and 720b are joined together with left side panel lower fastening pin 716d. Referring now to FIG. 7P, FIG. 7P illustrates joining point 784 for two collapsible bases 731a and 731b, and collapsible locker 701a wherein fastening tabs of three units of adjacent rows and columns are joined together with a common fastening pin. Joining point 784 comprises rear panel lower fastening tab 724a of locker 701a, bottom panel fastening tab 710a of locker 701a, rear panel upper fastening tab 756a of base 731a, left side panel upper fastening tab 744a of base 731a and right side panel upper fastening tab

750b. Tabs 724a, 710a, 756a, 744a and 750b are joined together with left side panel lower fastening pin 716a of locker 701a.

Figure 7Q:
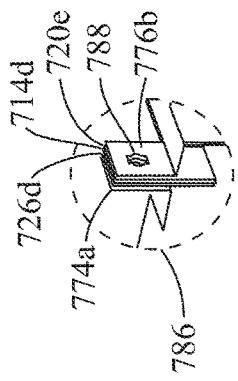
FIG. 7Q is an example illustration depicting a joining point of two lockers and two top panels.
Figure 7M:
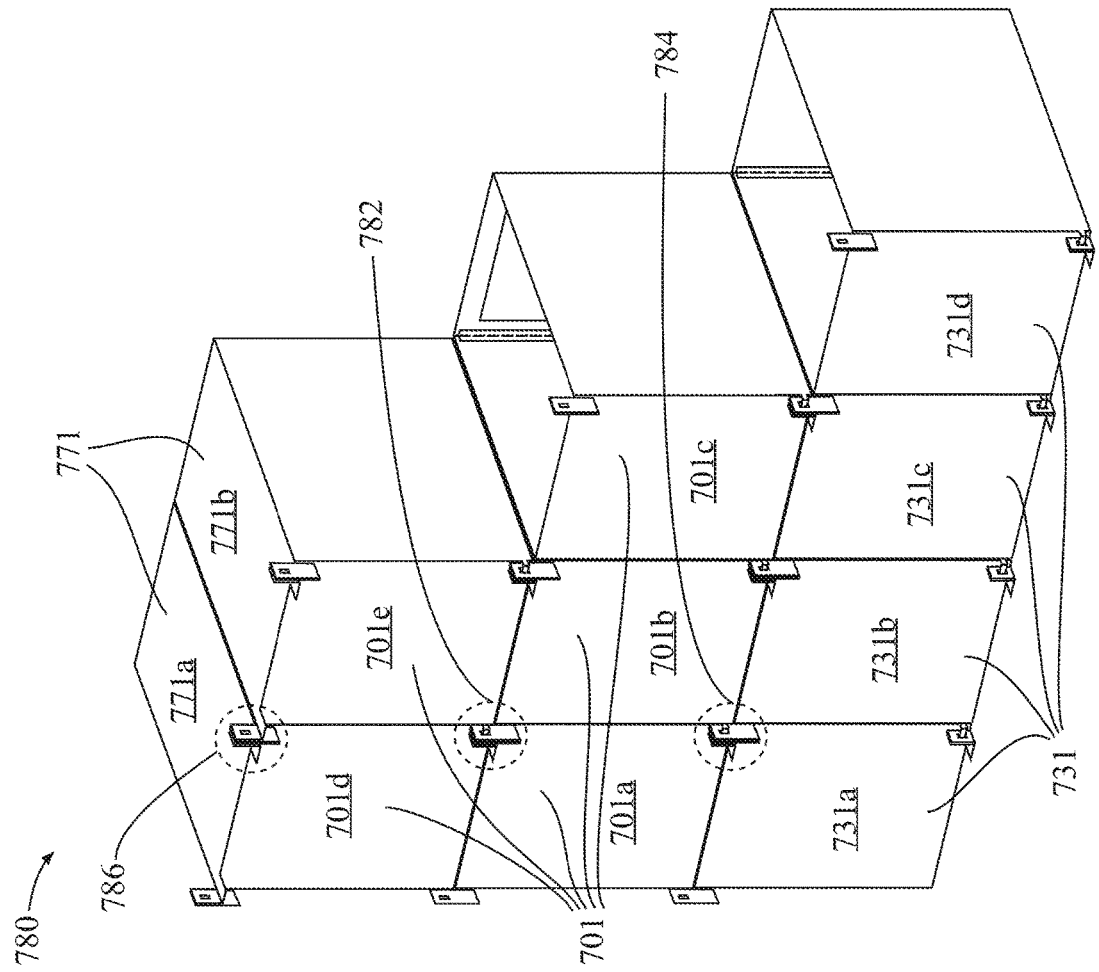
FIG. 7M is an example illustration depicting a partially assembled locker bank of collapsible and foldable lockers and bases.

Referring now to FIG. 7Q, FIG. 7Q illustrates a joining point 786 for joining two collapsible lockers 701d and 701e, and two top panels 771a and 771b wherein fastening tabs of lockers of adjacent columns may be joined together with fastening tabs of top panels using a shared fastener. Joining point 786 comprises left fastening tab 774a of top panel 771a, rear panel upper fastening tab 726d of locker 701d, left side panel upper fastening tab 714d of locker 701d, right side panel upper fastening tab 720e of locker 701e and right fastening tab 776b of top panel 771b.

Figure 7R:
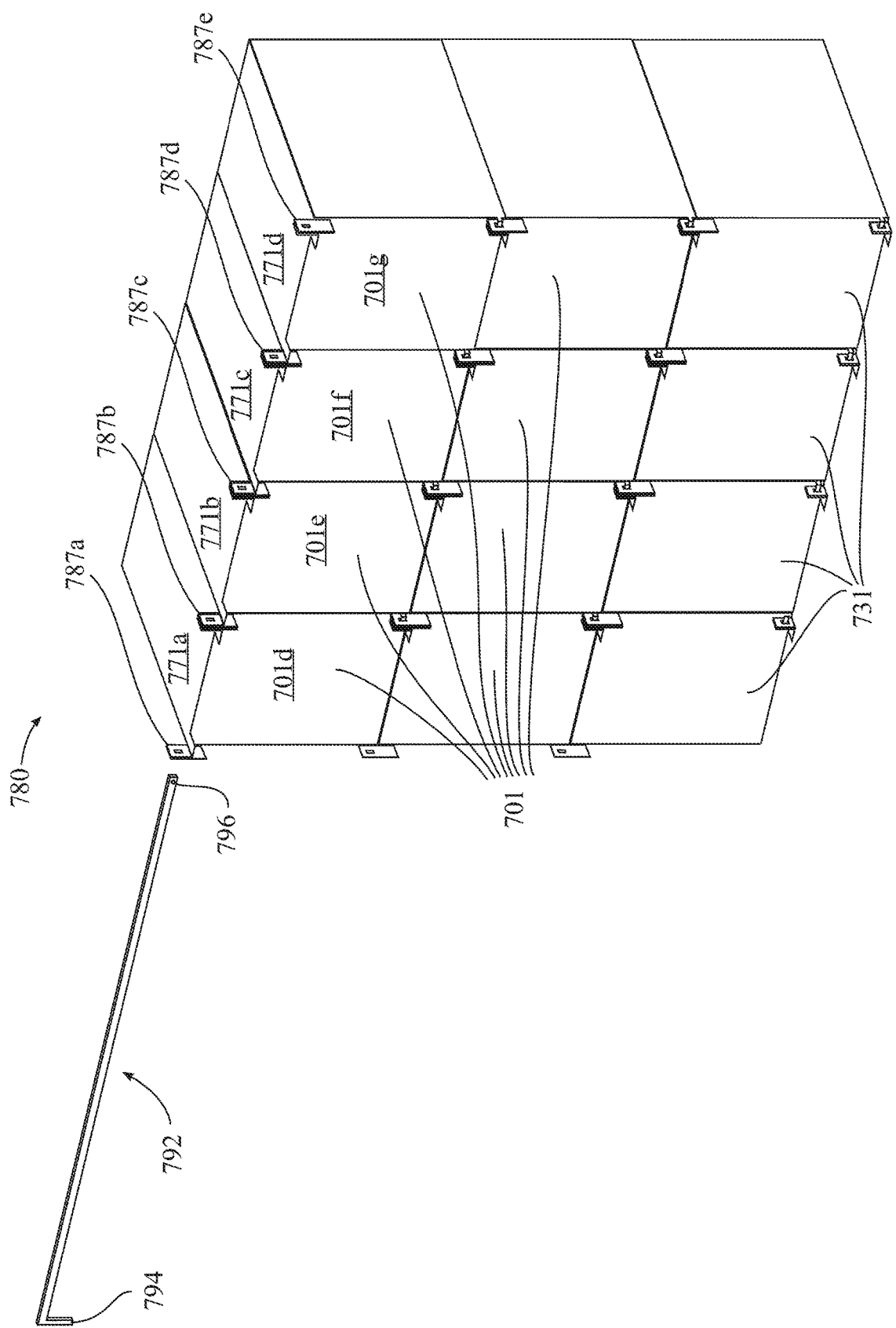
FIG. 7R is an example illustration depicting an assembled locker bank of collapsible and foldable lockers and bases comprising a locking bar.

FIG. 7R is an example illustration depicting locker bank 780 of FIG. 7M with the assembly of the column comprising base 731c and locker 701c completed, and the assembly of the column comprising base 731d completed. Top panels 771a, 771b, 771c and 771d may be secured to the top row of collapsible lockers 701d, 701e, 701f and 701g by passing a locking bar 792 through fastening tabs of joining points 787a, 787b (corresponds to joining point 786 of FIG. 7M and FIG. 7Q), 787c, 787d and 787e. Locking bar 792 may comprise an end 794 formed to prevent passage of bar 792 fully through joining point 787a, and hole 796 which may pass through joining point 787e. Once hole 796 has passed through joining point 787e a lock hasp may be passed through hole 796 and a lock secured thereto, such that locking bar 792 is locked in place and thereby securing locker bank 780. Locking bar 792 may additionally be passed through brackets (not shown) mounted to a supporting wall (not shown) in order to secure locker bank 780 to the supporting wall. This can improve the stability of locker bank 780 and prevent unauthorized removal of locker bank 780. This added stability and securing against unauthorized removal can be used and may be particularly useful in smaller locker bank configurations, vertical stack assemblies and single unit configurations where a lower weight and size thereof may be more prone to unauthorized removal.

The aforementioned collapsible locker system can be shipped in a relatively flat configuration when it is disassembled. This provides savings in shipping and delivery costs. The collapsible locker system may be easily and compactly transported to a location when needed, and easily set up and taken down to be once again transported as needed to address temporary and dramatically fluctuating demands associated with temporary secure storage. Furthermore, temporary secure storage arrangements using the aforementioned collapsible locker system can be flexibly configured to comprise individual lockers 700, vertical stack assemblies 760 and locker banks 780.

Chain of Custody with Intermediary Secure Storage Transfer Entities

In a chain of custody, each entity acting in the chain from origination to final receipt, including each intermediary, transfers control of the property under custody as appropriate with their position in the chain. Property transfers between chain origination and chain termination, where an intended recipient receives custody of property, may be authenticated, captured, certified and securely recorded in order to securely document and certify a chain of custody, wherein each participating entity is identified and authenticated, and each transfer transaction is accurately captured, certified and securely recorded.

Embodiments of secure locker systems may comprise a chain of custody service. A chain of custody service may be implemented to provide a varied scope of coverage. An embodiment may comprise a chain of custody service for transfers comprising secure temporary storage as a participating entity. When a secure lockable compartment as disclosed herein is used as an intermediary custody transfer entity, it can be uniquely identified and authenticated, and participate in a transfer that can be accurately captured and securely recorded. Furthermore, when a secure lockable compartment is used as an intermediary custody transfer entity, it may be particularly beneficial to accurately capture and securely record the transfer, since without recorded documentation of a transfer, disputes arising from a property loss may not be fully investigated. As such, an operator of a secure locker system may wish to offer a secure storage platform comprising a secure chain of custody service. In an embodiment, an operator of a secure locker system may wish to offer a secure storage platform comprising a secure chain of custody service for transfers where a secure lockable compartment is used as an intermediary custody transfer entity. In an embodiment, an operator of a secure locker system may wish to offer a secure storage platform comprising a secure chain of custody service for some or all transfers in a chain of custody from originating entity to end-recipient. In an embodiment, an originating entity or other entities in a chain of custody may specify a release authority, wherein a release authority is a specification which may specify requirements and actions necessary to authorize a custodian to release property of custody in a custody transfer transaction, and transfer release authority obligations to a receiving entity. As such, where secure storage is a participating entity in a custody transfer transaction, a release authority may specify obligations of a storage platform and lockable compartment thereof, when receiving custody, and requirements and actions for a storage platform to execute in releasing custody from a lockable compartment to a receiving entity. Release authority specifications may comprise, but are not limited to, mechanisms for authentication of a receiving entity, such as specifying a secure locker access application and account by which to authenticate a receiving party; mechanisms for providing an access token to a receiving entity, such as specifying an email address or phone number to which to send an access token; requiring one or more release mechanisms; and requiring multifactor authentication.

The secure locker system with secure storage platform disclosed herein provides secure lockable compartments that can be uniquely identified by a unique lock ID (and location ID and locker ID) and require a cryptographically secure single use access authentication code for access. As such, the provision of a single use access authentication code to an authenticated entity, and the use by that authenticated entity of that single use access authentication code to access a lockable compartment in order to execute a custody transfer of property can be accurately captured. Additional features of a secure chain of custody service will be disclosed later herein.

Figure 8A:
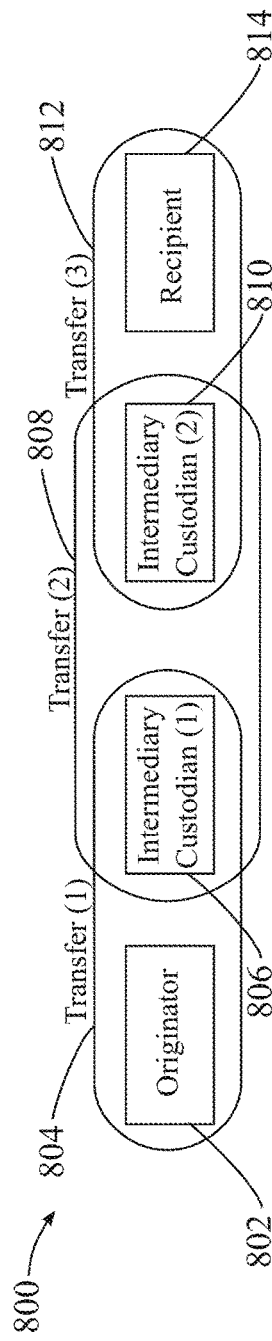
FIG. 8A is an example illustration depicting a chain of custody beginning with an originator, ending with a recipient and comprising two intermediary custodians.

FIG. 8A depicts an example illustration of a chain of custody 800 beginning with an originator 802, ending with a recipient 814 and comprising two intermediary custodians, namely, intermediary custodian (1) 806 and intermediary custodian (2) 810. Originator 802 and intermediary custodian (1) 806 are linked with a custody transfer (1) 804 wherein originator 802 transfers custody to intermediary custodian (1) 806 who thereupon receives custody. Intermediary custodian (1) 806 and intermediary custodian (2) 810 are linked with a custody transfer (2) 808 wherein intermediary custodian (1) 806 transfers custody to intermediary custodian (2) 810 who thereupon receives custody. Intermediary custodian (2) 810 and recipient 814 are linked with a custody transfer (3) 812 wherein intermediary custodian (2) 810 transfers custody to recipient 814 who thereupon receives custody. For explanatory purposes, in the example illustration of FIG. 8A, let the following scenario apply: originator 802 is an online seller of an item of computer equipment, namely, a computer disk drive; intermediary custodian (1) 806 is a package delivery courier engaged by originator 802 to deliver the computer disk drive to a purchaser thereof, namely, recipient 814; intermediary custodian (2) 810 is a lockable compartment situated near a residence of recipient 814 to which the courier is to deliver the disk drive; and recipient 814 is unavailable to receive the computer disk drive at the time the courier arrives to deliver it. In this scenario, a lockable compartment may be used as intermediary custodian (2) 810 to take custody of and secure the computer disk drive until the availability of recipient 814 to receive and take custody of the disk drive, thereby permitting the package delivery courier to satisfy a release authority and effect a delivery while preventing theft or loss of the disk drive until such time that recipient 814 is available to ultimately receive it. As such, in this scenario of example illustration chain of custody 800, a purchaser in an online transaction, purchases a disk drive from a seller who then engages a package delivery service to deliver the disk drive. Specifically, the seller (originator 802) transfers custody (transfer (1) 804) of the disk drive to the package delivery courier (intermediary custodian (1) 806); the package delivery courier (intermediary custodian (1) 806) transfers custody (transfer (2) 808) of the disk drive to the lockable compartment (intermediary custodian (2) 810); and the lockable compartment (intermediary custodian (2) 810) transfers custody (transfer (3) 812) to the purchaser (recipient 814).

Figure 8B:
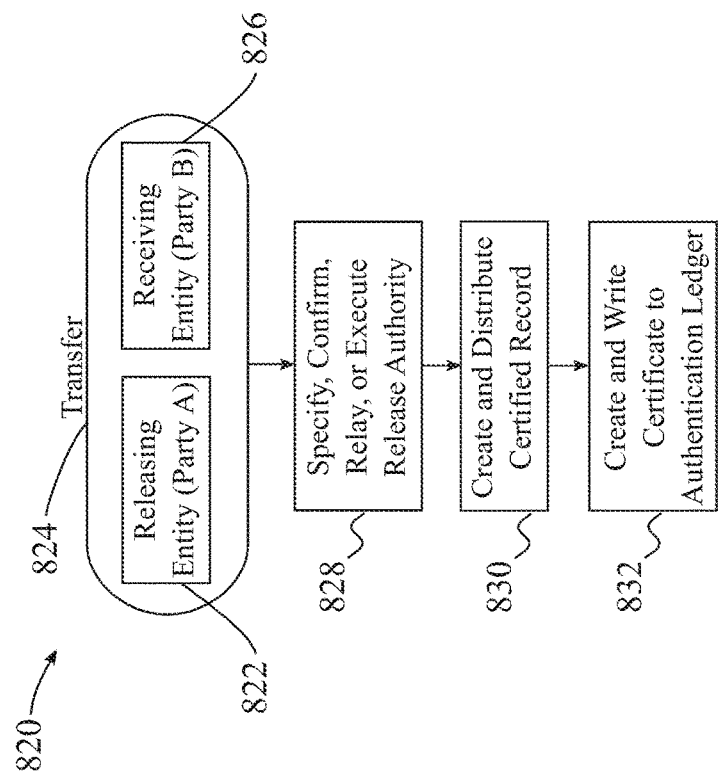
FIG. 8B is an example illustration depicting process for processing and recording a custody transfer and updating a custody authentication ledger.

FIG. 8B depicts an example illustration process 820 for processing and recording a custody transfer 824 and updating a custody authentication ledger. Process 820 is initiated by a custody transfer 824, wherein a releasing entity 822, associated with party A, transfers custody to a receiving entity 826, associated with party B, who thereupon receives custody of the property. In step 828, releasing entity 822 of transfer 824, may specify, confirm or relay a release authority, or may execute actions specified therein. A custody transfer record comprising a certificate, also referred to as a certified custody transfer record, certified transfer record or certified record, is created and distributed in step 830. The certified transfer record may be created and distributed by a secure locker system, such as secure locker system 100 of FIG. 1, further comprising a chain of custody service. In step 830, the certified transfer record can be distributed to interested parties, such as party A of transfer event 824, party B of transfer event 824, or a previous or planned entity such as an originator, if not party A, or planned recipient if not party B. In step 832, a ledger entry comprising an identifier of the certified transfer record, also referred to as a transfer ID, and the certificate thereof is created and written to a custody transfer authentication ledger. The custody transfer authentication ledger, also referred to as a custody authentication ledger or authentication ledger, may be maintained by a secure locker system, such as secure locker system 100 of FIG. 1, further comprising a chain of custody authentication service. A secure chain of custody authentication service can be queried by holders of certified transfer records to verify the authenticity and integrity thereof.

Figure 8C:
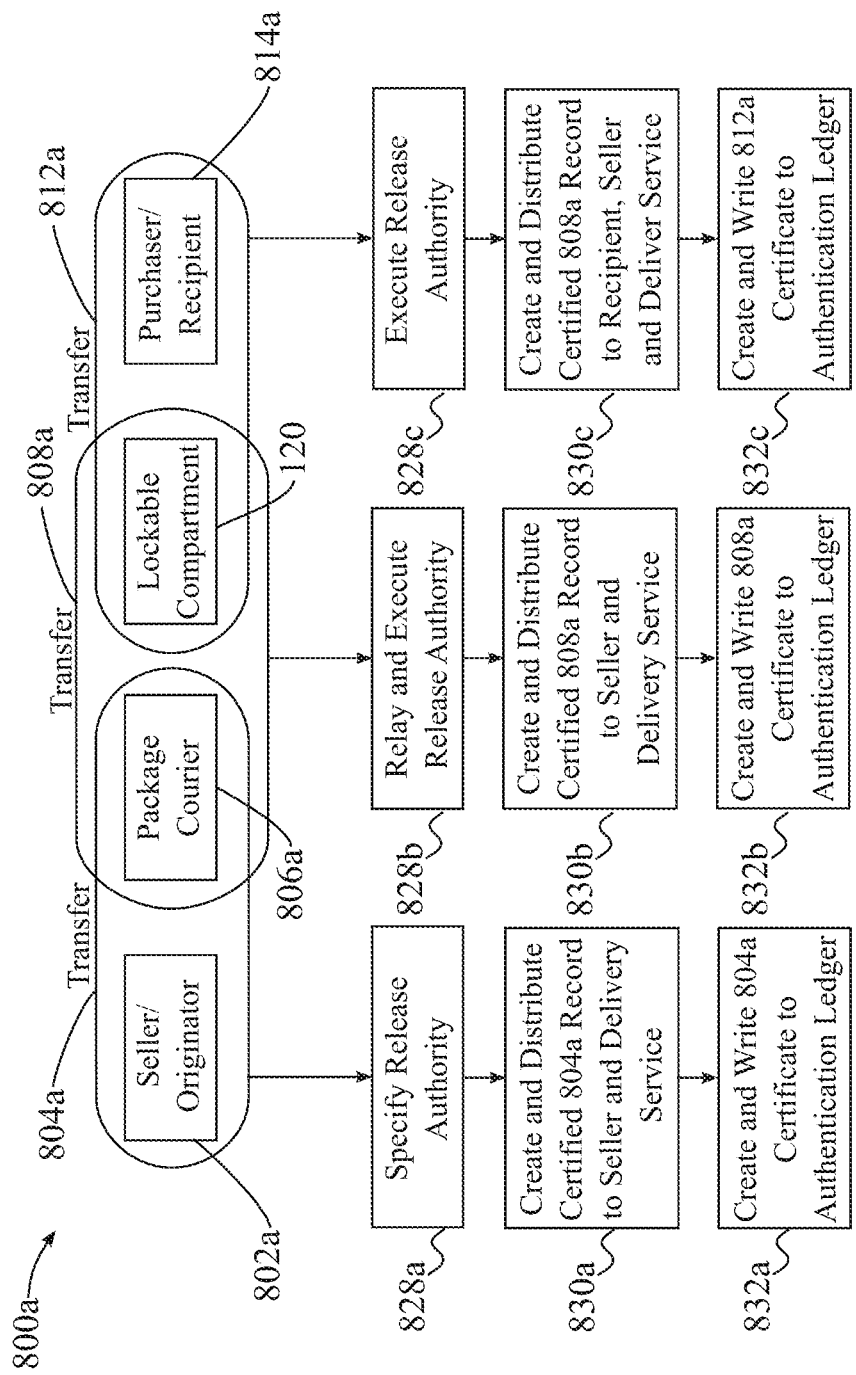
FIG. 8C is an example illustration depicting combining a chain of custody of FIG. 8A and a process for processing a custody transfer is of FIG. 8B illustrated for a package delivery scenario.
Figure 8D:
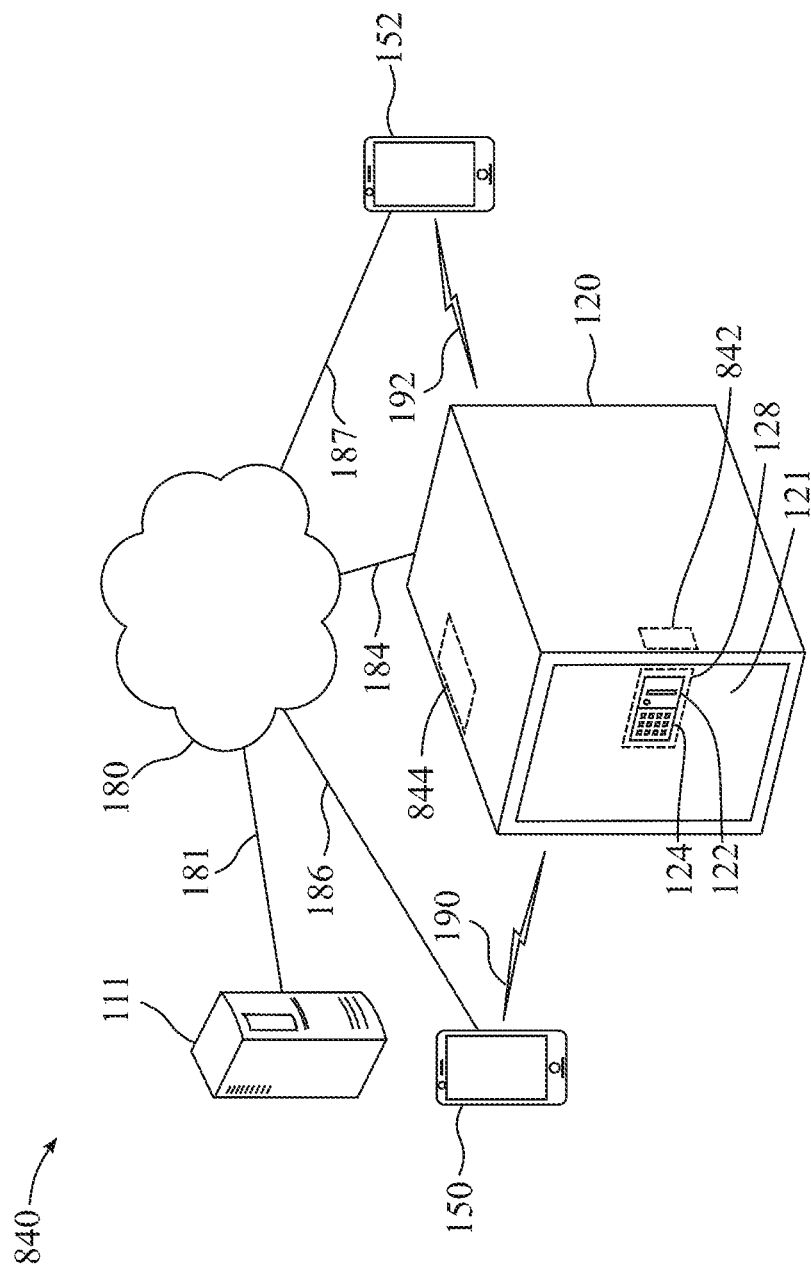
FIG. 8D is an example illustration depicting a system that can be used with a process of FIG. 8C.

An example illustration combining chain of custody 800 of FIG. 8A and process 820 of FIG. 8B for processing a custody transfer is illustrated for the delivery scenario of the online computer disk drive purchase discussed above, and is shown in an example illustration depicting a process 800a in FIG. 8C. Process 800a depicts a chain of custody process comprising a processing of three custody transfers 804a, 808a and 812a. Process 800a is discussed in conjunction with FIG. 8D which is an example illustration depicting a system 840 that can be used with process 800a of FIG. 8C. System 840 comprises a lockable compartment 120, portable wireless devices 150 and 152, server based system 111 and network 180. Portable wireless device 150 can be a device used by a package delivery courier 806a to assist in tracking and managing package deliveries, and portable wireless device 152 can be a smartphone of an intended recipient 814a of a package.

In transfer 804a, a seller 802a originates the chain of custody and transfers custody of a package comprising a computer disk drive to a package courier 806a. Transfer 804a comprises steps 828a, 830a and 832a. In step 828a, seller 802a specifies a release authority specifying a requirement for a signature of intended recipient 814a or use of a secure lockable compartment, such as lockable compartment 120. The release authority further specifies that the use of a lockable compartment and release therefrom requires an authentication of the recipient using an authenticated app and user account (e.g. specifies lockable compartment access through use of a secure locker system approved seller app and an account user name of recipient 814a to be used for release and receipt) or an access token which is to be sent to an email address of recipient 814a also specified in the release authority. In step 830a, a certified transfer record of transfer 804a is created and distributed to seller 802a and delivery service of courier 806a by a chain of custody service of server based system 111. In step 832a a ledger entry comprising a transfer ID and a certificate for certified transfer record of transfer 804a is created and written to a custody authentication ledger maintained by a chain of custody authentication service of server based system 111.

In transfer 808a, package courier 806a transfers custody of the package to lockable compartment 120, potentially after determining recipient 814a in not available to receive and sign for the package. In step 828b, details of the release authority are relayed and executed. In particular, courier 806a using portable wireless device 150 of FIG. 8D accesses lockable compartment 120 to transfer custody of the package thereto (and to securely store the package therein) and in the access process relays the release authority specification that the release to recipient 814a is required use of an authenticated app and a specified user account (i.e., relays the requirements specified in previous transfer 804a, that the lockable compartment access by recipient 814a requires use of a secure locker system approved seller app and further relays the account user name of recipient 814a to be used for authentication, release and receipt) or an access token which is to be sent to the email address of recipient 814a as specified therein. Access of lockable compartment 120 is made using portable wireless device 150 comprising functionality of an app approved by a system operator of lockable compartment 120 which uses an embodiment of open lockable compartment process 440 of FIG. 4B. Since process 440 is discussed in detail earlier herein, it will be discussed briefly and in part in conjunction with transfer 808a.

In conjunction with transfer 808a, an access request is made by courier 806a using portable wireless device 150 to open the lockable compartment 120 in step 444. In step 446 portable wireless device 150 checks to see if it is connected to a lock 122 via a short range communications link 190, such as a Bluetooth link. Once connected, in step 448, portable wireless device 150, sends an open lock request to server based system 111 via communications links 186 and 181 and network 180 and an initiate access command to lock 122. In step 450, lock access controller 128 of lock 120 starts an access timer and generates a verification code. In step 452, sever based system 111 generates a challenge code and sends it to portable wireless device 150. In step 454, portable wireless device 150 sends an open lock command and the challenge code to lock 122. In step 456, lock access controller 128 of lock 122 compares the challenge code to the verification code. In step 458, if the codes match and the access timer is still active, the process proceeds to step 464, wherein lock 122 opens and access to lockable compartment 120 is provided. In this embodiment of process 440 and step 464 thereof, upon successful access, portable wireless device 150 relays the release authority to server based system 111, wherein server based system 111 generates a random access token, and sends it to the email address of recipient 814a specified in the release authority, then encrypts the token using the derivation key for lock 122 and sends it in an open on token command to lock 122 via communications links 181 and 184 and network 180 or via portable wireless device 150. Lock access controller 128 of lock 122 decrypts the token and enables opening upon successful entry of the token into a keypad 124 comprised by or otherwise operably connected to lock 122 and lock access controller 128 thereof. Server based system 111 additionally executes the release authority specification for authenticated access by the user account of recipient 814a specified in the release authority, by assigning lockable compartment 120 thereto beginning upon conclusion of transfer 808a.

In step 464, lock 122 logs and reports the successful access transaction associated with transfer 808a to server based system 111 via portable wireless device 150. Lockable compartment 120 and lock access controller 128 therein may comprise a communications link 184 to the secure locker system 111 via network 180 and link 181, and thereby may alternatively or additionally report the access transaction associated with transfer 808a to server based system 111 in step 464. In an embodiment, lockable compartment 120 may comprise a door status sensor 842, such that an opening and closing of a lockable compartment door 121 can be observed by lock access controller 128. These additional access events associated with transfer 808a, and their time stamps can additionally be reported to server based system 111. In an embodiment, lockable compartment 120 may comprise a camera system 844 comprising an illumination source, such that the contents of lockable compartment 120 may be recorded prior to an opening of lock 122 and after a closing of door 121, and resulting images and their time stamps can additionally be reported to server based system 111. The closing of door 121 in relation to these images may be detected by the aforementioned door sensor 842 if present or alternatively observed by camera 844. This additional information can be reported to secure locker system 111 as an access event(s) associated with transfer 808a to record a change of contents of lockable compartment 120 associated with transfer 808a, and as such, a placement of the package in lockable compartment 120 can be accurately recorded. Courier 806a can be instructed to orient the package in lockable compartment 120 such that a package label commonly used in package delivery services comprised thereon and comprising a readable code indicating a package tracking number, is visible to camera system 844 and will accordingly also be visible in an image captured after door 121 is closed. In an embodiment, camera system 844 or lock access controller 128 can comprise software to determine if a readable code is in fact readable given a current orientation of the package, and the system can prompt the courier via portable wireless device 150 to adjust the position if needed to enable the code to be readable. In an embodiment, visual assistance showing the current view of camera system 844 can be displayed on portable wireless device 150 to assist courier 806a in a satisfactory placement of the package. In step 830b, a certified transfer record for transfer 808a is created and distributed to seller 802a and delivery service of courier 806a by secure chain of custody service of server based system 111. In step 832b a ledger entry comprising a transfer ID and a certificate for certified transfer record of transfer 808a is created and written to a custody authentication ledger maintained by a chain of custody authentication service of server based system 111.

In transfer 812a, lockable compartment 120 transfers custody of the package to recipient 814a when recipient 814a retrieves the package therefrom. In step 828c of transfer 812a, the recipient 814a can enter into keypad 124 a release token sent by email from server based system 111 in step 828b to access lockable compartment 120, or alternatively, use an authenticated app, meeting the requirements of the release authority as specified by seller in 828a and relayed by courier 806a to server based system 111 in step 828b, to access lockable compartment 120. In the case of the access token, recipient 814a enters the release token into keypad 124, and access controller 128 of lock 122 opens lock 122 if the entered token matches the token decrypted thereby. In the case of an authenticated app, recipient 814a uses portable wireless device 152 on which the specified authenticated app is running and is presently logged into the specified user account, to open lockable compartment 120 using an embodiment of process 440 of FIG. 4B. Since process 440 is discussed in detail earlier herein, it will be discussed briefly and in part in conjunction with transfer 812a.

In conjunction with transfer 812a, an access request is made by recipient 814a using portable wireless device 152 to open the lockable compartment 120 in step 444. In step 446 portable wireless device 152 checks to see if it is connected to lock 122 via short range link 192. Once connected, in step 448, portable wireless device 152, sends an open lock request to server based system 111 via communications links 187 and 181 and network 180 and an initiate access command to lock 122. In step 450, lock access controller 128 of lock 120 starts an access timer and generates a verification code. In step 452, sever based system 111 generates a challenge code and sends it to portable wireless device 152. In step 454, portable wireless device 152 sends an open lock command and the challenge code to lock 122. In step 456, lock access controller 128 of lock 122 compares the challenge code to the verification code. In step 458, if the codes match and the access timer is still active, the process proceeds to step 464, wherein lock 122 opens and access to lockable compartment 120 is provided. In an embodiment, both an access token and an authenticated app may be required for access when specified as such in a release authority. Where both are required, server based system may indicate such requirement with the sending of the encrypted access token in steps 828b and step 464 of process 440 in the embodiment thereof discussed in conjunction with step 828b. In this manner, lock access controller of 128 of lock 122 will require both the matching access token entry through keypad 124 and the access request from the authenticated app on portable wireless device 152 as specified in the release authority. As such, a two part authentication can be required and enforced directly by lock access controller 128 of lock 122.

In step 464, lock 122 logs and reports the successful access transaction associated with transfer 812a to secure locker system 111 via portable wireless device 152. Lockable compartment 120 and lock access controller 128 therein may comprise a communications link 184 to server based system 111 via network 180 and link 181, and thereby may alternatively or additionally report the access transaction associated with transfer 812a to server based system 111 in step 464. In an embodiment, lockable compartment 120 may comprise door status sensor 842, such that the opening and closing of lockable compartment door 121 can be observed by lock access controller 128. These additional access events associated with transfer 812a, and their time stamps can additionally be reported to server based system 111. In an embodiment, lockable compartment 120 may comprise camera system 844 comprising an illumination source, such that the contents of lockable compartment 120 may be recorded prior to the opening of lock 122 and after the closing of door 121, and images and their time stamps can be additionally reported to server based system 111. The closing of door 121 in relation to these images may be detected by the aforementioned door sensor 842 if present or alternatively observed by camera 844. This additional information can be reported to secure locker system 111 as an access event(s) associated with transfer 812a to record a change of contents of lockable compartment 120 associated with transfer 812a, and as such, a removal of the package in lockable compartment 120 can be accurately recorded. In step 830c, a certified transfer record for transfer 812a is created and distributed to seller 802a, delivery service of courier 806a and recipient 814a by secure chain of custody service of server based system 111. In step 832c a ledger entry comprising a transfer ID and a certificate for certified transfer record of transfer 812a is created and written to a custody authentication ledger maintained by a chain of custody authentication service of server based system 111.

Figures 9C, 9D:
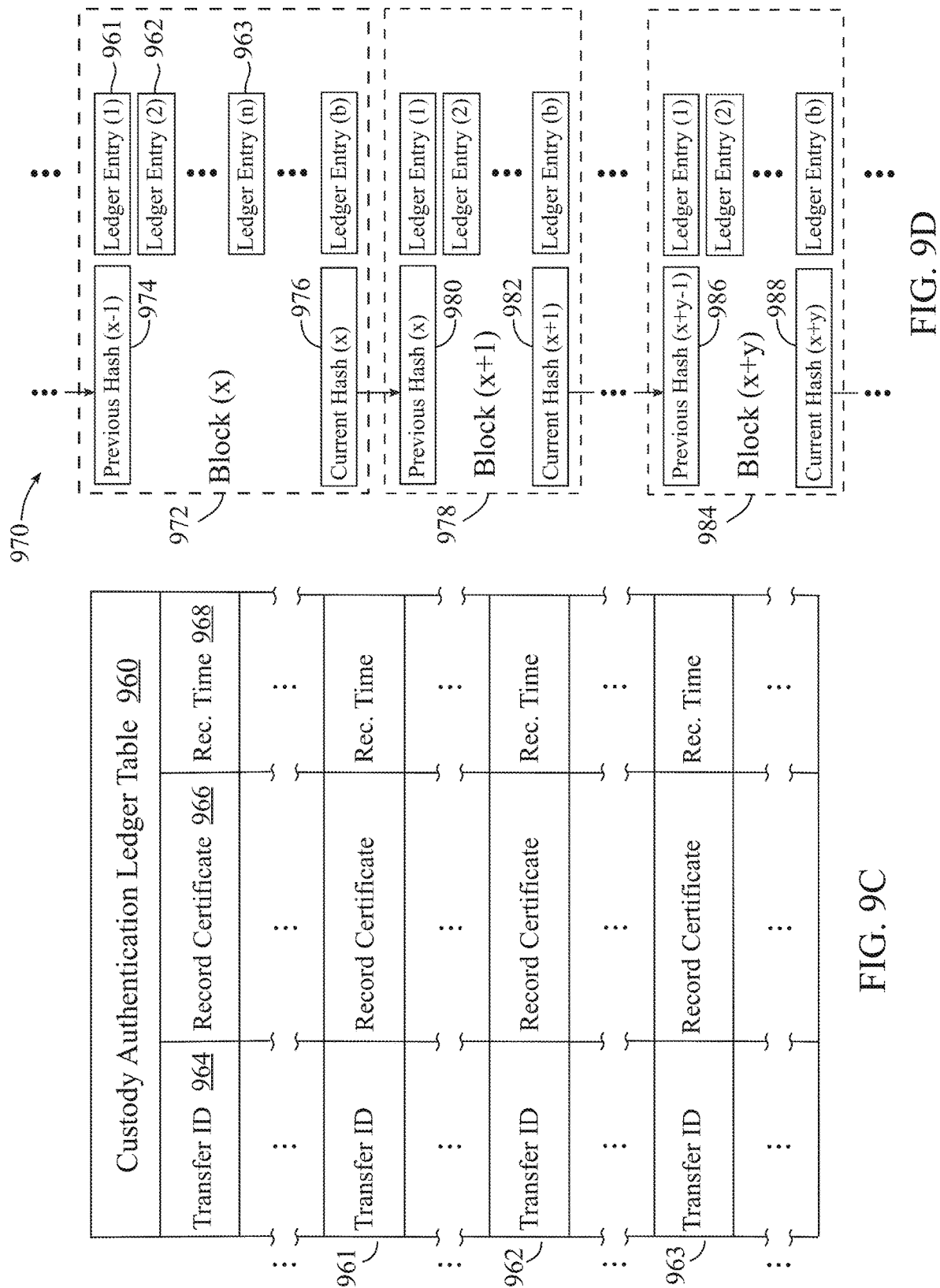
FIG. 9C is an example illustration depicting a custody authentication ledger table.
FIG. 9D is an example illustration depicting a portion of a blockchain custody authentication ledger.

In the example chain of custody process 800a of FIG. 8C, certified records for three transfers 804a, 808a and 812a are created and distributed in steps 830a, 830b and 830c, respectively. In steps 832a, 832b and 832c, ledger entries are created and written to a custody authentication ledger. Recipients and holders of certified transfer records received in steps 830a, 830b and 830c can query an authentication ledger at a current or future time to validate the authenticity and integrity of a certified record. Server based system 111 comprising a chain of custody service and chain of custody authentication service may comprise a custody event table 900, custody transfer table 930 and a custody authentication table 960 of which example illustrations are depicted in FIG. 9A, FIG. 9B and FIG. 9C, respectively, and which may be used to record transfers and events thereof, comprise certified transfer records and comprise authentication ledger entries.

Custody event table 900 comprises event records related to custody transfers, and the data comprised by custody event records may be used to create certified custody transfer records. Examples of events related to custody transfers comprise, but are not limited to: specification of, relay of or an action report related to a release authority; access events of a lockable compartment by a releasing entity or receiving entity; door opening and door closing events of a lockable compartment during a transfer process therewith and images captured of a lockable compartment and contents thereof prior to and after an access event by a releasing or receiving entity. Custody event table 900 comprises an event ID column 904, an event type column 906, a transfer ID column 908, an event time column 910, a release ID column 912, a receive ID column 914, a property ID column 916, a release data column 918 and a receive data column 920. Custody event table 900 is depicted comprising exemplary custody event records 901, 902 and 903.

Event ID column 904 comprises a unique identifier which is assigned to an event and may be used to refer to a specific custody event. Event type column 906 comprises classifications for events such as, but not limited to, an access attempt by a releasing entity, and access attempt by a receiving entity, a successful access attempt, a failed access attempt, a door opening, a door closing, an image capture comprising a package tracking bar code, a release authority specification, an access token generated and emailed per a release authority specification, a recipient authentication per a release authority specification, and the like. Transfer ID column 908 comprises identifiers assigned by chain of custody service of server based system 111 to uniquely identify a custody transfer. Both a releasing entity and a receiving entity of a custody transfer may submit custody events related to a transfer, and each may submit more than one event related to a transfer. As such, an assignment of a given transfer ID may be applied to one or more events related to a given transfer. Transfer ID assignment will be discussed in more detail later herein. Event time column 910 comprises a date and time stamp for an event and may be specified by the entity reporting the event.

Release ID column 912 comprises a participant ID identifying the releasing entity in the custody event. All intermediary custodians in a chain of custody service comprise unique participant IDs. For example, a delivery courier participating in the custody transfer service, has a unique participant ID within the secure locker system, such that they can be authenticated for participation in a custody transfer by their ID, and a secure lockable compartment can be uniquely identified by a unique location ID and locker ID combination. Furthermore, each participant, such as each participating lockable compartment or participating courier, can be specifically referenced by this ID in a custody event or transfer record. Release ID column 912 may comprise IDs associated with originators or intermediary custodians releasing a property of the current custody event. An originator and a recipient may have an account comprising a unique participant ID within the system, or may be sponsored for participation in the service by a participant. For example, a package delivery courier may sponsor an originator or an end-recipient as part of a chain of custody in which the package delivery courier is a participant. Or, an originator may sponsor an end-recipient. For example, an online retailer may sponsor an end-recipient. In cases of sponsorship, a unique ID may be assigned within server based system 111 at the time of sponsorship, such as when a release authority is transmitted to a server based system 111 which identifies a sponsored participant. Assignment of a unique ID may be made based on data specified in a release authority used to identify or notify a participant, such as an email address and/or mobile phone number to which to send an access token needed to access a lockable compartment serving as an intermediary custodian. As such, a participant ID assigned to a given sponsored participant may be reapplied to the same sponsored participant similarly specified in other release authorities specified in other custody transfers. Receive ID column 914, comprises a participant ID for a receiving entity of a custody event.

Property ID column 916 comprises IDs which may be assigned by an originator or an intermediary custodian and specified in a release authority which is sent to server based system 111. A property ID refers to the property of custody in a custody event. In the case of a custody event associated with package delivery, a property ID may be a package tracking number which are actively used by package delivery services. Major package delivery couriers may recycle use of package tracking numbers, and as such, property IDs may not be unique. However, a recycling may not occur for many months and within the time span of a chain of custody of a delivered package, a package tracking number is unique. A property ID may be generated and assigned by server based system 111 if none is specified.

Release data column 918 and receive data 920 comprise data that a releasing participant and a receiving send to server based system 111 for inclusion in a custody event record and custody transfer record. For example, a releasing participant which is a package delivery courier may wish to note that an unsuccessful attempt to reach an end-recipient was made at a specific time, and alternatively custody transfer to a lockable compartment per a release authority will be attempted. Or data may comprise information, such as but not limited to, weather conditions, images related to a package placed in a lockable compartment which may have been taken with a portable wireless device used to access the compartment or a camera system comprised by the compartment, images of a package retrieved from a compartment. Data in columns 918 and 920 are initially part of event records in table 900 and may be processed and included in custody transfer records within table 930 of FIG. 9B which may be certified and distributed to participants in a chain of custody. Accordingly, information useful to document a transfer, such as the property transferred, the condition of the property transferred, circumstances surrounding the transfer that are desired to be made of record and shared with the participants of the chain of custody may be communicated to server based system 111 for inclusion in columns 918 and 920.

Custody transfer table 930 of FIG. 9B comprises custody transfer records created from custody event records from table 900 and share some similar columns therewith. Custody transfer table 930 comprises a transfer ID column 934, transfer type column 936, chain ID column 938, transfer time column 940, release ID column 942, receive ID column 944, property ID column 946, releasing event data column 948, receiving event data column 950 and record certificate 952. Custody transfer table 930 is depicted comprising exemplary custody transfer records 931, 932 and 933.

A transfer ID within transfer ID column 934 is first assigned by custody transfer service of server based system 111 to one or more custody event records in table 900, and is an identifier for a custody transfer and, as such, is generally associated with only one record in custody transfer table 930. Given a unique result from a combination of a releasing ID, a receiving ID and a property ID, in a first recorded custody event submission in table 900, a new transfer is generally indicated and a new transfer ID can be assigned thereto. Subsequent custody events comprising the same combination of releasing ID, receiving ID and property ID can be assigned to the same transfer and therefore be assigned the same transfer ID. It is highly unlikely but remotely possible that a property ID is recycled or two identical property ID can be coincidentally submitted by different parties, and the same releasing entity (and releasing ID), and same receiving entity (and receiving ID) are engaged in a second custody transfer involving the same property ID. However, given a reasonable time window over which to consider custody events for inclusion in a transfer and assignment of a particular transfer ID, eliminates a possible erroneous assignment. An operator of a custody transfer service may choose a maximum time for which to leave open multiple assignments of a transfer ID to custody event submissions, such as a maximum custody transfer time (e.g. 5 minutes), or a short delay (e.g. 5 seconds) following a probable final custody event of a custody transfer is received, such as an event submission indicating the transfer has completed. Or both methods may be employed, wherein the first to occur is used as a closing time for event submissions. Regardless of how a closing time for event submissions related to a transfer ID is chosen, an earliest possible time is preferred in order for a timely creation and distribution of a custody transfer record documenting the transfer.

Transfer type column 936 comprises a classification of custody transfers, such as but not limited to, originating transfer, intermediary transfer, end-recipient transfer, transfer to secure lockable compartment, transfer from secure lockable compartment. Chain ID column 938 comprises identifiers assigned by chain of custody service of server based system 111 to uniquely identify a chain of custody. The same chain ID is assigned to each transfer record comprised by a chain of custody. A chain ID is established by an occurrence of a releasing ID and property ID having no corresponding prior receiving ID with the property ID for the same participant ID. When the receiving ID is equal to a subsequent releasing ID for the same property ID, the releasing ID and property ID of the current transfer are part of an existing chain of custody. An originating transfer can be defined, at least in part as an occurrence of a releasing ID and property ID having no corresponding prior receiving ID with the property ID for the same participant ID. A broken chain of custody, where a transfer is unreported, or a non-reported originating transfer results in a newly assigned chain ID assignment to an intermediary transfer rather than an originating transfer.

Release ID column 942, receive ID column 944 and property ID column 946 indicate participants and property in the same manner as in custody event table 900. Release event data column 948 and receive event data column 950 for a given transfer record comprise event data from one or more respective release column 918 or receive data column 920 of one or more custody event records comprising the transfer ID of the given transfer record, and may further comprise event type 906 and event time 910 column data. In this manner, a custody transfer record may comprise a complete account of submitted data for a custody.

As discussed in conjunction with steps 830 of FIG. 8B and 830a, 830b and 830c of FIG. 8C, a certified custody transfer record can be created by a secure chain of custody service of server based system 111. These records can reside in custody transfer table 930 as described in the foregoing discussion. However, until the generation and addition of a record certificate in column 952, they are custody transfer records and not certified custody transfer records. Record certificate 952 can be cryptographic hash of record fields of columns 934, 936, 938, 940, 942, 944, 946, 948 and 950, such as an SHA-3 compliant hash, as published by the National Institute of Standards and Technology (NIST) in Federal Information Processing Standards Publication 202 (FIPS PUB 202), SHA-3 Standard: Permutation-Based Hash and Extendable-Output Functions, August 2015. A cryptographic hash of record fields of columns 934, 936, 938, 940, 942, 944, 946, 948 and 950 of a record, creates a digital fingerprint thereof for use as a certificate for inclusion in record field record certification column 954. Any alteration of record fields of columns 934, 936, 938, 940, 942, 944, 946, 948 and 950 results in an unpredictable change in the certificate, and the potential to modify a record and preserve a certificate value is highly improbable. As such, a record may be authenticated using a certificate known to be valid for a subsequent calculation of a hash of the fields, wherein should a matching hash result from the fields, the record is determined to be authentic and the integrity of the information therein is verified.

As discussed in conjunction with step 832 of FIG. 8B and steps 832*a*, 832*b* and 832*c* of FIG. 8C, ledger entries comprising transfer IDs and certificates for certified transfer records created and distributed in step 830 of FIG. 8B and steps 830*a*, 830*b* and 830*c* of FIG. 8C, are created and written to a custody authentication ledger maintained by a chain of custody authentication service of server based system 111. Custody authentication ledger table 960 of FIG. 9C can be maintained such that it does not comprise sensitive information and information therein can be made available with few or no restrictions. Authentication ledger 960 comprises a transfer ID column 964, a record certificate column 966 and a time of recording column 968. Transfer ID column 964 and record certificate column 966 correspond to transfer ID column 934 and record certificate column 952 of custody transfer table 930. Time of recording column 968 comprises the date and time a ledger entry was created and written to ledger 960. Custody authentication ledger table 960 is depicted comprising exemplary custody authentication ledger records, also called ledger entries, 961, 962 and 963.

In an embodiment, an authentication ledger can be a blockchain ledger and may be maintained by multiple entities, such as entities having regular participation in chain of custody transfers, for example, package delivery services, leading online retailers and a secure locker system operator. Multiple participating entities can operate blockchain nodes to enforce a consensus agreement required therefrom as a requirement for adding a block of ledger entries to the blockchain. A blockchain so maintained can be immutable and certifications thereon in the form of ledger entries can be relied on for validating certified chain of custody records accordingly. Furthermore, a blockchain so maintained retains a consensus capability and comprises redundancy and continued availability when greater than 50% of the nodes are operable and available.

FIG. 9D is an example illustration depicting a portion of a blockchain custody authentication ledger 970 comprising block (x) 972, block (x+1) 978 through block (x+y) 984, where x and y are positive integers and y is greater than 2. Blockchain 970 is secured using a cryptographic hash function such as an SHA-3 compliant hash, as published by the National Institute of Standards and Technology (NIST) in Federal Information Processing Standards Publication 202 (FIPS PUB 202), SHA-3 Standard: Permutation-Based Hash and Extendable-Output Functions, August 2015. The contents of each block are secured with a cryptographic hash and each block is linked to its previous block by the inclusion of the hash of the previous block. This arrangement can be seen in FIG. 9D, wherein each block comprises a hash of the previous block and a current hash in addition to ledger entries. Block (x) 972 comprises previous hash (x−1) 974 and current hash (x) 976; block (x+1) 978 comprises previous hash (x) 980 and current hash (x+1) 982, wherein previous hash (x) 980 of block (x+1) 978 is equal to current hash (x) 976 comprised by block (x) 972; and block (x+y) 984 comprises previous hash (x+y−1) 986 and current hash (x+y) 988. Each block of blockchain 970 comprises b ledger entries, or stated another way, b is the size of the blocks as measured by the number of ledger entries. Three ledger entries in block (x) 972 are referenced. They are ledger entry (1) 961, ledger entry (2) 962 and ledger entry (n) 963. The chain of linked cryptographic hashes means any change in the contents of any ledger entry in any block will alter the current hash calculated for the altered block and the current hashes calculated for all blocks following the altered block. For example, a change to ledger entry (2) 962 of block (x) 972 will alter the calculated current hash (x) 976, which will alter previous hash (x) 980 of block (x+1) 978 (since it is set equal to current hash (x) 976 of block (x) 972), which will change the calculated current hash (x+1) 982 for block (x+1) 978, which then similarly propagates changes through the subsequent blocks. Thus any alteration of a blockchain authentication ledger, even a single bit in a ledger entry, for a participating blockchain node will cause the node comprising the alteration to incorrectly calculate a current hash calculation for a new block to be added to the blockchain. The node comprising the alteration will fail to meet a consensus determination of a correct current hash and can be flagged as comprising invalid ledger entries and decommissioned until the issue inconsistency is resolved. As such, the blockchain authentication ledgers are immutable and the ledgers of the remaining nodes can be relied on with confidence in the authentication of certified custody records.

Figure 8E:
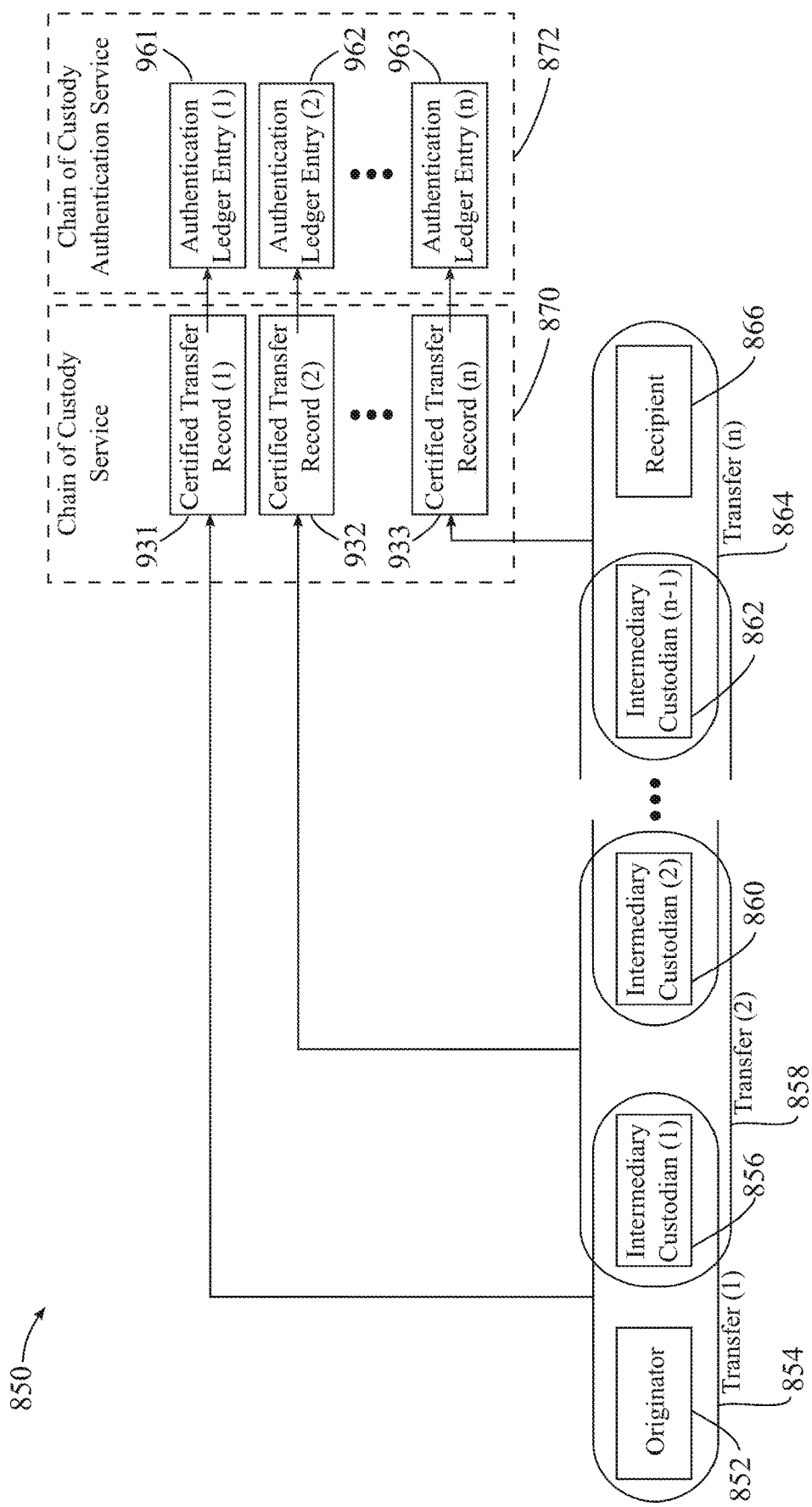
FIG. 8E is an example illustration of a process for maintaining chain of custody records and an authentication ledger.

FIG. 8E is an example illustration of a process 850 for maintaining chain of custody records and an authentication ledger which can be provided as services to document, report and authenticate chain of custody transactions, such as transfers 804*a*, 808*a* and 812*a* as discussed in reference to FIG. 8C. A server based system, such as server based system 111 of secure locker system 100 of FIG. 1A and server based system 111 of FIG. 8D, may further comprise a chain of custody service 870 and a chain of custody authentication service 872. Process 850 depicts a chain of custody having n transfers, namely, transfer (1) 854, transfer (2) 858 through transfer (n) 864. Transfer (1) 854 comprises a transfer from an originator 852 to an intermediary custodian (1) 856. Transfer (2) 858 comprises a transfer from intermediary custodian (1) 856 to an intermediary custodian (2) 860. Transfer (n) 864 comprises a transfer from an intermediary custodian (n−1) 862 to a recipient 866. As such, when n=3, intermediary custodian 860 and intermediary custodian 862 are the same custodian and the chain of custody of process 850 resembles chain of custody 800 illustrated in FIG. 8A which comprises transfer (1) 804, transfer (2) 808 and transfer (3) 812. In the example illustration of FIG. 8E, custody transfers 854, 858 through 864, result in the creation of n certified custody transfer records, namely, certified transfer record (1) 931, certified transfer record (2) 931 through certified transfer record (n) 932, which can also be seen in the example illustration of custody transfer table 930 of FIG. 9B. Certified transfer records 931, 932 through 933 are certified and therefore comprise certificates in column 952. n custody authentication ledger entries are created, namely, authentication ledger entry (1) 961, authentication ledger entry (2) 962 through authentication ledger entry (n) 963, comprising these record certificates, which can also be seen in the example illustrations of custody authentication ledger table 960 of FIG. 9C and blockchain custody authentication ledger 970 of FIG. 9D each comprising authentication ledger entry (1) 961, authentication ledger entry (2) 962 through authentication ledger entry (n) 963.

Post-Delivery Redirected Delivery, En Route Delivery and Other Flexible Delivery and Dispatch Services In various embodiments, a secure locker system comprising chain of custody services can provide various secure delivery and dispatch services comprising post-delivery redirected delivery, en route and impromptu delivery and dispatch services and other flexible delivery and dispatch services. For example, an intended recipient may be notified that a package has been delivered to a lockable compartment at their condominium residence while they are away from home. Yet they would benefit from receiving the package prior to their planned return home. In an embodiment, they can authorize and schedule a transfer of custody to a delivery service and have the package securely collected from the lockable compartment and delivered to their present location, planned future location or securely delivered to a lockable compartment in a convenient proximity thereto. In an embodiment, an intended recipient may be traveling and may have a package delivery synchronized with their travel itinerary such that delivery is made to a secure lockable compartment conveniently accessible while traveling. In an embodiment, a person may dispatch a package for delivery while traveling by accessing a lockable compartment, transferring custody of the package thereto and scheduling a transfer of custody to a delivery service. In an embodiment, a person may have temporarily secured property in a lockable compartment, such as in a lockable compartment at a sporting event or at a concert venue, and later have their items delivered to them rather than return to the lockable compartment themselves. In such a situation, they schedule an impromptu transfer of custody to a delivery service to have their items delivered to a present location, planned future location or securely delivered to a lockable compartment in a convenient proximity thereto.

Figures 10A, 10B:
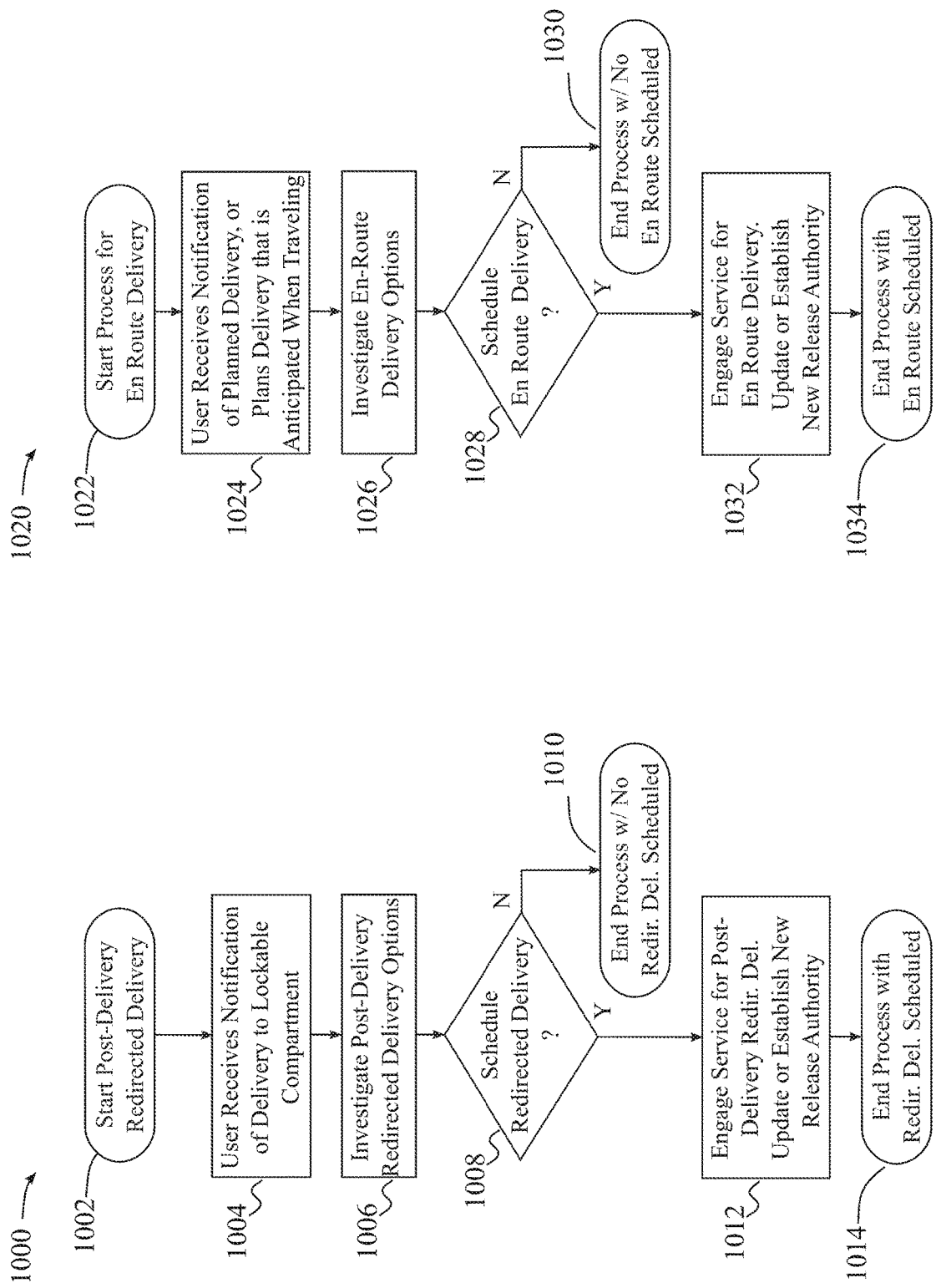
FIG. 10A is an example illustration depicting a post-delivery redirected delivery process.
FIG. 10B is an example illustration depicting an en route delivery process.

An example illustration of a post-delivery redirected delivery process 1000 is depicted in FIG. 10A. Post-delivery redirected delivery process 1000 begins in step 1002, and in step 1004 a user receives a notification of a delivery for which they are the intended end-recipient and which has been made to a lockable compartment. A user may decide they want to investigate having a delivery service deliver the package to a more convenient location given their present circumstances. For example, the user may be expecting a late return home, and would benefit from a same-day redirected delivery to their current location. Or the user may be traveling and would benefit from a next-day redirected delivery to a planned location the following day. When a redirected delivery is of interest, a user can investigate post-delivery redirected delivery options in step 1006. If, in step 1008, a user chooses not to schedule a redirected delivery the process ends in step 1010. If a user chooses to schedule a redirected delivery, the process proceeds to step 1012. In step 1012, the user engages a service for post-delivery redirected delivery and updates or otherwise establishes a release authority with the secure storage platform which specifies the engaged service as a receiving entity for the transfer of custody from the secure lockable compartment comprising the package, and further specifies the user as the end-recipient. Thus in the case of an updated release authority, the chain of custody is extended, or in the case of a newly established chain of custody, a new chain is created where an originating transfer may be recorded with the user specified as an originator that is transferring custody to a receiving secure lockable compartment. In the case of a courier differing from the courier making the initial delivery, the latter option of establishing a new chain may be preferred. In the case of the original courier being re-engaged for the post-delivery redirect, the former option of extending the chain of custody may be preferred. Regardless of which method is chosen, the release authority now permits the engaged service to complete the post-delivery redirected delivery and the process ends in step 1014.

An example illustration of an en route delivery process 1020 is depicted in FIG. 10B. En route delivery process 1020 begins in step 1022. In step 1024, a user receives a notification of a planned delivery, or plans a delivery that is anticipated or is desired to be delivered when the user is traveling. In step 1026 the user investigates options to have the package delivered while they are traveling. In an embodiment, functionality may be provided to synchronize delivery services with a user's travel itinerary in order to present available options, which may be sorted by cost, proximity and the like. If, in step 1028, a user decides not to schedule an en route delivery, the process ends in step 1030. If the user decides to schedule an en route delivery, the process proceeds to step 1032. In step 1032, the user engages a service for en route delivery. If the package has yet to ship from an originator, a new release authority is created which specifies the engaged service as a receiving entity for a transfer of custody from the originator, the user as the end-recipient of an en route delivery, and an en route delivery location. If the package has already shipped, a current release authority is updated to permit the current courier to change the delivery location to an en route location with the user as the end-recipient. Regardless of which case is used, namely, a new or updated release authority, the release authority permits the engaged service to make an en route delivery and the process ends in step 1034.

Figure 10C:
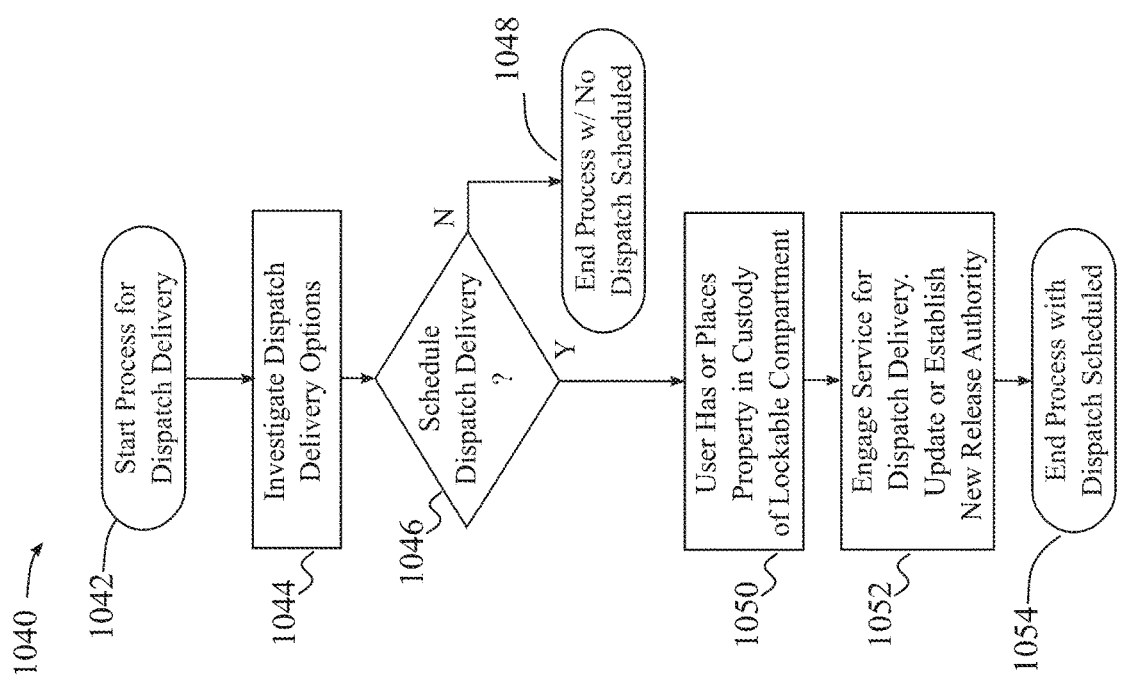
FIG. 10C is an example illustration depicting an impromptu and planned dispatched delivery process.

An example illustration of an impromptu and planned dispatched delivery process 1040 is depicted in FIG. 10C. Impromptu and planned dispatched delivery process 1040 begins in step 1042. In step 1044, a user having placed property in a lockable compartment then later considers having it delivered (impromptu), or a user with property that they may want to have delivered (dispatched) investigates dispatch delivery options. If, in step 1046, a user decides not to schedule a dispatch delivery, the process ends in step 1048. If the user decides to schedule a dispatch delivery, the process proceeds to step 1050. In step 1050, a user dispatching property places it in a lockable compartment. For an impromptu dispatching, the property is already in the lockable compartment. In step 1052, the user engages a service for the dispatch delivery. For the impromptu delivery, a release authority is created or updated, permitting the lockable compartment to release custody to a specified dispatch courier for delivery to a recipient specified by and which typically is the user. For a dispatch delivery, a release authority is created permitting the lockable compartment to release custody to a specified dispatch courier for delivery to a recipient specified by and which may be the user. Regardless of which case is used, namely, a newly created or updated release authority, the release authority permits the engaged service to collect the property from the lockable compartment and make the dispatch delivery and the process ends in step 1054.

Secure Claim Check and Valet Services

In an embodiment, a secure storage platform can secure property in a claim check based service that may be supervised by a proximate attending operation, such as hotel bag-check services. Of a similar nature to bag-check services are coat-check services. Also of similar nature are valet services, where control of a vehicle is temporarily transferred by transferring the keys for the vehicle to a valet attendant. In a claim check application and in a vehicle valet service comprising a secure storage platform and chain of custody service, a transfer of custody of checked property and keys (and indirectly valeted vehicles), and a return transfer thereof, can be securely captured and recorded. In an embodiment, theft of a checked or valeted item such as a checked bag of luggage or a set of car keys (and associated vehicle) can be detected and may be tracked for a potential recovery thereof.

FIG. 11A is an example illustration of a secure storage system 1100 comprising a claim check service. System 1100 comprises a server based system 111 comprising a claim check service, and an electronic lockable tag 1101, also referred to herein as an e-tag. Generally, a claim check service comprises a plurality of e-tags commensurate for an upper potential quantity of concurrently checked items. E-tag 1100 comprises lock access controller 1102 comprising a code derivation key and last access code for generating a verification code for comparison to a received challenge code, whereupon a matching verification code and challenge code lock access controller 1102 opens a lock 1103. Dissimilar to a lockable compartment application disclosed earlier herein, e-tags may be secured to property when assigned custody thereof, rather than securing access to property as in the case of lockable compartment 120 comprising smart lock 122 of FIG. 8D. System 1100 further comprises an operator device 113 and a user device 154 capable of communications with lock access controller 1102 via communications links 198 and 194, respectively, and server based system 111 via communications links 183 and 188, respectively, over a network 180 and a communications link 181 of server based system 111.

FIG. 11B is an example illustration of a process 1120 to check property which begins in step 1122. In step 1124, a code 1106 of e-tag 1101 may be scanned by a user of portable wireless device 154 and checking their property with the claim check service. For example, a user checking a bag may be presented with e-tag 1101 and scan code 1106 thereon using a secure storage app and account recognized by server based system 111 and running on their portable wireless device 154. This action assigns e-tag 1101 for use by the user to check property thereof. Alternatively, if a user does not have a portable wireless device comprising an app and account recognized by sever based system, an operator can register the user within the system using operator device 113 and scanning code 1106 to assign e-tag 1101 to the user. In an alternative embodiment, an alternative method for assignment can be used, such as a claim check operator can reference a user account, such as a conference registration or a hotel registration and link the assignment thereto. Alternatively, server based system 111 may make a selection and assignment and flash an indicator 1104, such as an LED indicator, to alert an operator of the assignment. After e-tag 1101 is assigned in step 1124, in step 1126 a release authority specifying a release to the user as an end-recipient is created and a custody transfer is initiated. An embodiment of a process similar to process 440 of FIG. 4B to open a lockable compartment is used to open lock 1103. Process 440 has been previously discussed in detail and only a brief discussion to clarify the current process embodiment will be discussed. In the current embodiment, a device that was used in the assignment of e-tag 1101 in step 1124, namely, either operator device 113 or user portable wireless device 154 connects to lock access controller 1102 (step 446 of process 440), via communication link 198 or 194, respectively. In an alternative embodiment, where assignment was made by server based system 111, then operator device 113 can be used in the current embodiment of process 440. Regardless of which device is used, lock 1103 is open thereby in cooperation with server based system 111 as illustrated in process 440 FIG. 4B. In step 1128, e-tag 1101 is secured to the property being checked by closing the hasp of lock 1103 and attaching lock to a feature of the property such that it is secured thereto. For example, closing 1103 such that e-tag 1101 is secured to a handle, or feature thereof, of a luggage bag. Or in the case of a valet service, to a key fob remote or key to a vehicle. Once the e-tag is secured to the property, custody is transferred to e-tag 1101 as described in process 820 of FIG. 8B, wherein releasing entity 822 is the user and the receiving entity 826 is e-tag 1101. In step 1128, an image of the checked property may be captured by portable wires device 113 or 154 and communicated to server based system 111 for inclusion in custody event table 900 of FIG. 9A and custody transfer table 930 of FIG. 9B, to document the property being checked. Process 1120 ends in step 1130.

FIG. 11C is an example illustration of a process 1140 to claim checked property which begins in step 1142. In step 1144, code 1106 of e-tag 1101 may be scanned by a user of portable wireless device 154 claiming their property checked with the claim check service using a secure storage app and account recognized by server based system 111 and running on their portable wireless device 154. Alternatively the user may select a function of the app to show currently checked items to retrieve the e-tag based claim check. If operator device 113 or server based system 111 was used to assign e-tag 1101 in step 1124 of process 1120, it may alternatively be used to scan or otherwise retrieve e-tag 1101 after the identity of the user is verified by an operator of the checked storage service. Once e-tag 1101 is determined to be the e-tag with custody of the property of interest, server based system, via portable wireless device 154 or operator device 113 may indicate e-tag 1101 by actuating indicator 1104. In step 1146, the user is authenticated, either through use of their device 154 and secure storage app and account running thereon, or through identity information entered by the operator on operator device 113. Upon authentication, custody is transferred back to the user per the release authority, as described in process 820 of FIG. 8B, wherein releasing entity 822 is e-tag 1101 and the receiving entity 826 is the user. In step 1146, an image of the claimed property may be captured by portable wires device 113 or 154 and communicated to server based system 111 for inclusion in custody event table 900 of FIG. 9A and custody transfer table 930 of FIG. 9B, to document the property being claimed. After custody has been transferred to the user, e-tag 1101 is released, namely, lock 1103 is opened, and e-tag 1101 is removed from the checked property using an embodiment of process 440 of FIG. 4B, as described above to secure e-tag 1101 to the property. Process 1140 ends in step 1150.

In an embodiment, e-tag 1101 may further comprise a tracking device 1105 comprising a location or trackable feature, such as a global positioning system (GPS) capability, and long range communications capability, such as a low-power wide-area network (LPWAN), like ultra-narrowband (UNB). Tracking device 1105 may periodically report its current position to a receiver (not shown) which in turn reports the location of e-tag 1101 to server based system 111. As such, if property in custody of, and to which e-tag 1101 is attached, is stolen, it may be tracked and potentially recovered. Furthermore, when e-tag recognizes movement (a difference in successive GPS readings), it may increase the frequency of position reports, at the expense of battery (not shown) capacity consumption, to support a potential tracking effort. Furthermore, a permitted location or proximate location for e-tag 1101 may be established, such that if e-tag 1101 reports a violating location, an alert can be issued by server based system 111 indicating a potential theft of the property in custody of e-tag 1101.

In an embodiment, a lower cost implementation comprising simple non-electronic printed tags (non-e-tags) having readable codes can be used, wherein the readable codes are read by portable wireless devices 113 and 154 to assign non-e-tags and transfer custody thereto and therefrom. Obviously, these tags are not lockable to property, or capable of utilizing single use access identification codes to securely manage attachment and release. Furthermore, these tags are not capable of further comprising tracking device 1105 for tracking.

The possible and illustrative embodiments disclosed herein should not be construed as an exhaustive list. Rather the various embodiments presented serve to illustrate only some of the various ways to practice the invention and many additional combinations of features and configurations are possible within the scope of the invention disclosed herein. It is to be understood that the detailed example embodiments of the present invention disclosed herein are merely illustrative of the invention that may be embodied in various forms. In addition, each of the examples given in connection with the various embodiments of the invention is intended to be illustrative, and not restrictive.

What is claimed is:

1. A system for processing custody transfers of items among entities of users and lockable compartments, the system comprising:
    a plurality of lockable compartments, wherein a lockable compartment is associated with an identifier and comprises a controllable electromechanical lock controlled by an internal or external lock access controller which controls access to the lockable compartment;
    a plurality of custody transfer records recording custody transfers, wherein a custody transfer record of a custody transfer comprises:
        an identifier of a releasing entity releasing custody in the custody transfer;
        an identifier of a receiving entity receiving custody in the custody transfer;
        an identifier of one or more items of which custody is transferred from the releasing entity to the receiving entity; and
        an identifier of a chain of custody to which at least the custody transfer record and the custody transfer recorded therein are associated;
    a server based system configured to communicate over a communications network and interact with portable wireless devices and/or lockable compartments and process custody transfers, wherein:
        portable wireless devices are usable by users to interact with the server based system and/or lockable compartments to transfer custodies of items;
        in response to receiving by the server based system from a releasing user, a custody transfer request to transfer custody of one or more items to a receiving lockable compartment comprising a controllable electromechanical lock controlled by an internal or external lock access controller, the server based system is configured to provide an access authentication code useable by the lock access controller to verify an access request associated with the custody transfer request, wherein if the access request is verified, the lock access controller provides access to the receiving lockable compartment and the server based system generates a custody transfer record, wherein the custody transfer record comprises:
            an identifier of the releasing user;
            an identifier of the one of more items of the custody transfer request;
            an identifier of the receiving lockable compartment; and
            an identifier of a chain of custody to which at least the custody transfer record and the custody transfer recorded therein are associated; and
        in response to receiving by the server based system from a receiving user, a custody transfer request to transfer custody of one or more items from a releasing lockable compartment comprising a controllable electromechanical lock controlled by an internal or external lock access controller, the server based system is configured to provide an access authentication code useable by the lock access controller to verify an access request associated with the custody transfer, wherein if the access request is verified, the lock access controller provides access to the releasing lockable compartment and the server based system generates a custody transfer record, wherein the custody transfer record comprises:
            an identifier of the releasing lockable compartment;
            an identifier of the one of more items of the custody transfer request;
            an identifier of the receiving user; and
            an identifier of a chain of custody to which at least the custody transfer record and the custody transfer recorded therein are associated.

2. The system of claim 1, wherein the server based system configured to process custody transfers is further configured to receive a release authority in conjunction with the receiving of a first custody transfer request to transfer custody of one or more items from a releasing user to a receiving lockable compartment, wherein in the first custody transfer request a first custody transfer record is generated, and the release authority specifies requirements and/or actions of a subsequent second custody transfer of the one or more items from the receiving lockable compartment to a receiving user.

3. The system of claim 2, wherein if the release authority specifies a provision of an access token usable by the receiving user of the second custody transfer, and an email address and/or a phone number for delivery of the access token to the receiving user of the second custody transfer, the server based system is further configured to:
    generate an access token;
    email and/or text the access token to the email address and/or the phone number for delivery of the access token to the receiving user of the second custody transfer; and
    provide the access token for submission to the lock access controller controlling the electromechanical lock of the receiving lockable compartment, wherein upon an attempt of the second custody transfer:
        the receiving user of the second custody transfer enters an access token into a keypad operatively coupled to the lock access controller;

the lock access controller compares the access token generated by the server based system to the access token entered by the receiving user of the second custody transfer; and if the comparison indicates a match between the access token generated by the server based system and the access token entered by the receiving user of the second custody transfer, the lock access controller provides access to the receiving lockable compartment and the server based system generates a second custody transfer record, wherein the second custody transfer record comprises:
an identifier of the receiving lockable compartment;
an identifier of the one of more items;
an identifier of the receiving user of the second custody transfer; and
an identifier of a chain of custody to which at least the first custody transfer record and the first custody transfer recorded therein, and the second custody transfer record and the second custody transfer recorded therein are associated.

4. The system of claim 1, wherein the server based system further comprises an access authentication code generator, wherein in response to an access request associated with a custody transfer request to transfer custody of one of more items between a user and a lockable compartment, the access authentication code generator of the server based system generates an access authentication code by encrypting an input code generated and retained thereby in response to a previous access request of the lockable compartment, and provides the access authentication code for submission to a lock access controller controlling an electromechanical lock of the lockable compartment.

5. The system of claim 4, wherein the lock access controller comprises an access authentication code generator, wherein in response to the access request, the access authentication code generator of the lock access controller generates an access authentication code by encrypting an input code generated and retained thereby in response to a previous access request, wherein if the access authentication code generated by the lock access controller matches the access authentication code generated by the access authentication code generator of the server based system, the access request is verified and the lock access controller provides access to the lockable compartment and the server based system generates a custody transfer record, wherein the custody transfer record comprises:
an identifier of the lockable compartment;
an identifier of the one of more items of the custody transfer request;
an identifier of the user; and
an identifier of a chain of custody to which at least the custody transfer record and the custody transfer recorded therein are associated.

6. The system of claim 1, wherein the server based system distributes custody transfer records, wherein a custody transfer record is distributed to a user having participated in a custody transfer recorded therein and/or a user having participated in a custody transfer associated with a chain of custody to which the custody transfer record is associated.

7. The system of claim 6, wherein one or more of the plurality of custody transfer records have associated custody transfer record certificates, wherein a custody transfer record certificate provides authentication of data comprised by its associated custody transfer record.

8. The system of claim 7, wherein a custody transfer record certificate is a cryptographic hash of data comprised by its associated custody transfer record and enables detection of an alteration made to the data, wherein the alteration results in a change in the calculated cryptographic hash.

9. The system of claim 7, wherein the system writes custody transfer record certificates to a ledger as ledger entries associated to custody transfer records, wherein:
the ledger can be queried to retrieve a ledger entry comprising a custody transfer record certificate associated with a specified custody transfer record; and
the custody transfer record certificate of the retrieved ledger entry can be used to authenticate the specified custody transfer record to determine if data comprised by the specified custody transfer record has been altered.

10. The system of claim 9, wherein an alteration to data comprised by the ledger is detectable, wherein:
the ledger entries are written into blocks of ledger entries;
each block excluding an initial block is linked to a nearest previous block, wherein the link comprises an entry in the block of a cryptographic hash calculated over the data contents of the nearest previous block including a cryptographic hash of its nearest previous block entered therein, unless the nearest previous block is the initial block; and
an alteration to any data in a given block after a cryptographic hash is calculated for the given block and all cryptographic hashes for the subsequent blocks linked thereto which are calculated prior to the alteration, will result in a change to the cryptographic hash of the given block and all the cryptographic hashes for the subsequent blocks linked thereto which are calculated prior to the alteration, when they are recalculated.

11. The system of claim 10, wherein multiple entities maintain a copy of the ledger, wherein each entity independently calculates cryptographic hashes, wherein a consensus of a majority entities indicating a same hash calculation indicates a correct hash calculation, and those entities calculating a incorrect hash calculation can be flagged as comprising invalid ledger entries.

12. The system of claim 1, wherein one or more lockable compartments comprise a door status sensor indicating a compartment door thereof open status or a compartment door thereof closed status, wherein door opening events and door closing events are timestamped and can be associated with custody transfers.

13. The system of claim 1, wherein one or more lockable compartments comprise a camera configured to record images of contents of a lockable compartment, wherein images are captured, timestamped and can be associated with custody transfers.

14. A method for processing custody transfers of items among entities of users and lockable compartments, the method comprising:
providing a system comprising:
a plurality of lockable compartments, wherein a lockable compartment is associated with an identifier and comprises a controllable electromechanical lock controlled by an internal or external lock access controller which controls access to the lockable compartment;
a plurality of custody transfer records recording custody transfers, wherein a custody transfer record of a custody transfer comprises:
an identifier of a releasing entity releasing custody in the custody transfer;
an identifier of a receiving entity receiving custody in the custody transfer;

an identifier of one or more items of which custody is transferred from the releasing entity to the receiving entity; and an identifier of a chain of custody to which at least the custody transfer record and the custody transfer recorded therein are associated;

a server based system configured to communicate over a communications network and interact with portable wireless devices and/or lockable compartments; and a plurality of portable wireless devices usable by users to interact with the server based system and/or lockable compartments;

receiving by the server based system from a first user via a first portable wireless device, a first custody transfer request to a custody transfer of a first one or more items to a first lockable compartment;

providing by the server based system in response to the first custody transfer request, a first provided access authentication code to a lock access controller controlling access to the first lockable compartment;

validating by the lock access controller controlling access to the first lockable compartment, a first access request associated with the first custody transfer request using the first provided access authentication code, and providing the first user access to the first lockable compartment at least in part due to a successful validation of the first access request; and generating by the server based system at least in part due to the providing the first user access to the first lockable compartment, a first custody transfer record comprising:

an identifier of the first user;
an identifier of the first one of more items;
an identifier of the first lockable compartment; and
an identifier of a first chain of custody to which at least the first custody transfer record and the custody transfer recorded therein are associated.

15. The method of claim 14, further comprising:
receiving by the server based system from a second user via a second portable wireless device, a second custody transfer request to a custody transfer of the first one or more items from the first lockable compartment;

providing by the server based system in response to the second custody transfer request, a second provided access authentication code to the lock access controller controlling access to the first lockable compartment;

validating by the lock access controller controlling access to the first lockable compartment, a second access request associated with the second custody transfer request, using the second provided access authentication code, and providing the second user access to the first lockable compartment at least in part due to a successful validation of the second access request; and generating by the server based system at least in part due to the providing the second user access to the first lockable compartment, a second custody transfer record comprising:

an identifier of the first lockable compartment;
an identifier of the first one of more items;
an identifier of the second user; and
an identifier of the first chain of custody to which at least the first custody transfer record and the custody transfer recorded therein, and the second custody transfer record and the custody transfer recorded therein, are associated.

16. The method of claim 14, further comprising:
receiving by the server based system from a second user via a second portable wireless device, a second custody transfer request to a custody transfer of the first one or more items from the first lockable compartment;

providing by the server based system in response to the second custody transfer request, a second provided access authentication code to the lock access controller controlling access to the first lockable compartment;

validating by the lock access controller controlling access to the first lockable compartment, a second access request associated with the second custody transfer request, using the second provided access authentication code, and not providing the second user access to the first lockable compartment at least in part due to an unsuccessful validation of the second access request.

17. The method of claim 14, wherein the server based system receives a release authority in conjunction with the first custody transfer request, wherein the release authority specifies a provision of an access token usable by a second user to access the first lockable compartment and receive custody of the first one or more items, and the release authority specifies an email address and/or a phone number for delivery of the access token to the second user, the method further comprising:

generating by the server based system, an access token;
emailing and/or texting by the server based system, the access token to the email address and/or the phone number for delivery of the access token to the second user; and providing by the server based system, the access token for submission to the lock access controller controlling access to the first lockable compartment;

receiving by the lock access controller controlling access to the first lockable compartment, an entered access token entered by the second user into a keypad operatively coupled to the lock access controller controlling access to the first lockable compartment;

comparing by the lock access controller controlling access to the first lockable compartment, the access token generated by the server based system to the access token entered by the second user and providing the second user access to the first lockable compartment at least in part due to the access token generated by the server matching the access token entered by the second user; and generating by the server based system at least in part due to the providing the second user access to the first lockable compartment, a second custody transfer record comprising:

an identifier of the first lockable compartment;
an identifier of the first one of more items;
an identifier of the second user; and
an identifier of the first chain of custody to which at least the first custody transfer record and the custody transfer recorded therein, and the second custody transfer record and the custody transfer recorded therein, are associated.

18. The method of claim 14, wherein the server based system receives a release authority in conjunction with the first custody transfer request, wherein the release authority specifies a provision of an access token usable by a second user to access the first lockable compartment and receive custody of the first one or more items, and the release authority specifies an email address and/or a phone number for delivery of the access token to the second user, the method further comprising:

generating by the server based system, an access token;
emailing and/or texting by the server based system, the access token to the email address and/or the phone number for delivery of the access token to the second user; and
providing by the server based system, the access token for submission to the lock access controller controlling access to the first lockable compartment;
receiving by the lock access controller controlling access to the first lockable compartment, an entered access token entered by the second user into a keypad operatively coupled to the lock access controller controlling access to the first lockable compartment;
comparing by the lock access controller controlling access to the first lockable compartment, the access token generated by the server based system to the access token entered by the second user and not providing the second user access to the first lockable compartment at least in part due to the access token generated by the server based system not matching the access token entered by the second user.

19. A non-transitory computer-readable medium comprising instructions that, when executed by one or more processors, the one or more processors are configured to:
receive from a first user via a first portable wireless device, a first custody transfer request to perform a custody transfer of a first one or more items to a first lockable compartment;
provide in response to the first custody transfer request, a first provided access authentication code to a lock access controller controlling access to the first lockable compartment;
receive indication that a first access request associated with the first custody transfer request has been successfully verified using the first provided access authentication code, and that the first user has been provided access to the first lockable compartment; and
generate at least in part due to the providing the first user access to the first lockable compartment, a first custody transfer record comprising:
an identifier of the first user;
an identifier of the first one of more items;
an identifier of the first lockable compartment; and
an identifier of a first chain of custody to which at least the first custody transfer record and a custody transfer event recorded therein are associated.

20. The non-transitory computer-readable medium of claim 19, further comprising instructions that, when executed by the one or more processors, the one or more processors are further configured to:
receive a release authority in conjunction with the first custody transfer request, wherein the release authority specifies a provision of an access token usable by a second user to access the first lockable compartment and receive custody of the first one or more items, and the release authority specifies an email address and/or a phone number for delivery of the access token to the second user;
generate an access token;
email and/or text the access token to the email address and/or the phone number for delivery of the access token to the second user;
encrypt the access token using a first encryption key comprised by both the server based system and the lock access controller controlling access to the first lockable compartment for submission thereto;
receive an indication that a decrypted submitted encrypted access token, decrypted using the first encryption key matches an access token entered by the second user, or an encrypted access token entered by the second user, encrypted using the first encryption key, matches the submitted encrypted access token, and due at least in part to a match between the submitted and the entered access tokens a providing of the second user access to the first lockable compartment; and
generate, a second custody transfer record comprising:
an identifier of the first lockable compartment;
an identifier of the first one of more items;
an identifier of the second user; and
an identifier of the first chain of custody to which at least the first custody transfer record and the custody transfer recorded therein, and the second custody transfer record and the custody transfer recorded therein, are associated.

* * * * *